US012020803B2

(12) United States Patent
Narayanan

(10) Patent No.: US 12,020,803 B2
(45) Date of Patent: Jun. 25, 2024

(54) INTELLIGENT META PACS SYSTEM AND SERVER

(71) Applicant: Krishnamurthy Narayanan, New York, NY (US)

(72) Inventor: Krishnamurthy Narayanan, New York, NY (US)

( * ) Notice: Subject to any disclaimer, the term of this patent is extended or adjusted under 35 U.S.C. 154(b) by 863 days.

(21) Appl. No.: 17/073,984

(22) Filed: Oct. 19, 2020

(65) Prior Publication Data

US 2021/0265041 A1     Aug. 26, 2021

Related U.S. Application Data

(60) Provisional application No. 62/981,280, filed on Feb. 25, 2020.

(51) Int. Cl.
| | |
|---|---|
| *G16H 30/20* | (2018.01) |
| *G06F 16/23* | (2019.01) |
| *G06F 21/62* | (2013.01) |
| *G16H 15/00* | (2018.01) |
| *G16H 30/40* | (2018.01) |
| *G16H 40/20* | (2018.01) |
| *G16H 50/20* | (2018.01) |

(52) U.S. Cl.
CPC ......... *G16H 30/20* (2018.01); *G06F 16/2365* (2019.01); *G06F 21/6218* (2013.01); *G16H 15/00* (2018.01); *G16H 30/40* (2018.01); *G16H 40/20* (2018.01); *G16H 50/20* (2018.01)

(58) Field of Classification Search
CPC .............................. G16H 30/20; G16H 30/40
USPC ........................................................... 705/3
See application file for complete search history.

(56) References Cited

U.S. PATENT DOCUMENTS

| | | |
|---|---|---|
| 5,469,353 A | 11/1995 | Pinsky et al. |
| 5,513,101 A | 4/1996 | Pinsky et al. |

(Continued)

FOREIGN PATENT DOCUMENTS

| | | | |
|---|---|---|---|
| WO | 2010/0704088 A1 | 6/2010 | |
| WO | WO-2011159849 A1 * | 12/2011 | ............. G06T 9/005 |

OTHER PUBLICATIONS

Kang, Hyun Jae; Medical Ultrasound Imaging and Interventional Component (MUSiiC) Framework for Advanced Ultrasound Image-guided Therapy; The Johns Hopkins University. ProQuest Dissertations Publishing, 2015. 10302217. (Year: 2015).*

(Continued)

*Primary Examiner* — Hiep V Nguyen
(74) *Attorney, Agent, or Firm* — Gloria Tsui-Yip; Gottlieb, Rackman & Reisman, P.C.

(57) ABSTRACT

A system to transparently and efficiently coordinate a process across at least two independent Picture Archiving and Communication System (PACS) to allow interoperability of the PACS to acquire, retrieve, transmit, store and/or display medical images of patients. The system includes: (1) a rule engine defining a set of transformation rules for data related to the images; (2) a data unification and transformation engine identifying and resolving any conflict of the data, and tracking and assigning a unique super-identity or super-value to the data; (3) at least one database storing a list of the data and the tracking and assignment of the super-identities or super-values; (4) a security framework that controls access to the data; and (5) a control engine performing the process steps.

16 Claims, 34 Drawing Sheets

Overview of IMPACS System/Server 200

(56) References Cited

U.S. PATENT DOCUMENTS

| | | | |
|---|---|---|---|
| 5,655,084 | A | 8/1997 | Pinsky et al. |
| 8,874,453 | B2 | 10/2014 | Menschik et al. |
| 10,810,550 | B1 | 10/2020 | Narayanan |
| 2004/0193901 | A1 | 9/2004 | Bharara |
| 2007/0118540 | A1 | 5/2007 | Guo |
| 2009/0016425 | A1 | 6/2009 | Menschik et al. |
| 2011/0153351 | A1 | 6/2011 | Vesper et al. |
| 2011/0246239 | A1* | 10/2011 | Vdovjak ............... G16H 30/20 705/3 |
| 2013/0129165 | A1 | 5/2013 | Dekel et al. |

OTHER PUBLICATIONS

Wilson, D.L., et al., "Virtual PACS, open systems, and the National Information Infrastructure," Proc. SPIE 2435, Medical Imaging 1995: PACS Design and Evaluation: Engineering and Clinical Issues, May 12, 1995.

Wilson, D.L., et al., "Filmless PACS in a multiple facility environment," Proc. SPIE 2711, Medical Imaging 1996: PACS Design and Evaluation: Engineering and Clinical Issues, May 1, 1996.

Chanin, D.S., Opinion: Is it time for 'PACSter'?, Journal of Digital Imaging, vol. 14, No. 2 , pp. 52-53, Jun. 2001.

Hiroyasu, T., et al., Distributed PACS using Network Shared File System, 2011.

Digital Imaging and Communications in Medicine (DICOM), "DICOM Strategic Document", http://dicom.nema.org/dicom/geninfo/Strategy.pdf, Jun. 16, 2010.

Martinez, Ralph, Distributed System Software Via NSFNET for Global Picture Archiving and Communication Systems, National Science Foundation, Award Abstract #9106155, Sep. 15, 1991, posted at www.nsf.gov, retrieved on Feb. 3, 2021, <https://www.nsf.gov/awardsearch/showAward?AWD_ID=9106155>.

R. Martinez, Y. Alsafadi and J. Kim, "Design of multimedia global PACS distributed computing environment," Proceedings of the Twenty-Eighth Annual Hawaii International Conference on System Sciences, Wailea, HI, USA, 1995, pp. 461-469 vol.3, doi: 10.1109/HICSS.1995.375629.

Jiang et al. "Multi-physics bi-Functional intelligent meta-device based on the shape memory 1-16 alloys." Crystals 9.9 (2019): 438. Aug. 23, 2019 (Aug. 23, 2019) Retrieved on Apr. 10, 2021 (Apr. 10, 2021) from <https://www.mdpi.com/2073-4352/9/9/438> entire document.

Digital Imaging and Communications in Medicine. "Strategic Document." 08 Mar. 1-16, 2017 (Mar. 8, 2017) Retrieved on Apr. 10, 2021 (Apr. 10, 2021) from <http://dicom.nema.org/dicom/geninfo/Strategy.pdf> entire document.

PCT Search Report and Written Opinion for PCT/US2021/017789, USPTO Searching Authority, May 7, 2021.

Supplementary European Search Report, European Patent Office, Application No. 21717304.6, Nov. 28, 2022.

Oladiran Olakunle et al., "Conversion of JPG Image into DICOM Image Format with One Click Tagging", May 14, 2017, arxiv.org, Cornell University Library, 201 OLIN Library Cornell University Ithaca, NY 14853, pp. 61-70, XP047600537, [retrieved on May 14, 2017].

* cited by examiner

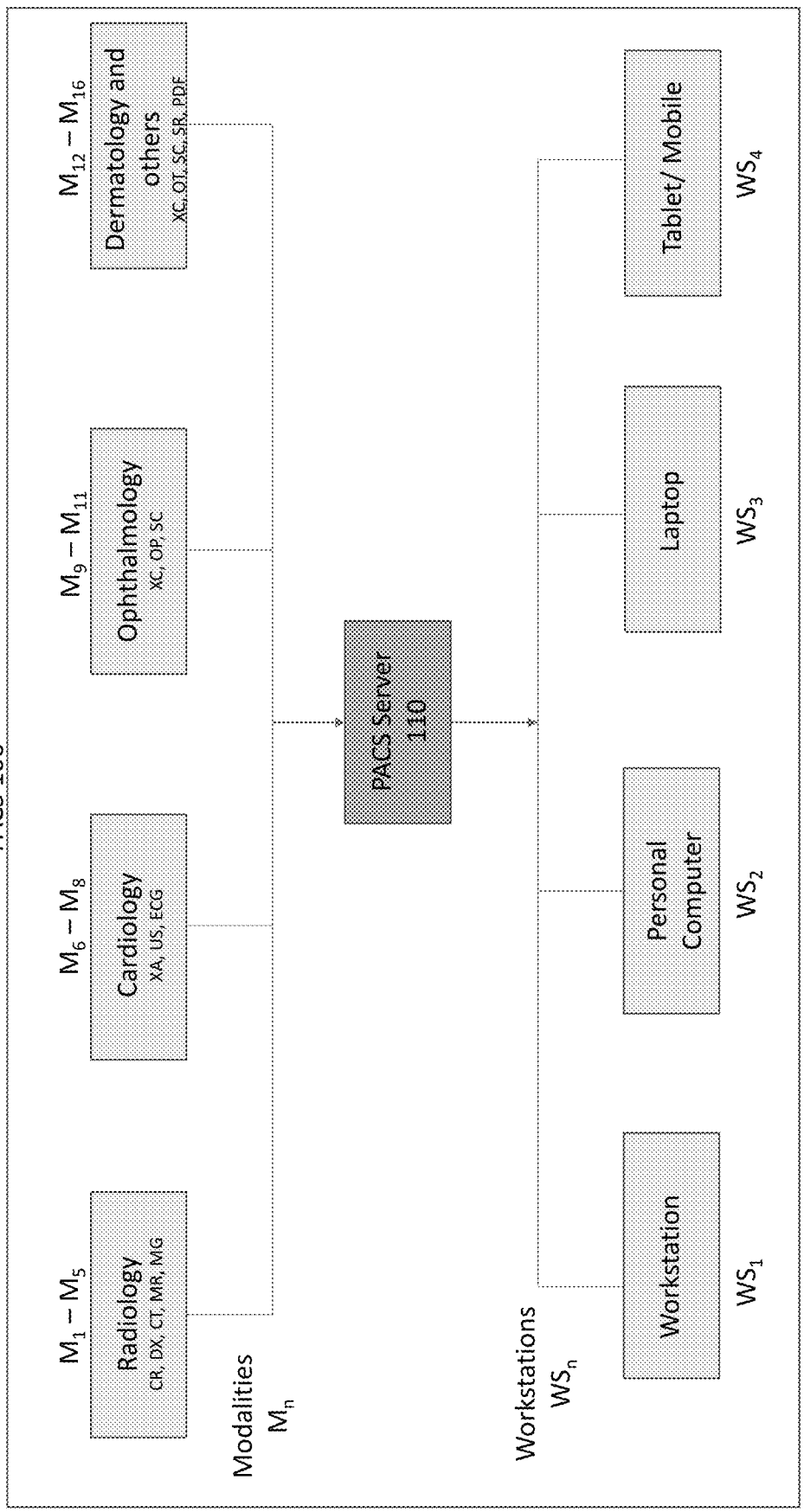

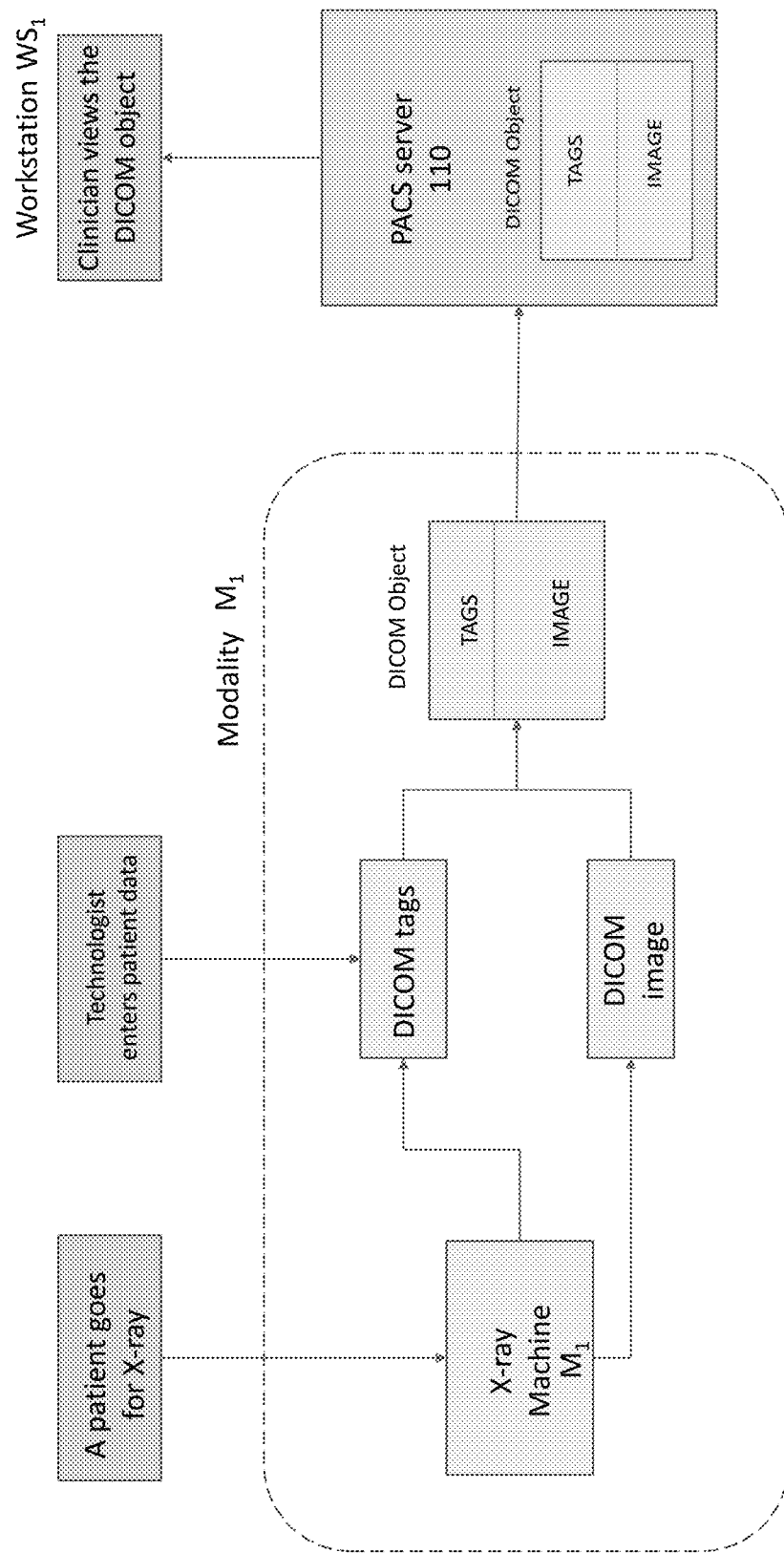
Figure 2: DICOM Workflow With a PACS (Prior Art)

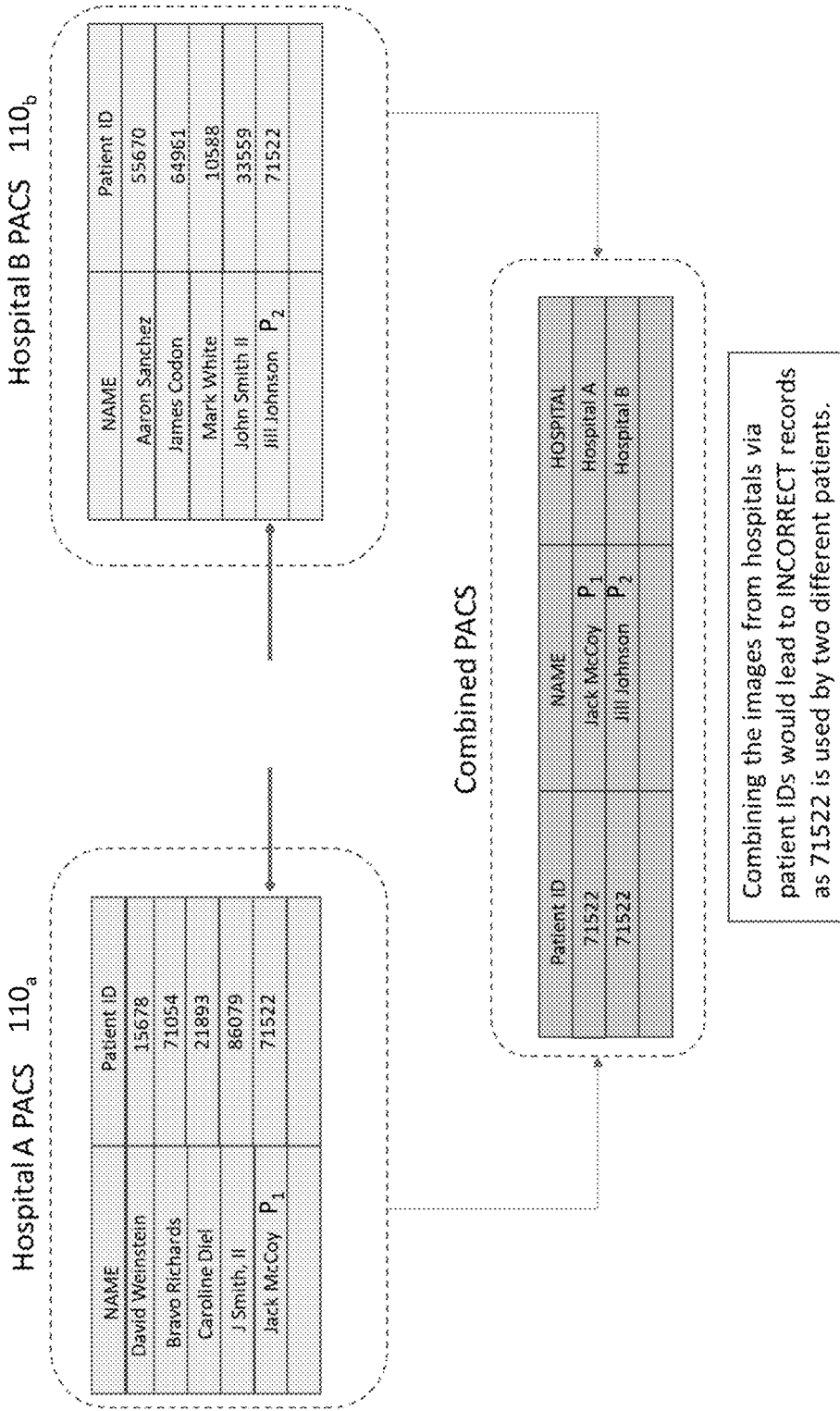
Figure 3: Patient Unification Problems with with Non-unique Patient Identifiers (Prior Art)

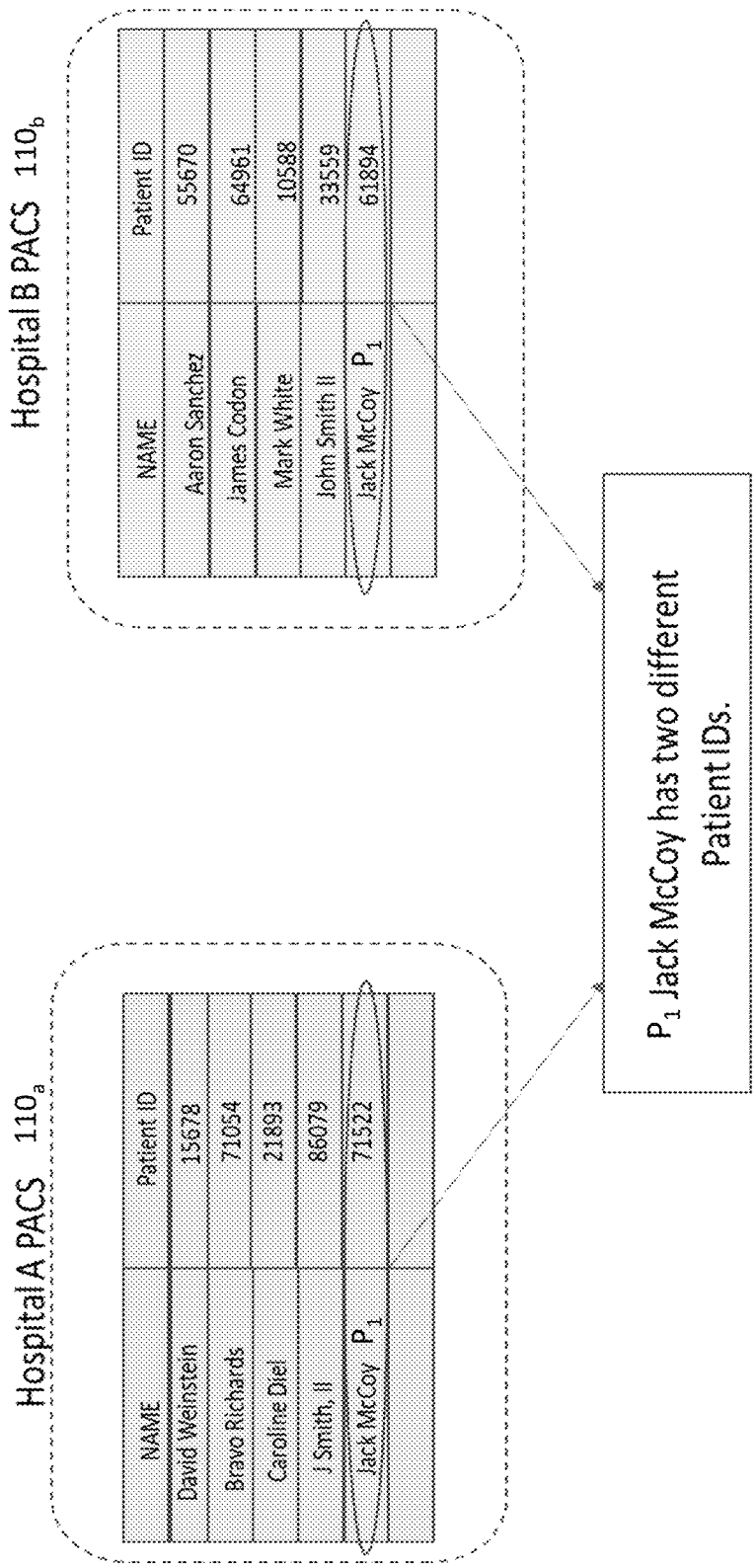
Figure 4: Patient Unification Problems even with Unique Patient Identifiers (Prior Art)

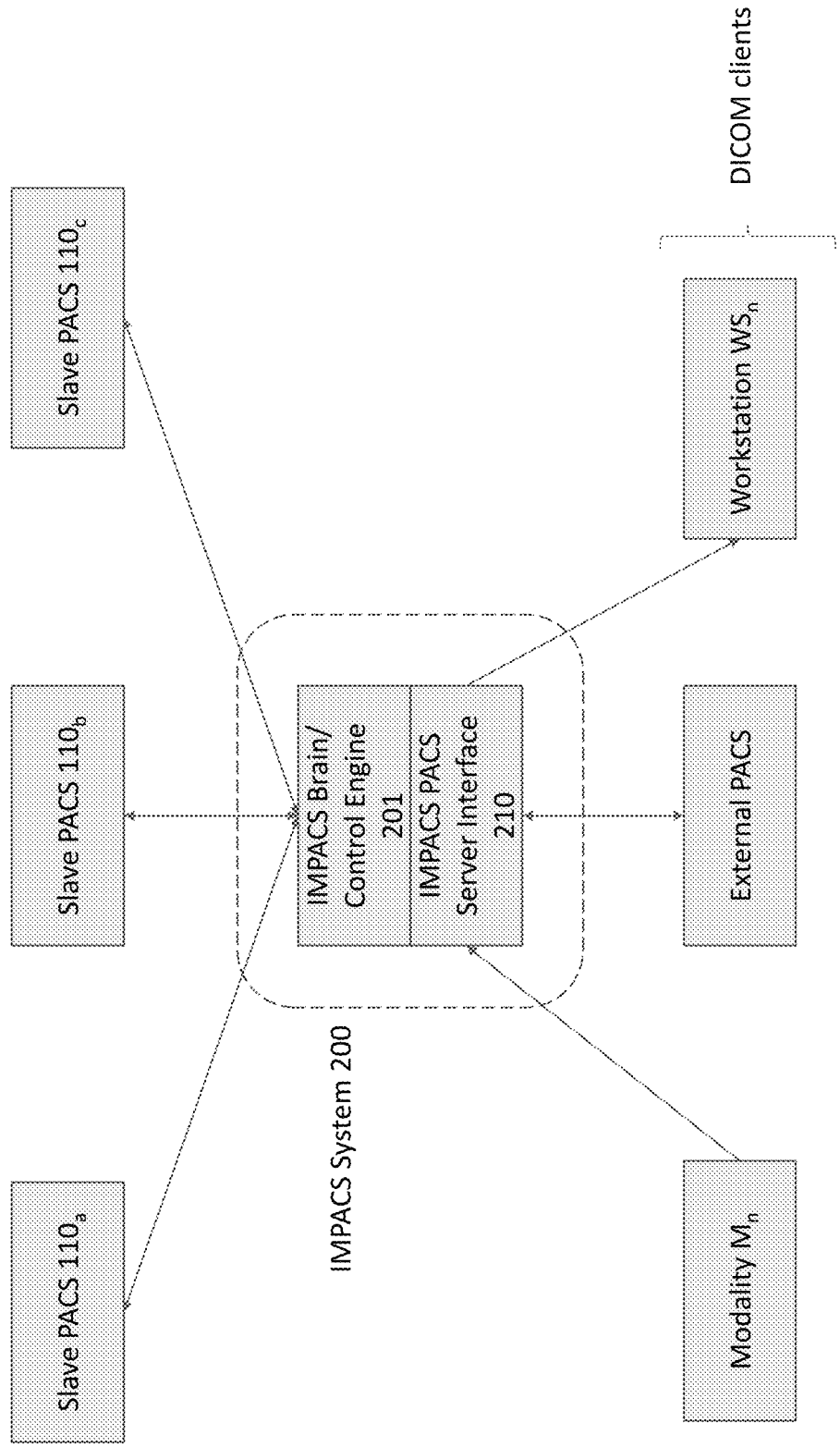

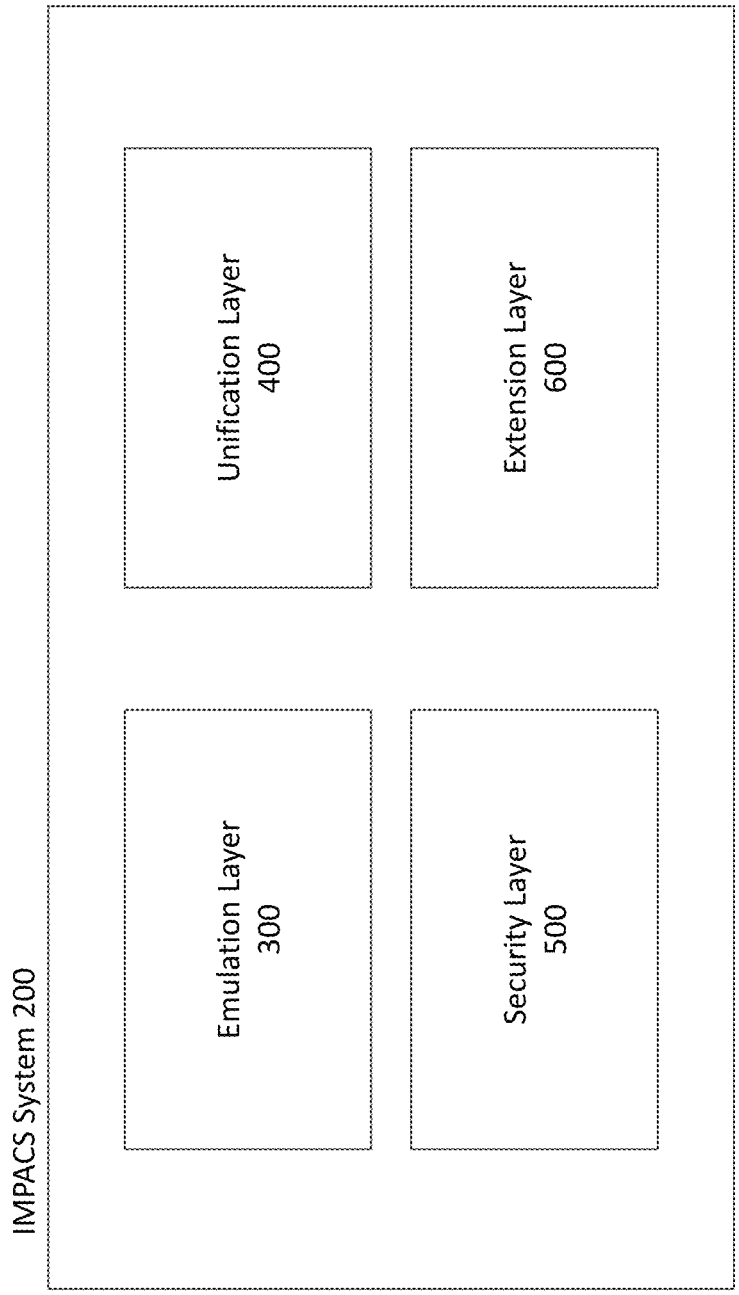

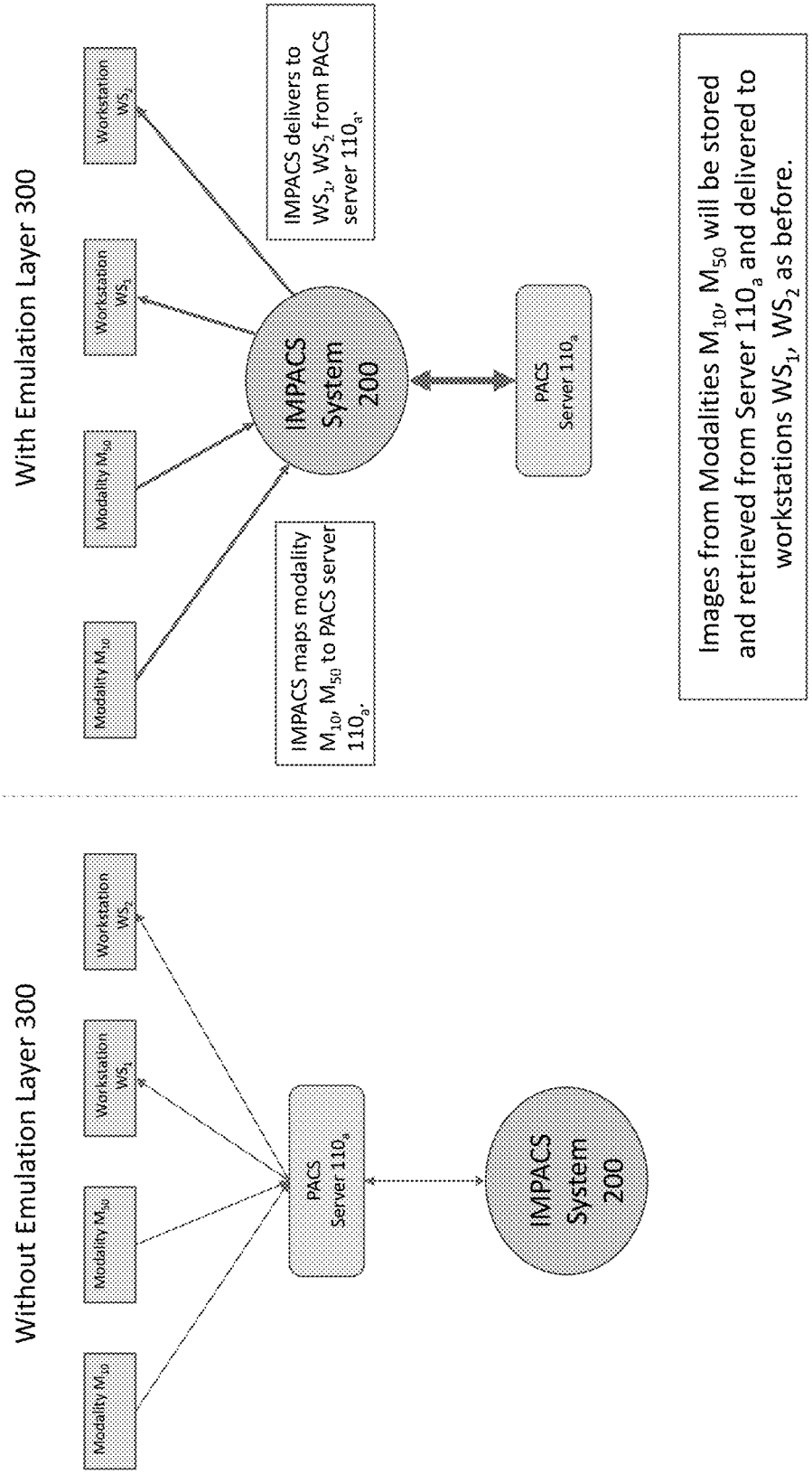

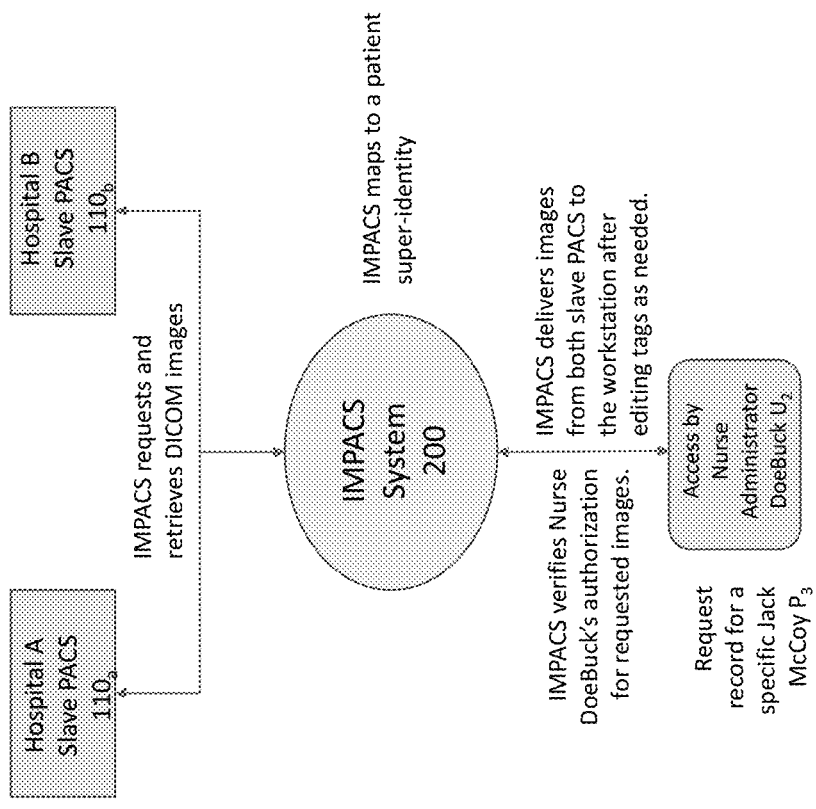
Figure 8: IMPACS System's 200 Unification Layer 400 Overview

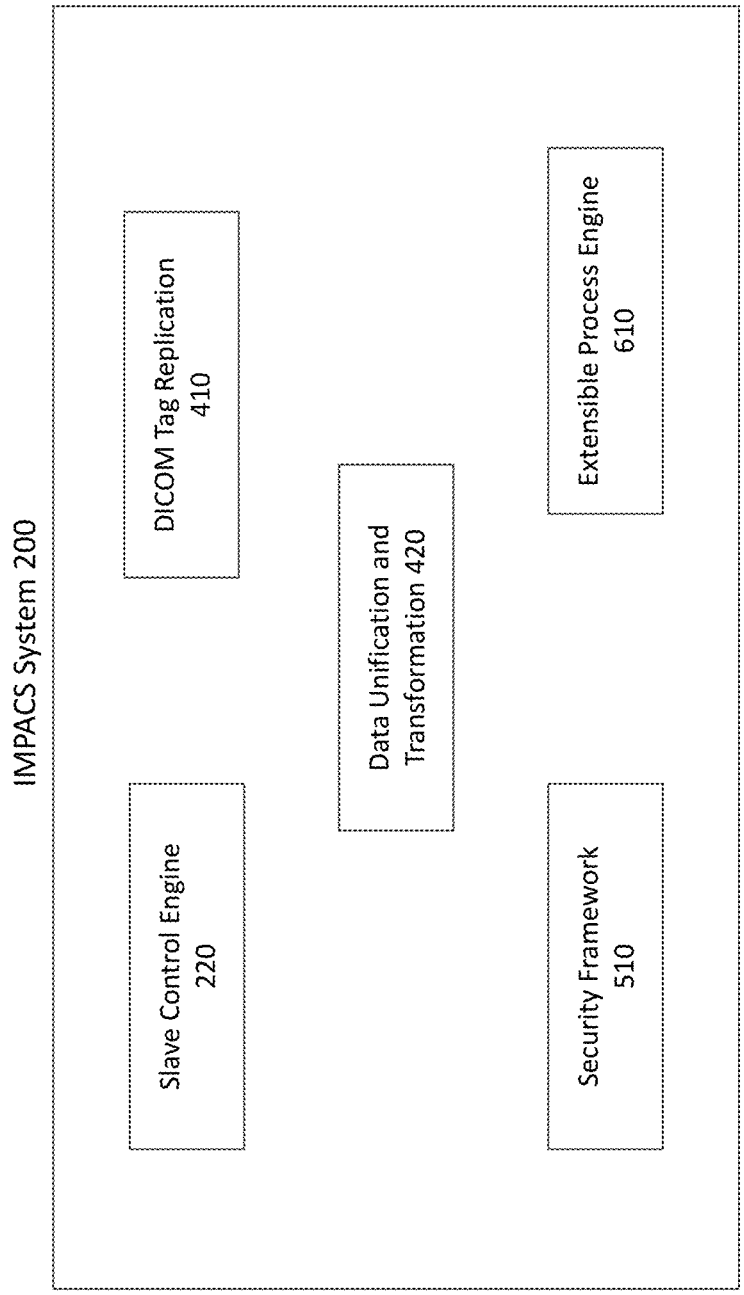
Figure 9: IMPACS System 200 Main Implementation Elements

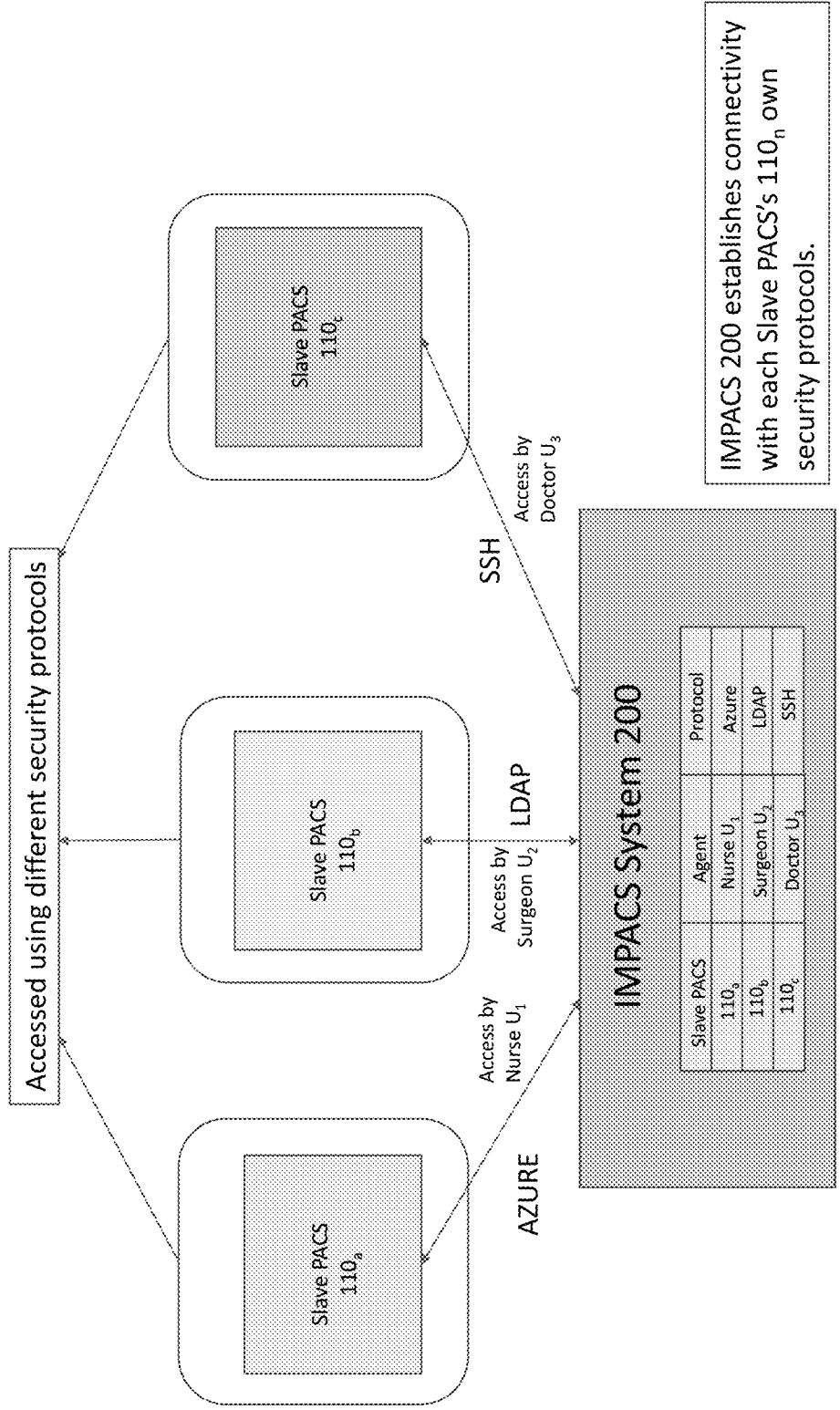
Figure 10: IMPACS System 200 with Slave Servers $110_n$ using Different Security Protocols

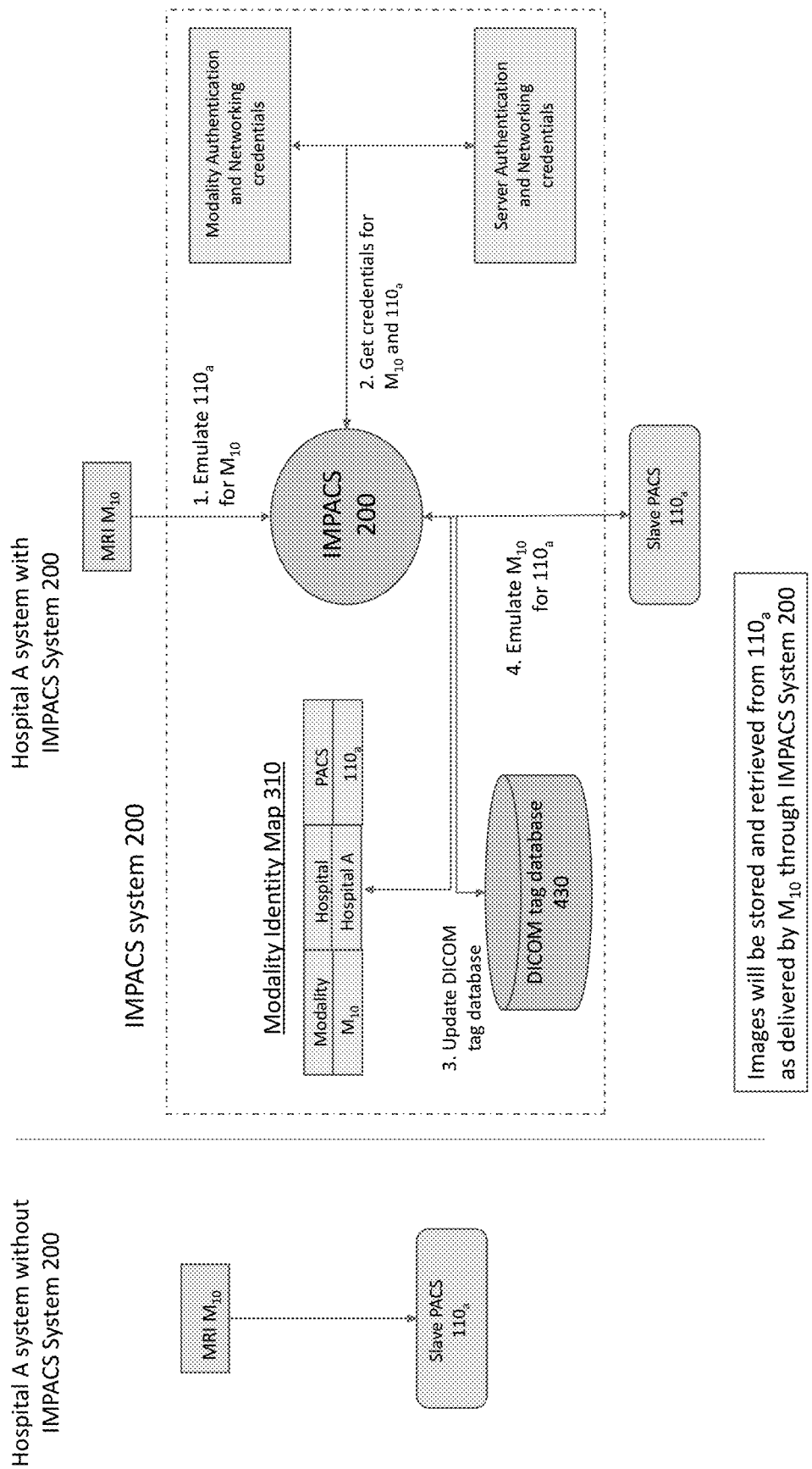
Figure 11: IMPACS System's 200 Emulation Layer 300 for Modalities $M_n$

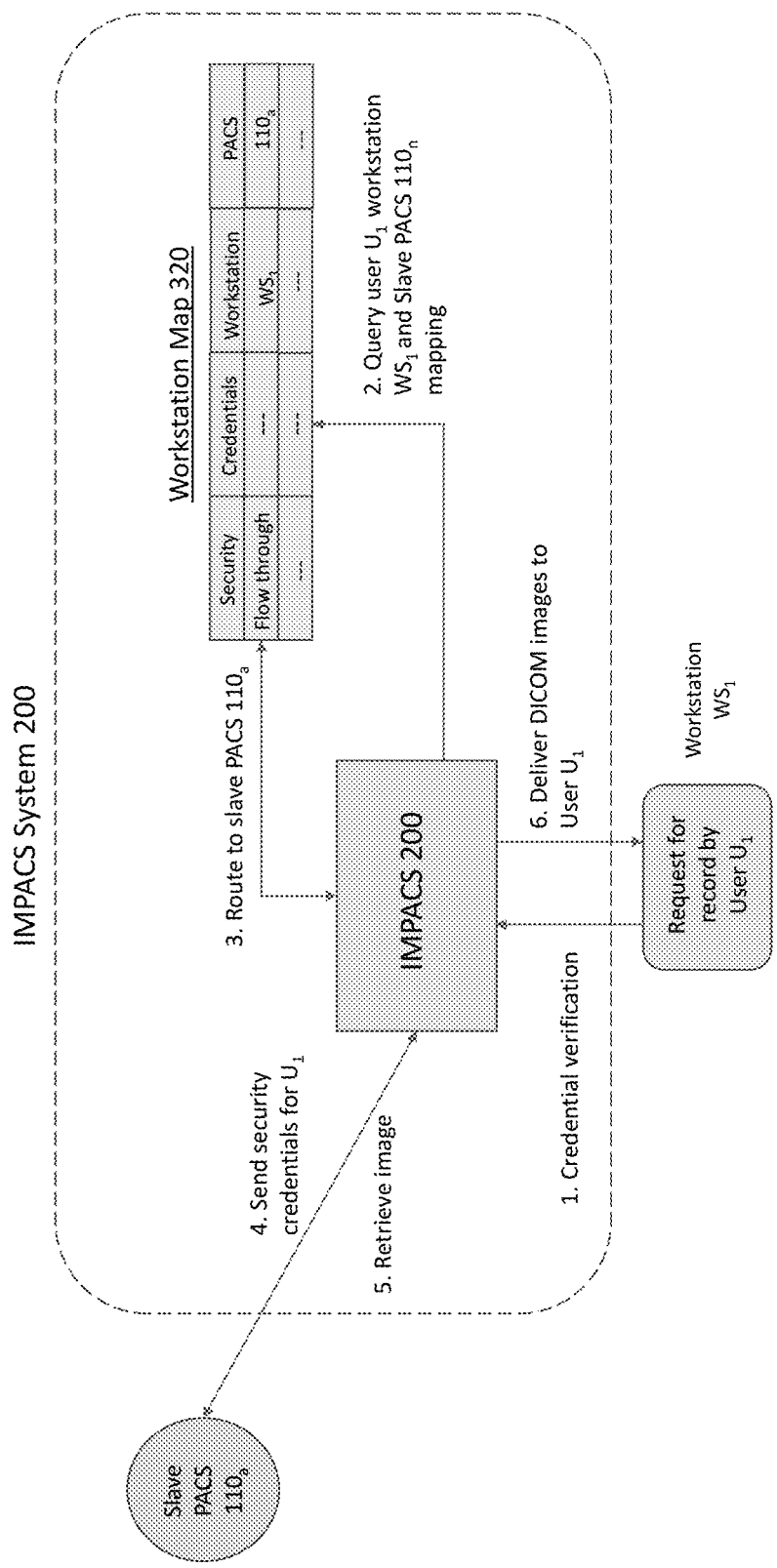
Figure 12: IMPACS System 200 in Emulation Mode 300 with Workstation $WS_n$ Mapping for Slave PACS $110_n$ User Security

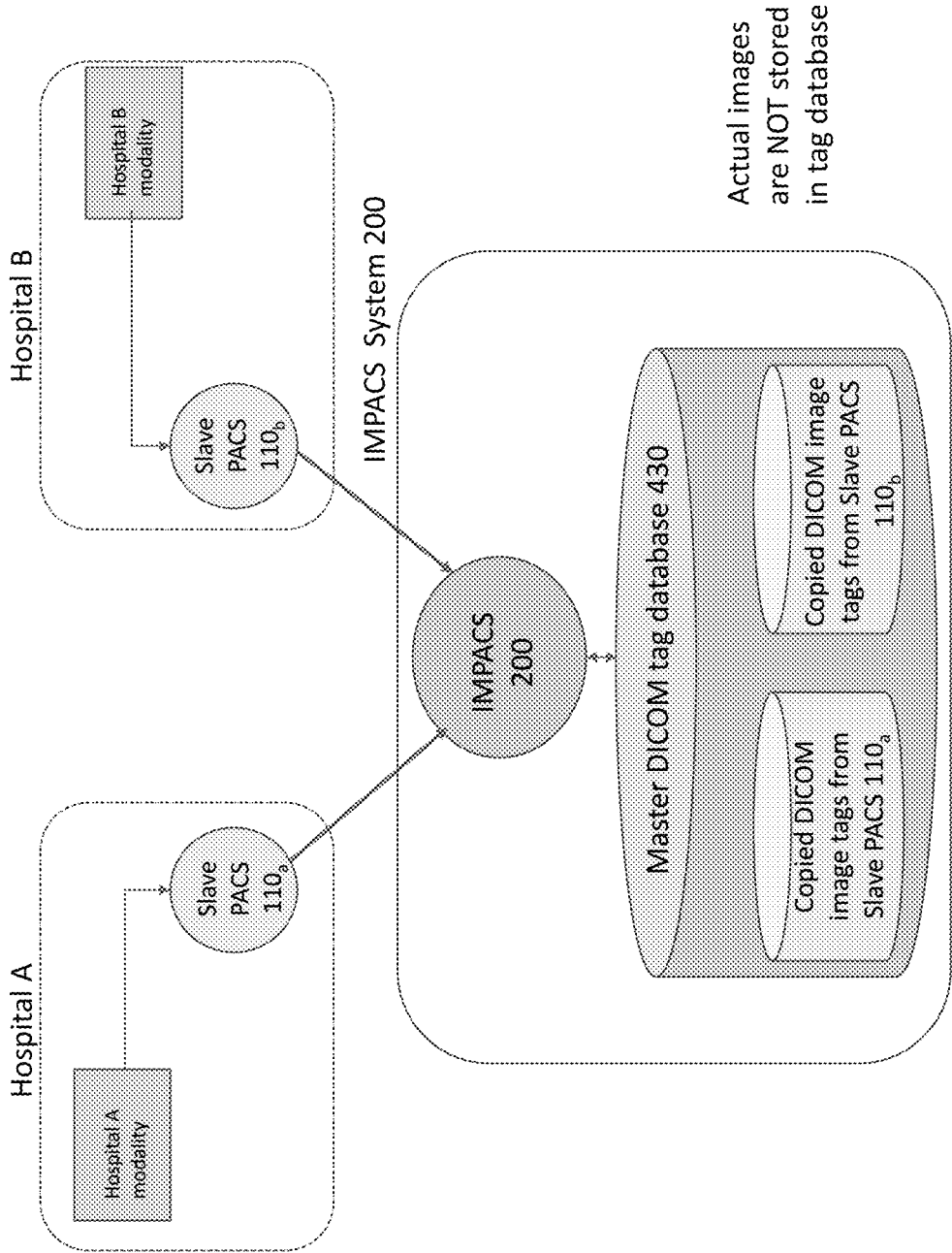
Figure 13: DICOM Tag Database 430 in IMPACS System 200

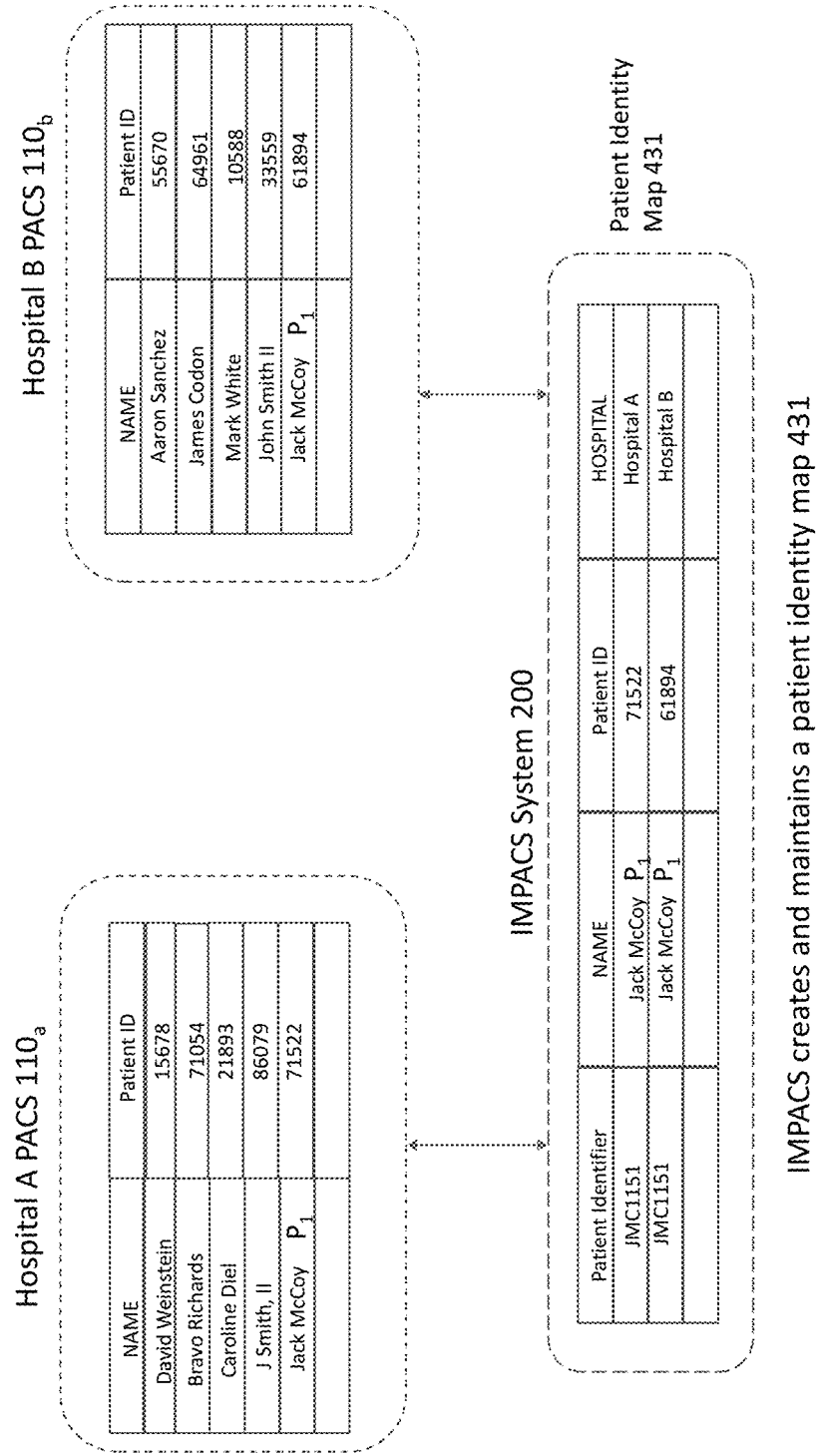
Figure 14: Setup of IMPACS System 200 Patient Super-Identity Map 431

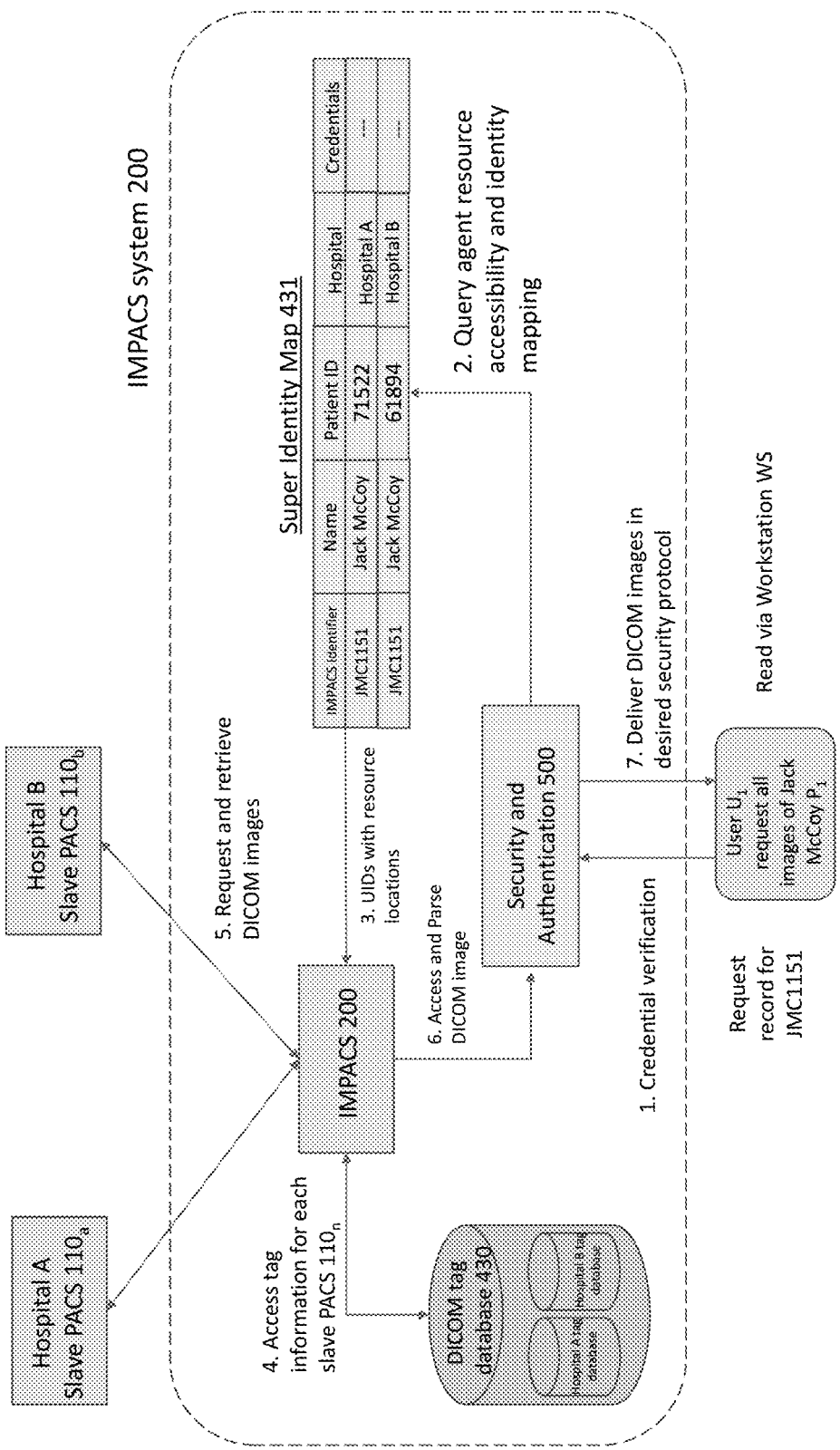
Figure 15: Searching IMPACS System 200 with Patient Super-Identity

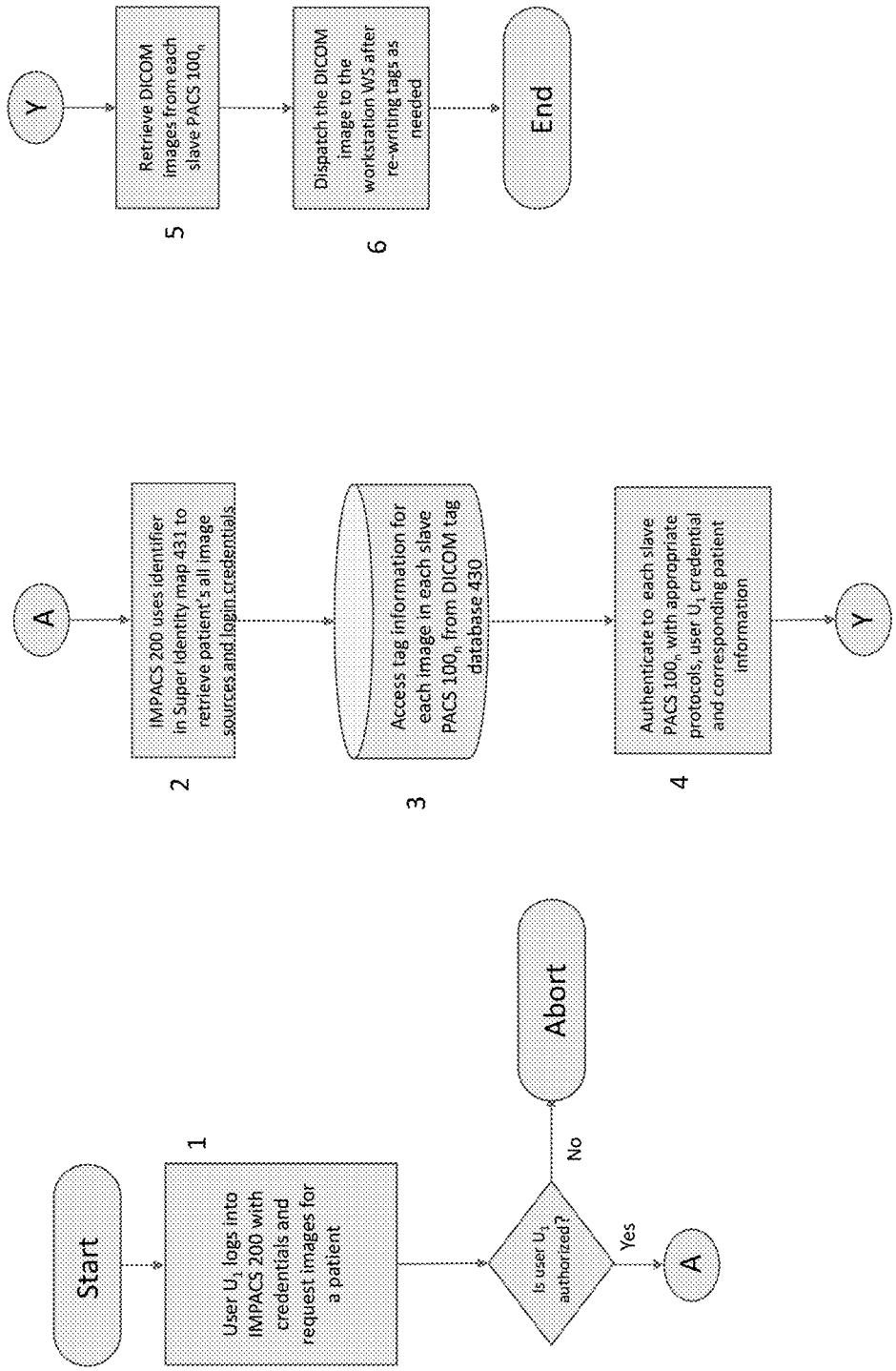
Figure 16: Process For IMPACS System 200 Search with Patient Super-Identity

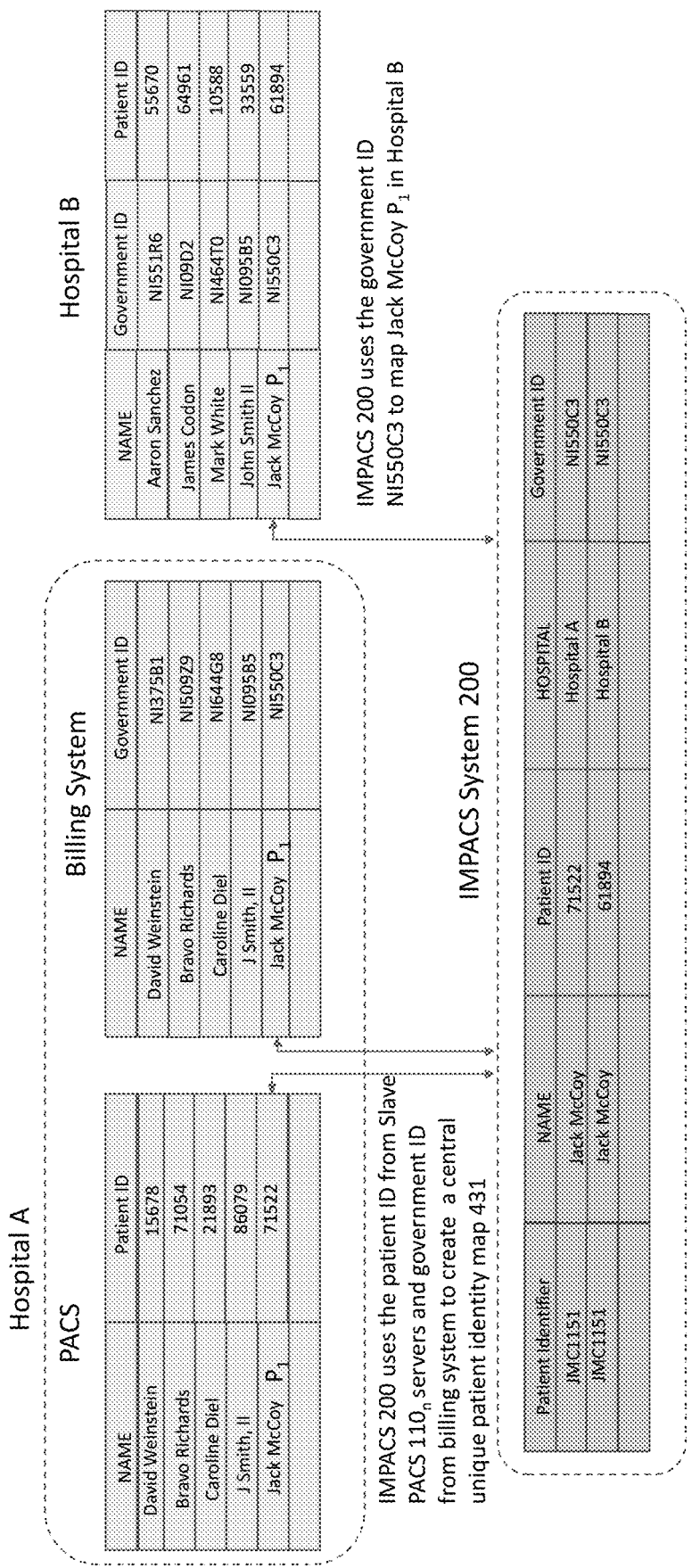
Figure 17: IMPACS System 200 Patient Unification using External Sources

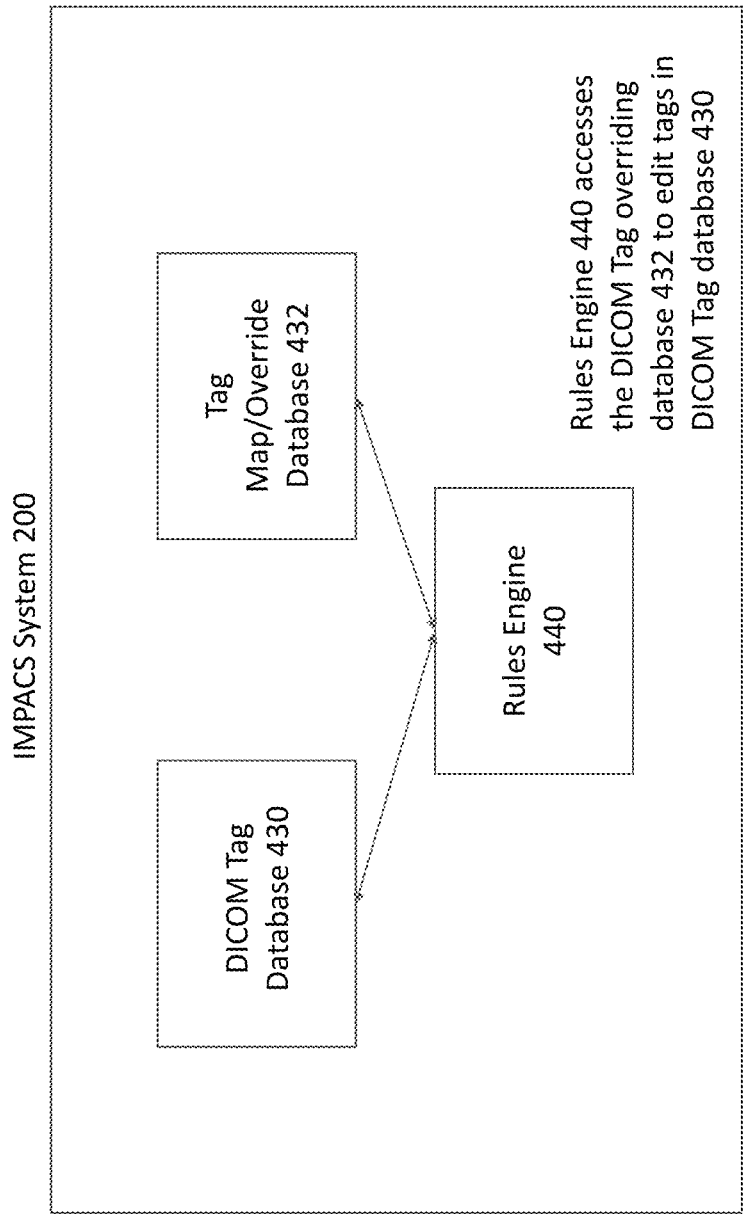
Figure 18: Rules Engine 440

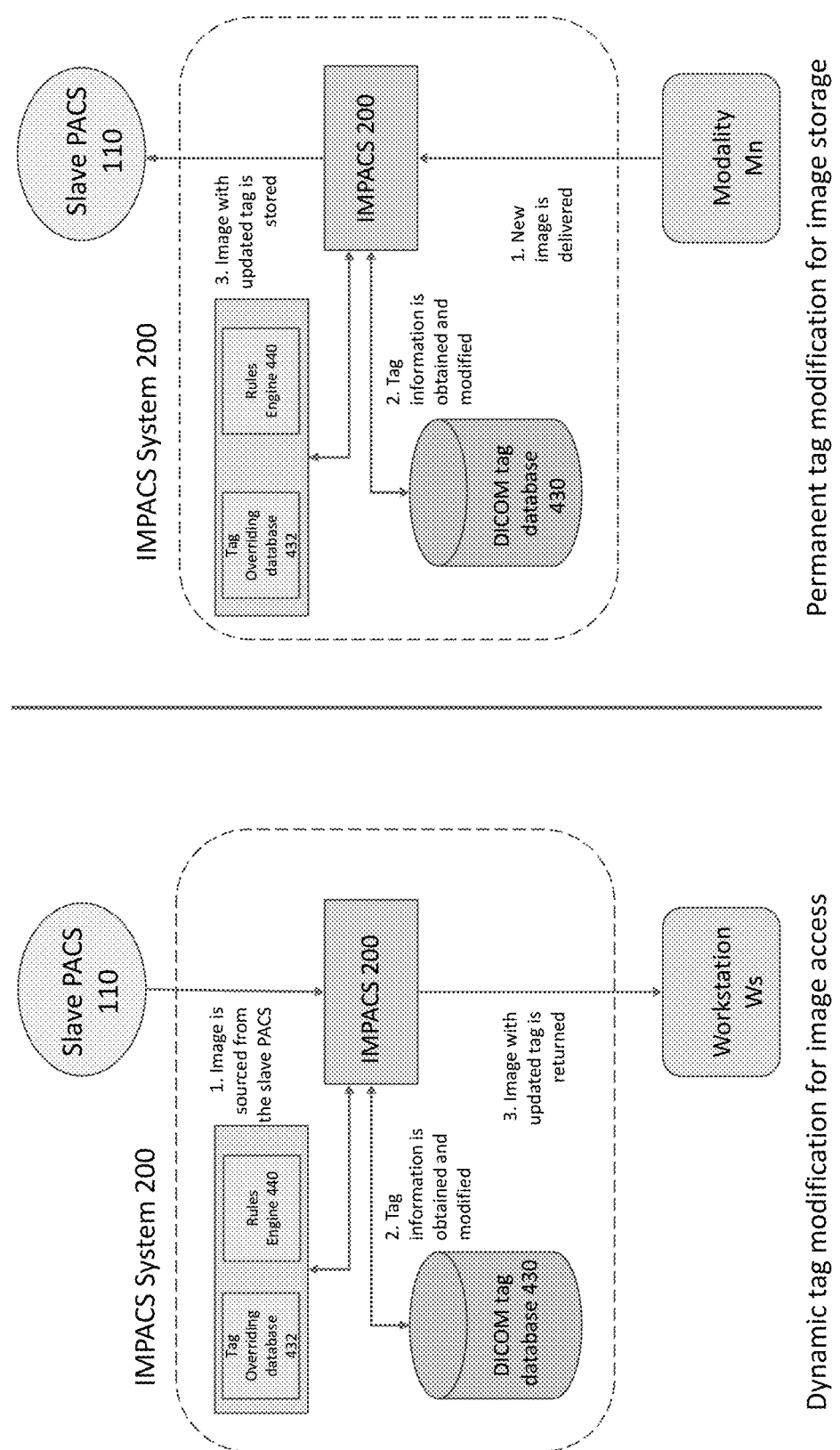
Figure 19: DICOM Tag Modification

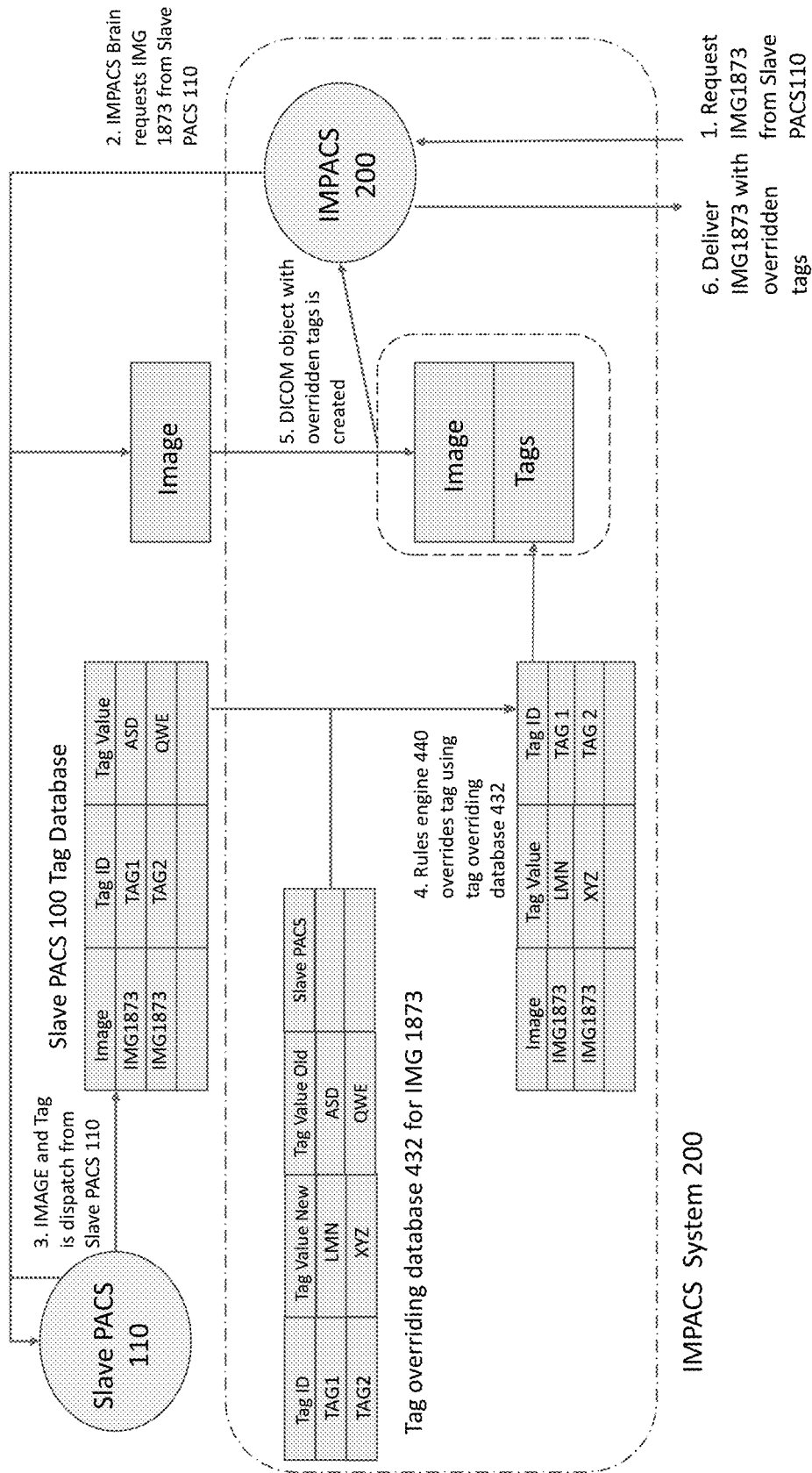
Figure 20: Detailed Example of Overriding Image Tag Values

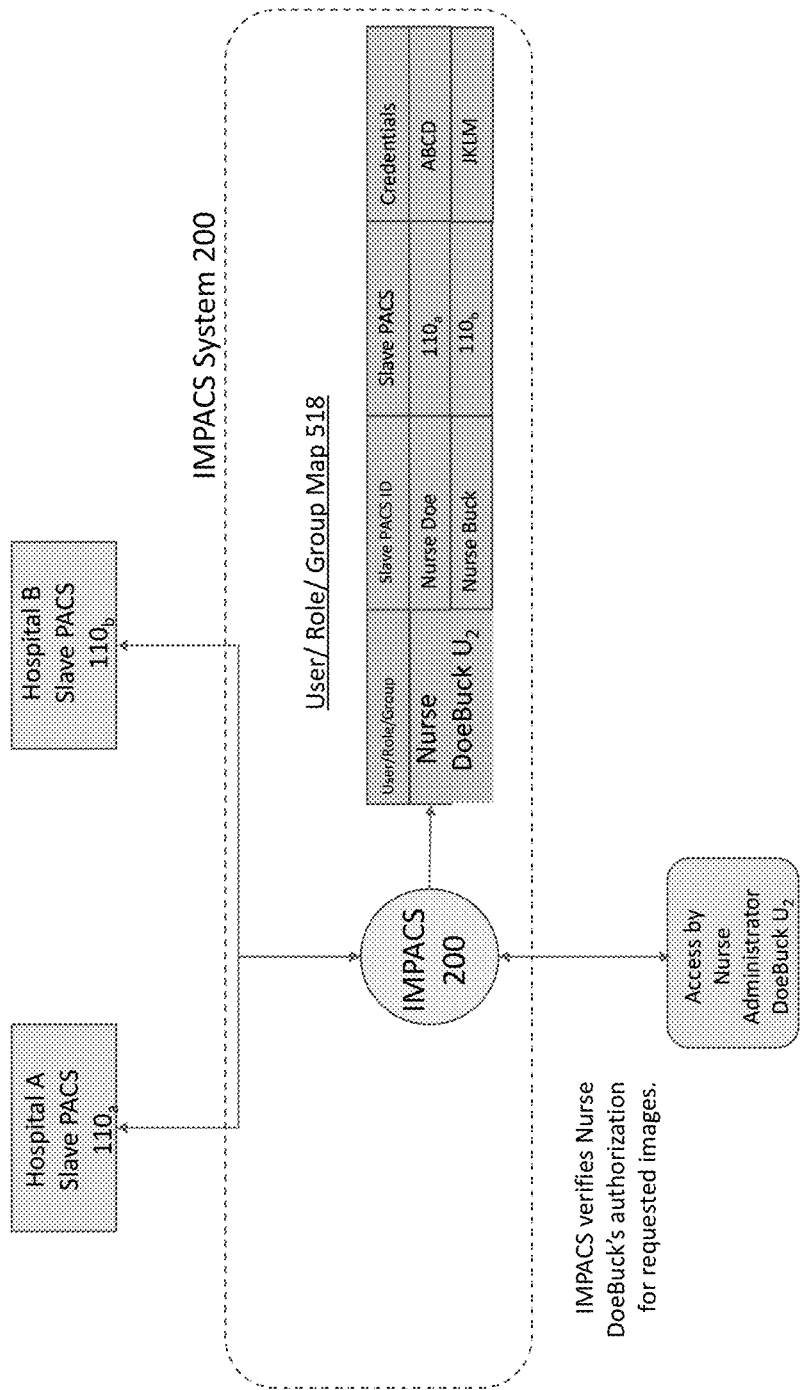
Figure 21: IMPACS User/Role/Group or Client Identity Map

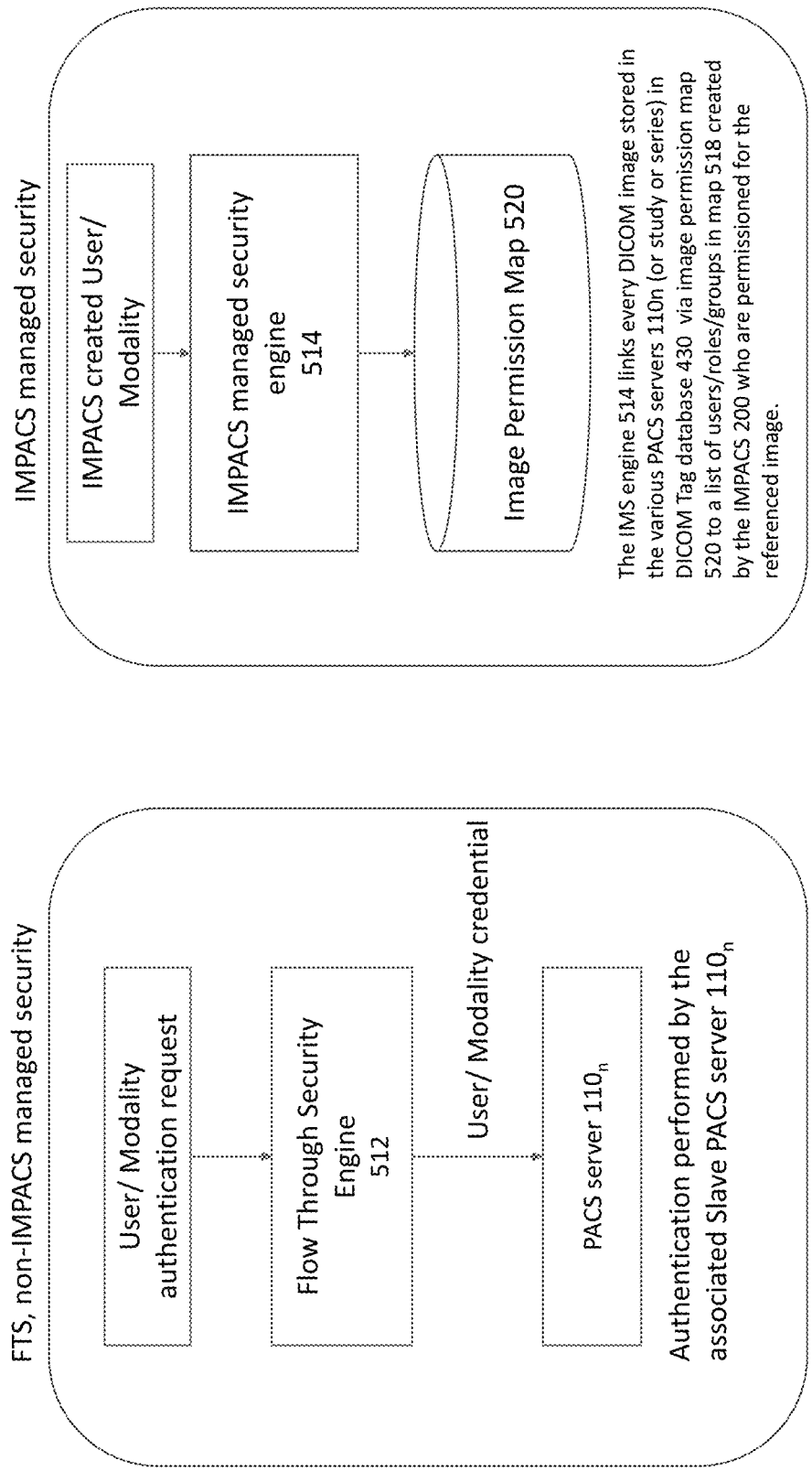
Figure 22: IMPACS System 200 Managed Security Framework

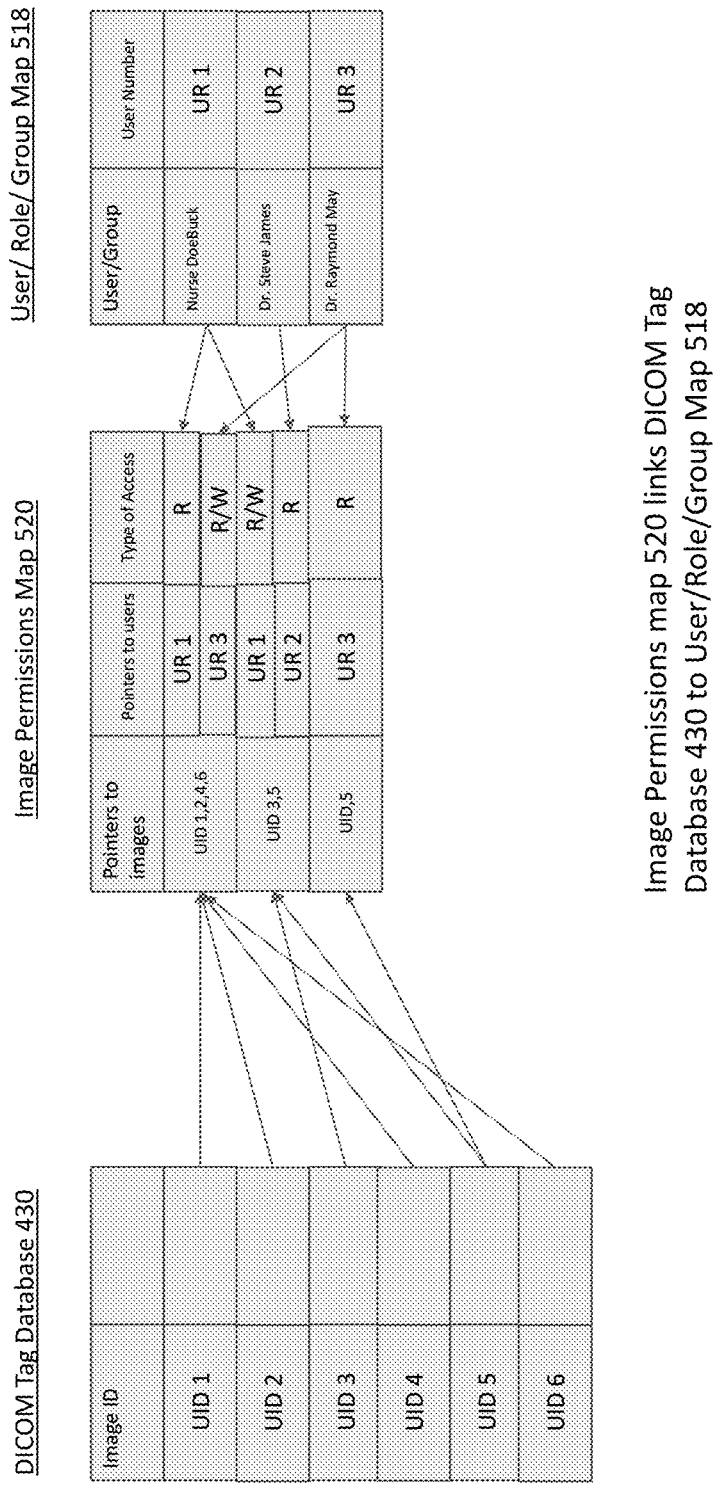
Figure 23: IMPACS Image Permissions Map

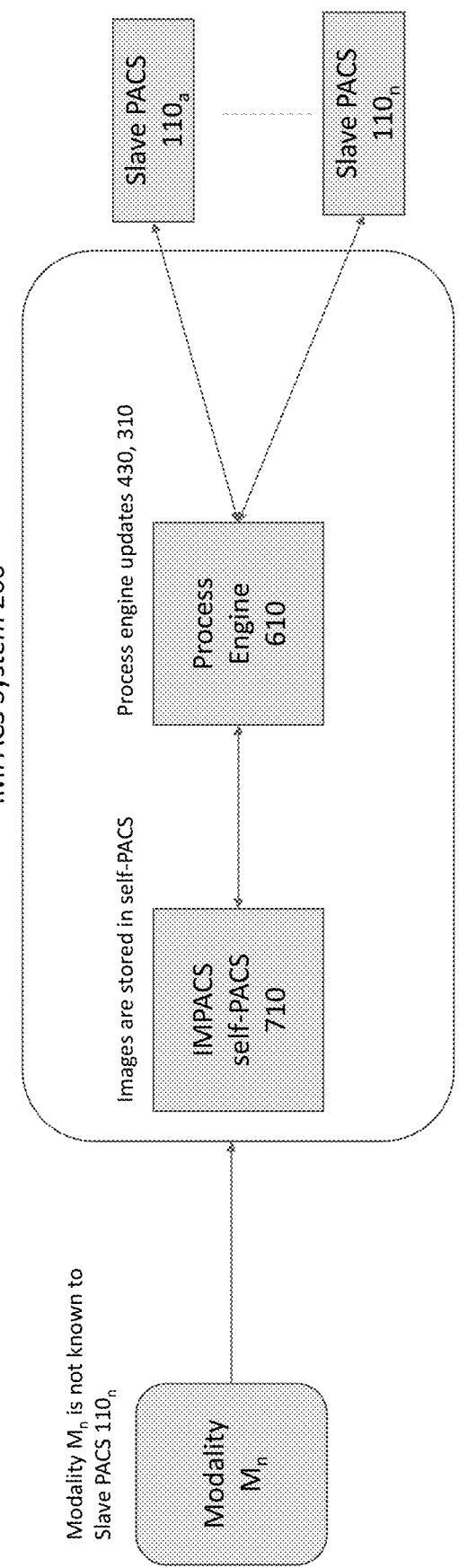
Figure 24: IMPACS System 200 Self-PACS

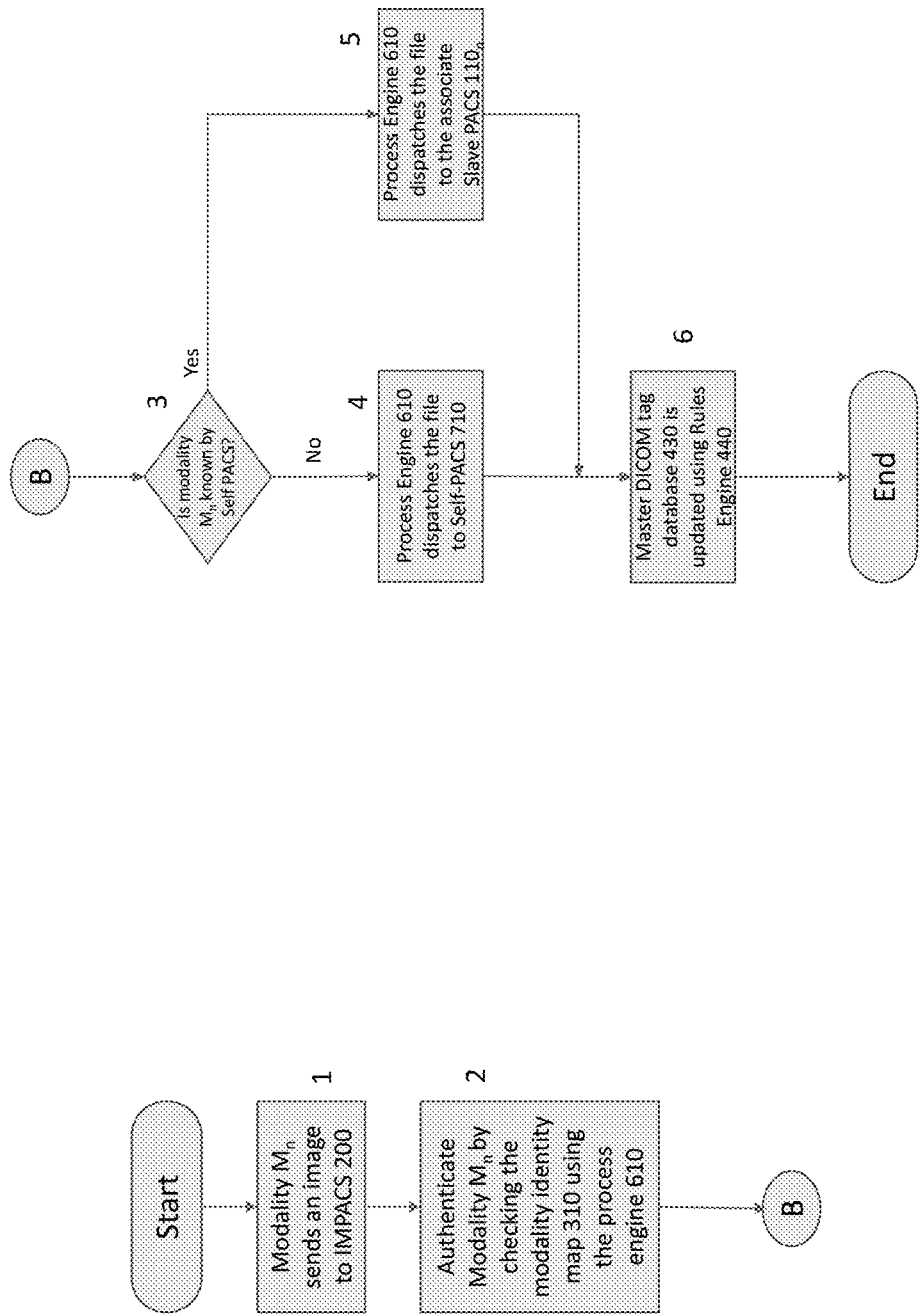
Figure 25: Flowchart for IMPACS System 200 Self-PACS in Use

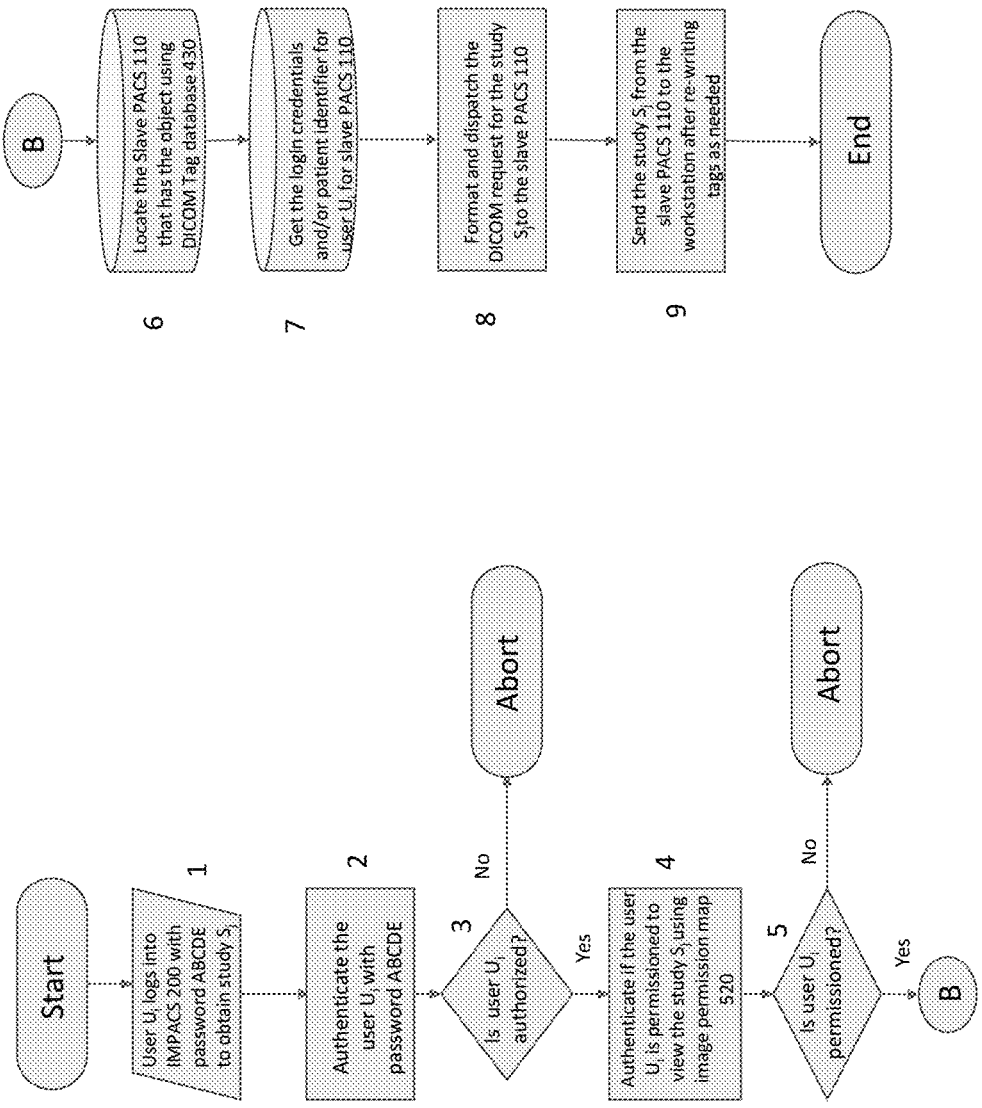
Figure 26: Process of Image Access and Delivery through IMPACS System 200

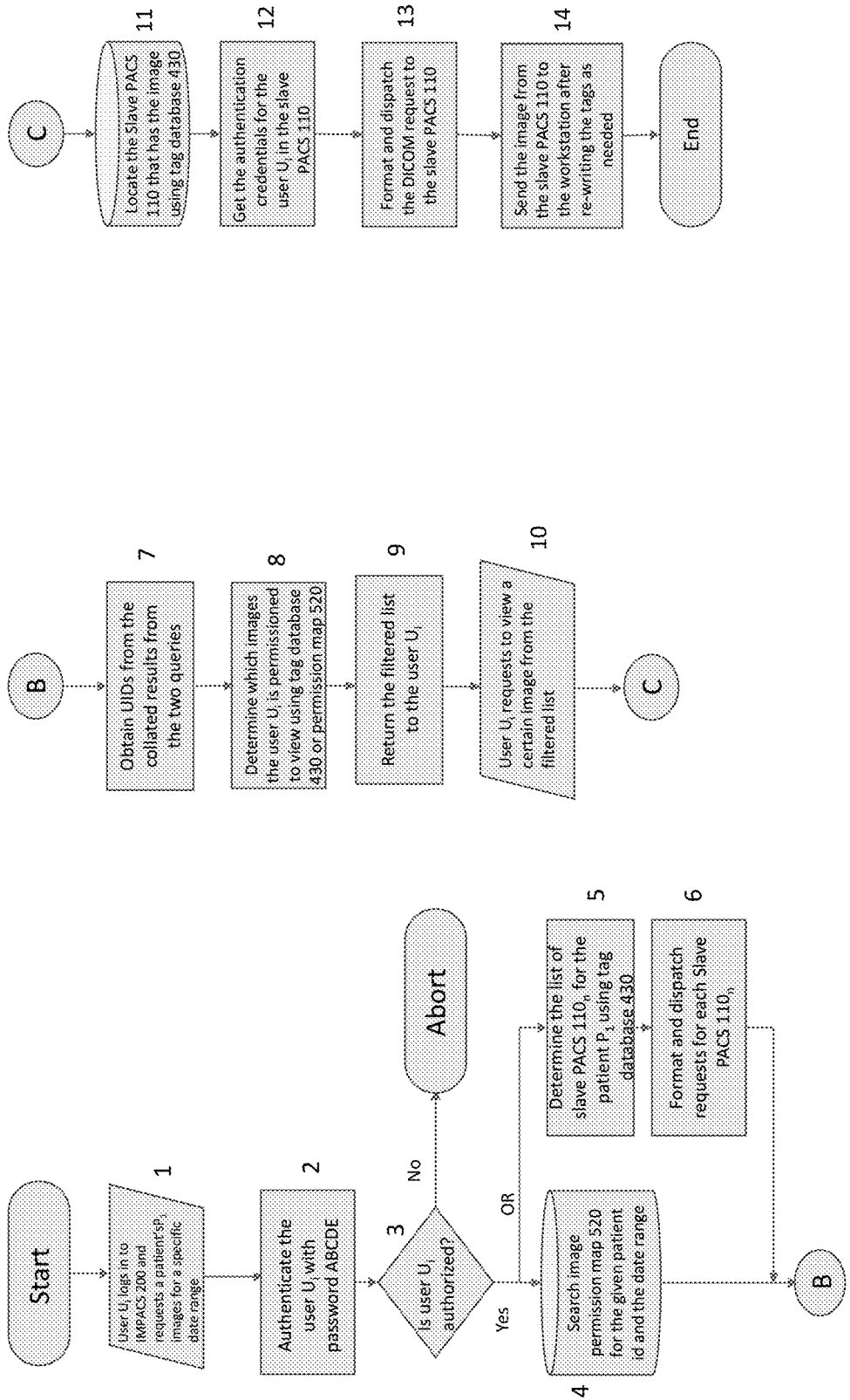
Figure 27: Flowchart for Image Acess and Delivery for a Specific Date Range

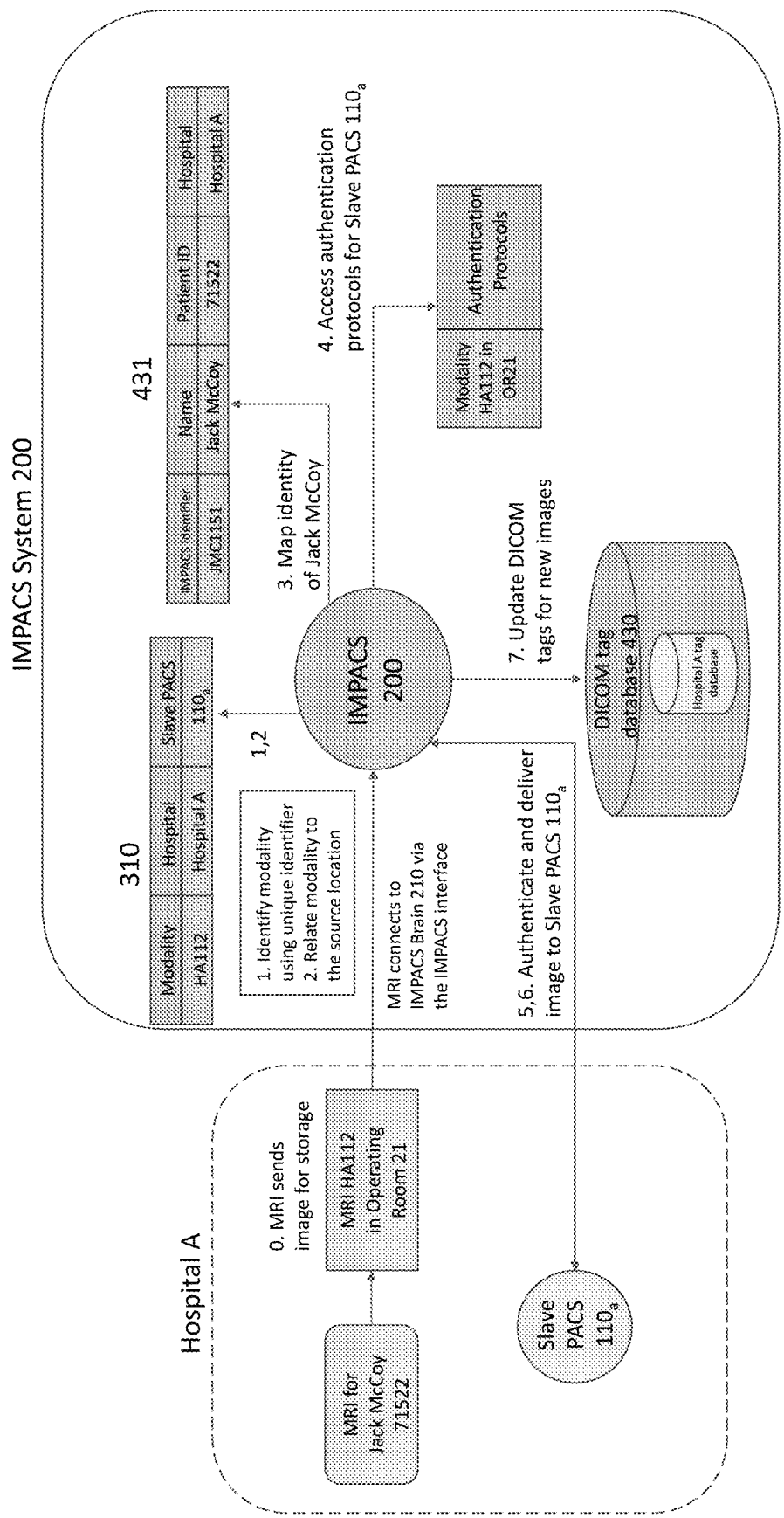
Figure 28: Modality using the IMPACS System 200 in Emulation Mode

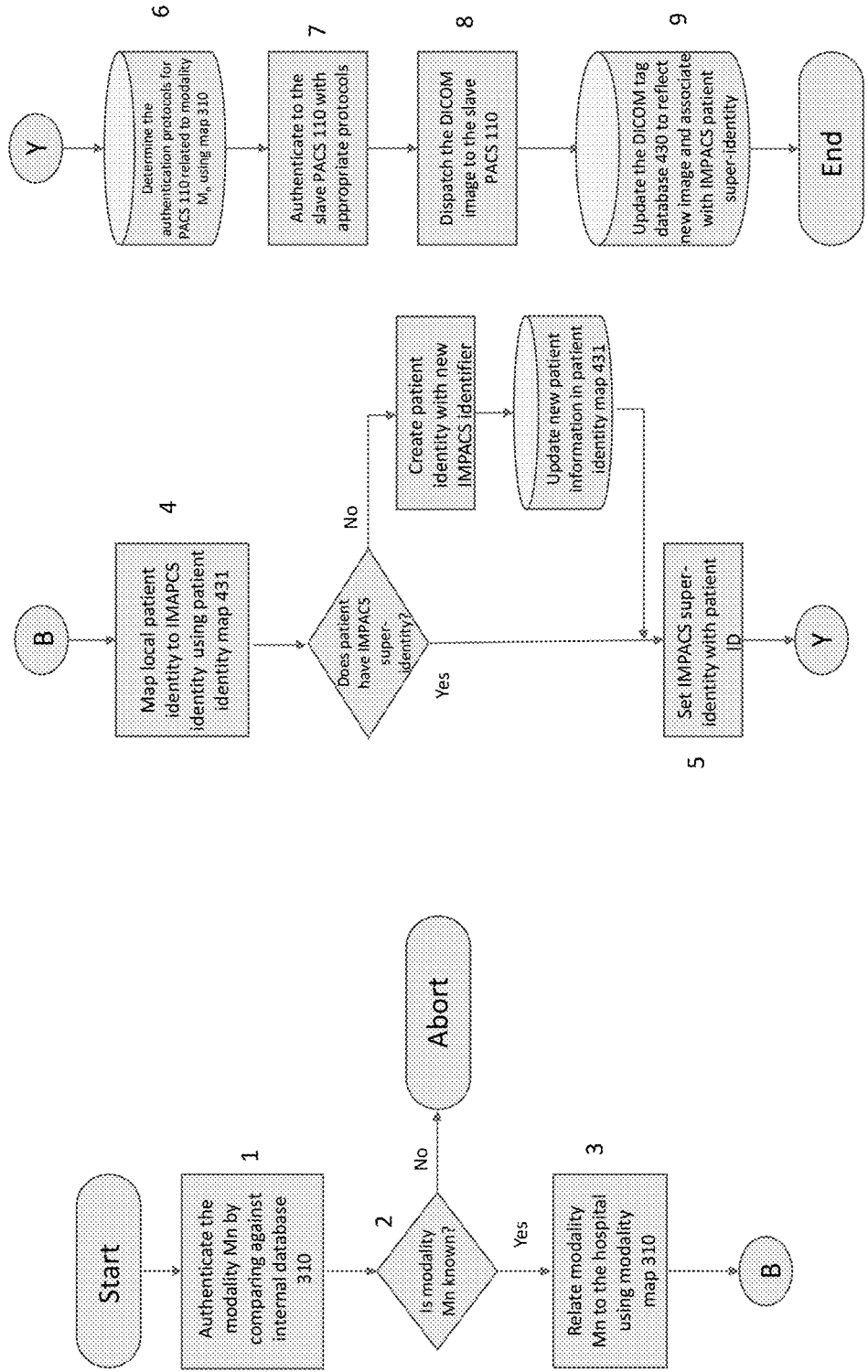
Figure 29: Flowchart for Modality using the IMPACS System 200 in Emulation Mode

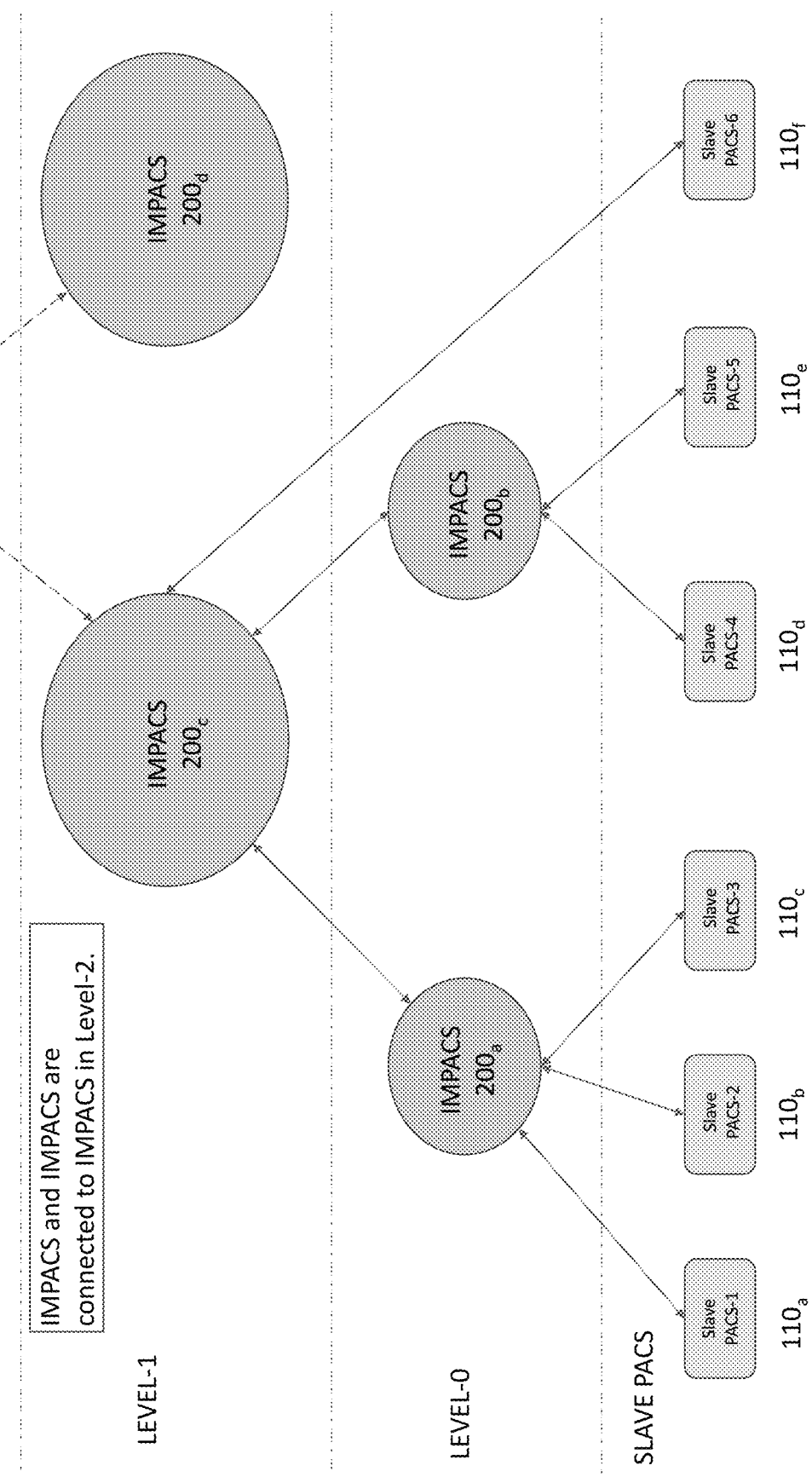
Figure 30: An Example of IMPACS System 200 Hierarchy

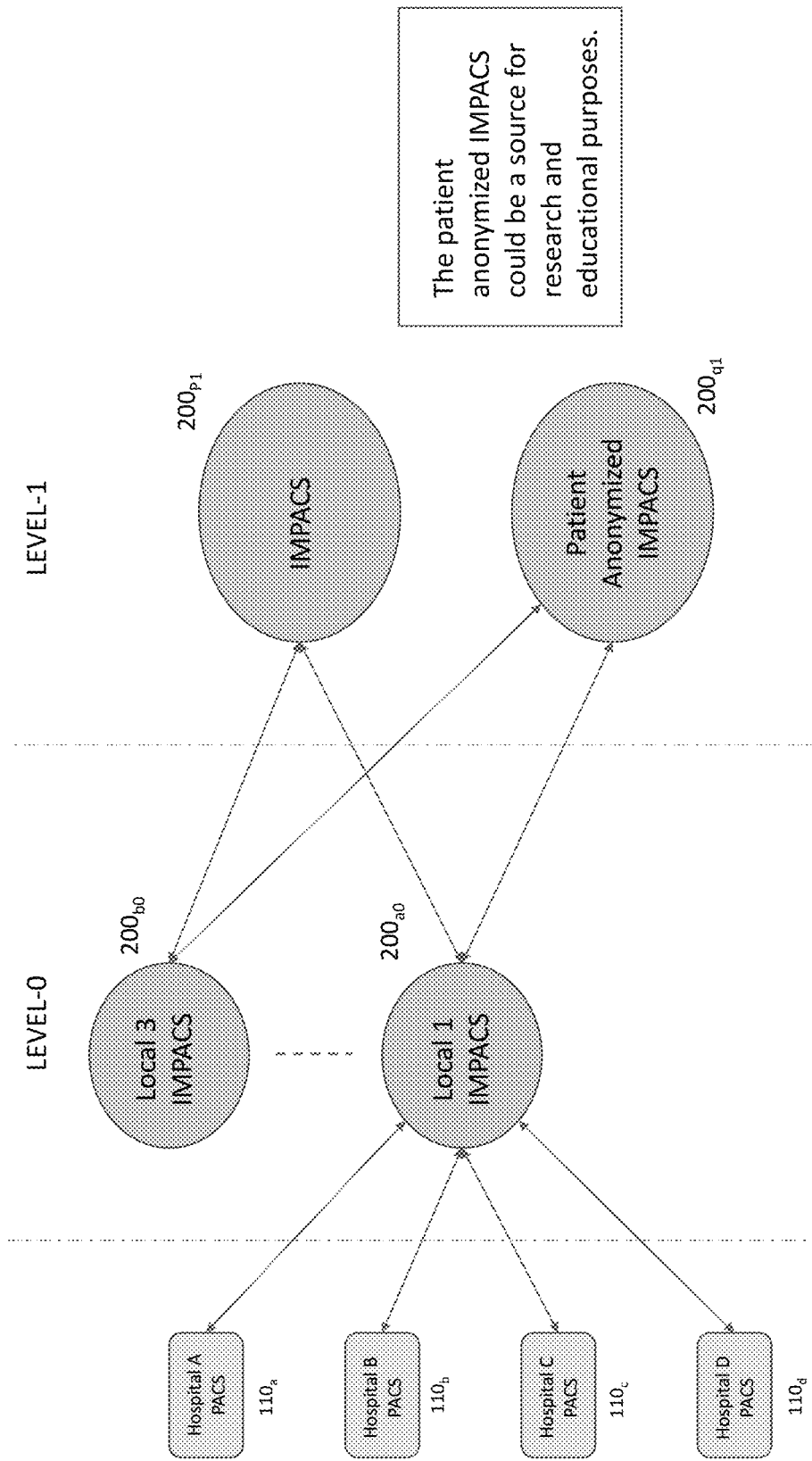
Figure 31: Another Example of IMPACS System 200 Hierarchy

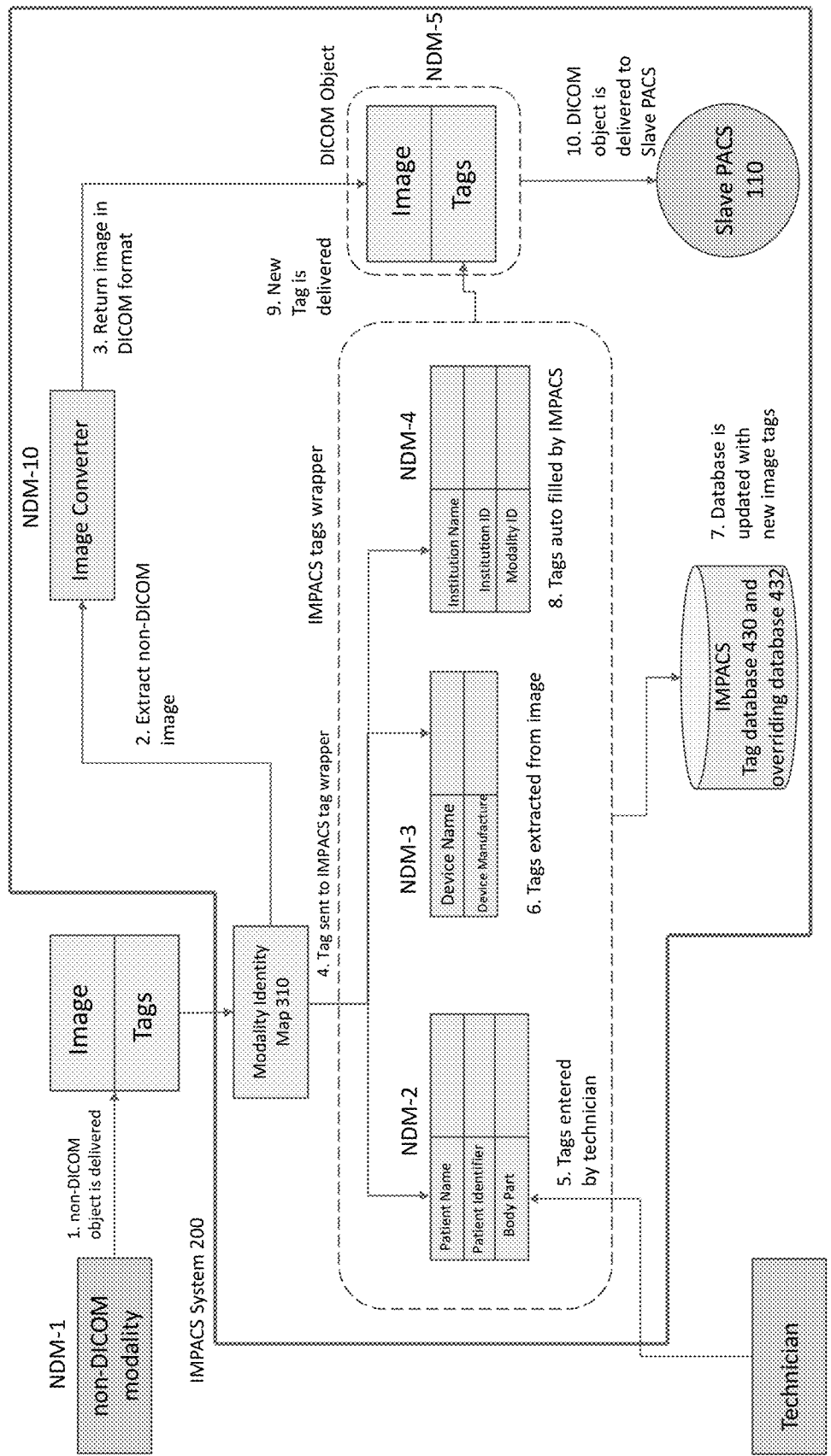
Figure 32: IMPACS System 200 servicing a non-DICOM Modality

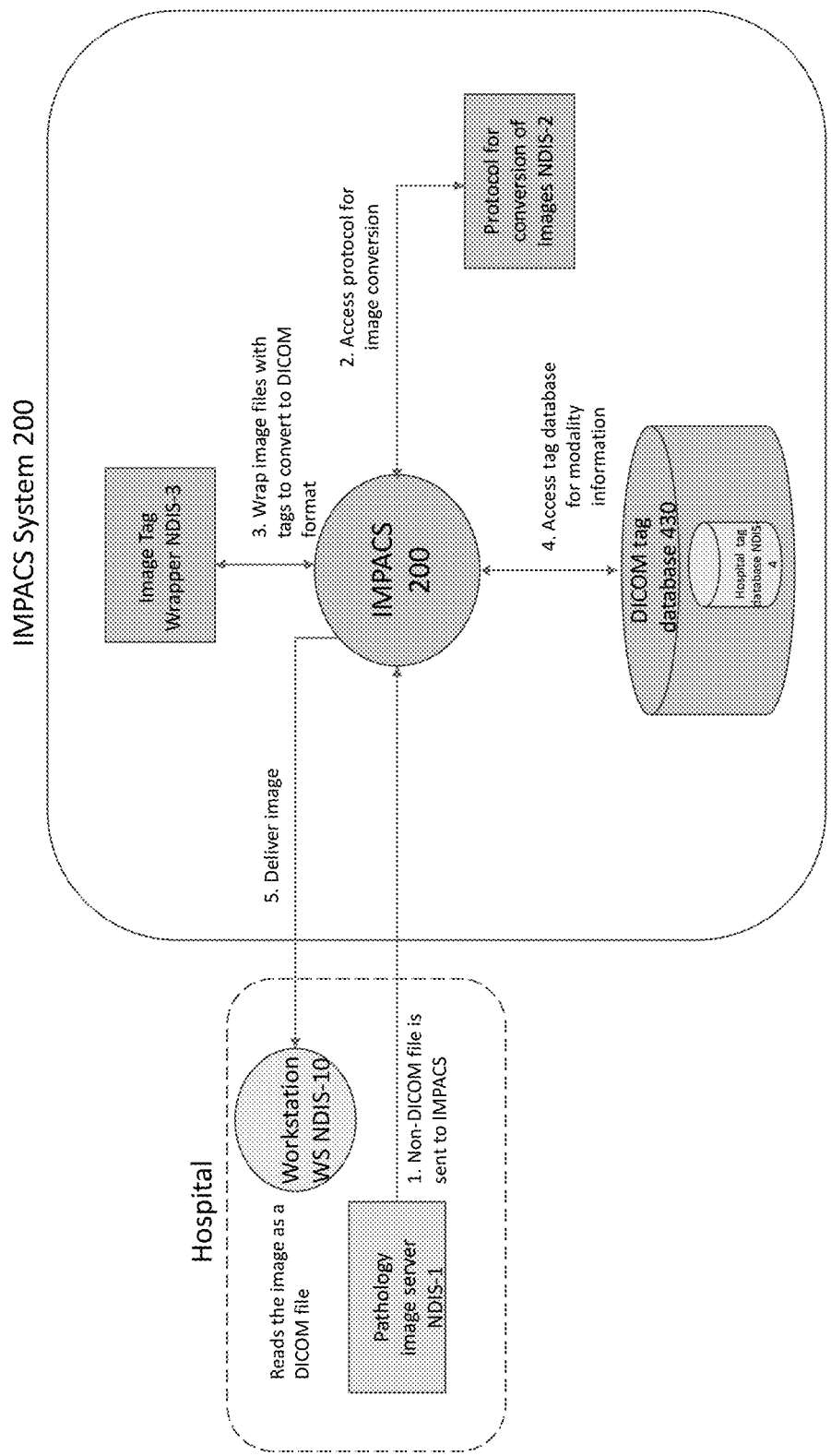
Figure 33: IMPACS System 200 Enabling non-DICOM Image Stores

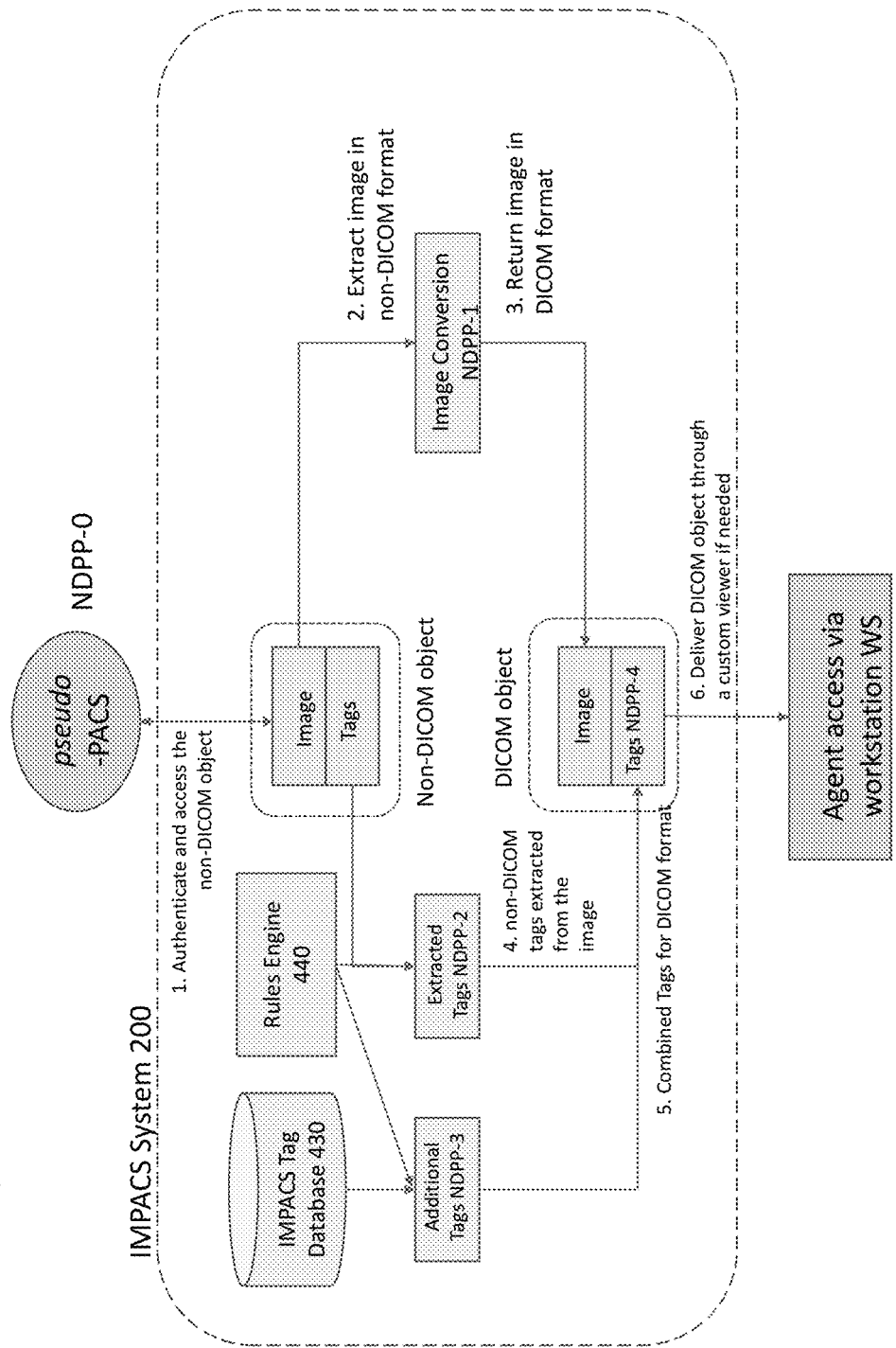
Figure 34: IMPACS System 200 Operating with a non-DICOM pseudoPACS

INTELLIGENT META PACS SYSTEM AND SERVER

1 CROSS-REFERENCE TO RELATED APPLICATION

This application claims the benefit of U.S. provisional patent application Ser. No. 62/981,280, filed on Feb. 25, 2020, entitled Intelligent Meta PACS System and Server, which is incorporated by reference herein in its entirety.

2 FIELD OF INVENTION

The present invention relates to a system and server that improves the coordination, operability, and functionality of an existing Picture Archiving and Communication System (PACS) and its server. The present invention is a specific implementation of the "System for Process Coordination and Interoperability across Different Systems, Platforms and/or Businesses" disclosed in pending patent application Ser. No. 16/037,249 filed on Jul. 17, 2018, which is incorporated by reference herein in its entirety. In particular, this application is an implementation related to medical records in the medical field utilizing the Digital Imaging and Communications in Medicine (DICOM) standard and PACS server.

3 BACKGROUND OF THE INVENTION

3.1 The Digital Imaging and Communications in Medicine (DICOM) Standard

The Digital Imaging and Communications in Medicine ("DICOM") standard is one that was created as a universal framework to deal with all functional aspects of digital medical imaging. The DICOM standard traces its roots back to 1985 when the American College of Radiology (ACR) and the National Electrical Manufacturers Association (NEMA) collaborated to publish the ACR-NEMA Standards Publication No. 300-1985 which laid out a standard method for the transmission of digital medical images and their associated information. The promise of standardization in medical images was not achieved until ACR-NEMA published Version 3 of their standards in 1993 renaming the same to DICOM.

The DICOM standard governs the practical use of digital images in medicine. It deals with image storage, data transfer and image display. As such, DICOM does all of the following:
- it specifies a network protocol for image transmission using TCP/IP.
- it defines the structure for image objects and their associated information as well as creating a mechanism for uniquely identifying such objects when they are acted upon over the network.
- it sets up information groupings for patients, studies, series and other data so as to permit logical organization of the data.
- A full explanation of DICOM can be obtained at: http://dicom.nema.org/dicom/geninfo/Strategy.pdf.

3.2 The Picture Archiving and Communication System (PACS)

The actual implementation of DICOM-based imaging within a medical provider is provided by a Picture Archiving and Communication System (PACS). The PACS is a medical system consisting of all the necessary technology hardware and software to enable the acquisition, storage, retrieval, transmission and display of digital medical images. Put differently, the PACS enables the digital imaging workflow within a provider.

The basic components of a PACS are:
- DICOM-aware image acquisition devices or modalities that actually obtain the medical images and convert them into DICOM format.
- The PACS server which is the computing brain of the PACS. The PACS server provides the short and long-term storage of DICOM images obtained by the modalities. It also manages these images, permits their retrieval and distribution, and makes them available for presentation.
- DICOM-capable workstations which provide interactive display of digital images from the PACS server using software that understands the DICOM formats.

FIG. 1 shows an example of how a prior art DICOM-based PACS 100 is configured within a medical facility. In the rest of the description below, the terms PACS or PACS system are used to refer to a PACS server $110_n$ while specifically referring to the other PACS elements as modalities $M_n$ or workstations $WS_n$. When the term PACS is used to reflect the full PACS 100 as described above, it will generally explicitly indicate as such, though in most such cases the meaning should be obvious from the context.

As shown in FIG. 1, a PACS server 110 interconnects various modalities $M_n$ and workstations $WS_n$ in a medical facility. A department of a medical facility has various modalities $M_n$. The Radiology department may have five modalities—Computed Radiography (CR) $M_1$, Digital Radiography (DX) $M_2$, Computed Tomography (CT) $M_3$, Magnetic Resonance (MR) $M_4$, and Mammography (MG) $M_5$. The Cardiology department may have 3 modalities—X-Ray Angiography (XA) $M_6$, Ultrasound (US) $M_7$, and Electrocardiogram ECG ($M_8$). The Ophthalmology department may have 3 modalities—External-camera Photography (XC) $M_9$, Ophthalmic Photography (OP) $M_{10}$, and Secondary Capture Device (SC) $M_{11}$. The Dermatology and other departments may have 5 modalities—External-camera Photography (XC) $M_{12}$, Other Device (OT) $M_{13}$. Secondary Capture Device (SC) $M_{14}$, SR Document Unit (SR) $M_{15}$, Portable Document Format Scanner (PDF) $M_{16}$.

A medical facility also has various workstations $WS_n$, such as a Workstation $WS_1$ at a nurse station, a personal computer $WS_2$ of a doctor, a laptop $WS_3$ of a radiologist, and a Tablet/Mobile device $WS_4$ of a therapist.

The existence of a PACS server 110 in conjunction with modalities $M_n$ and workstations $W_n$ that all operated with the DICOM standard created remarkable efficiency in the handling of medical images within a medical provider. Prior to DICOM's establishment, providers had to contend either with physical film or with a variety of incompatible digital imaging formats that could not be used across the provider easily, let alone shared with outside facilities. With a PACS server 110 and DICOM-aware modalities $M_n$, providers were able to create a straightforward workflow that permitted efficient use and transfer of medical images. For example, a PACS server 110 with DICOM-aware modalities $M_n$ made the following workflow possible, as shown in FIG. 2:

1. An X-Ray machine $M_1$ that supported DICOM, would take a digital X-Ray of a patient. It would combine this X-Ray image with some additional information required by the DICOM standard such as how the image was taken, the specifications of the device etc. along with some limited information about the patient (such as his birth-date and provider-generated identifier). Much of this information will be generated by the X-Ray machine $M_1$ itself, with the operating technician providing all the data regarding the patient, body part scanned etc.

2. The X-Ray image wrapped with the additional information "tags" so that it is now in DICOM format would be transferred across the network into the provider's central PACS server 110 for storage. This means that the X-Ray machine $M_1$ needs limited local storage, backups etc. all of which would be provided at the PACS server 110 level, either within the PACS server system itself or by other systems controlled by and accessible to the PACS server 110 such as for example a group of computers that make up the PACS server 110's local Storage Area Network.

3. The PACS server 110 would deliver the obtained image to all hospital staff as needed making it available at Workstation $WS_1$ for example, with the X-Ray machine $M_1$ now free to work on other patients and images.

The important thing to note is that the X-Ray machine $M_1$ needs to have only the very limited intelligence needed to support the DICOM standard by wrapping its images with the right tags and being able to network with the PACS server 110. Such intelligence could be added at very low cost to virtually any imaging modality be it a CAT scan machine, an MRI scanner etc., a factor that was particularly important during the early 1990s when computing technology was much more expensive. The advancement of scanning technologies and the development of new modalities do not require any change to the provider workflow—as long as a new machine speaks DICOM, it will interact seamlessly with the central PACS server 110. Many U.S. hospitals have X-Ray machines that are often 20 or more years old because the actual scanning technology for capturing an X-Ray has not changed much over the period. If these machines are DICOM-aware, they still have all the necessary computing intelligence to capture their images and deliver them to the provider PACS server $110_n$ however recent the vintage of the latter might be.

3.3 Limitations of the Prior Art DICOM/PACS Model

The DICOM standard was established at a time when high-speed networking was not widely available even within a single organization, the Internet did not exist and digital memory and storage were scarce and expensive. Most hospitals during this time worked with X-ray, CAT scan and other images in physical form. By creating a robust networking protocol, a centralized storage framework and consistent image tagging, DICOM allowed hospitals to replace their largely analog/physical workflow with digital images, networked imaging hardware and centralized storage. The DICOM standard was a huge step forward where it came to medical imaging and provided most of the functions that are needed within a single hospital for imaging.

In today's world, computer networks are very fast and ubiquitous, networking protocols are robust and digital storage is exceptionally cheap and reliable. DICOM has adapted to some of these changes. Thus, for example, numerous web extensions for DICOM (DicomWeb) collectively allow for DICOM image handling over the Internet using standard Internet protocols. Again, DICOM networking speeds and PACS server storage amounts and image access speeds have all improved significantly with these advances in technology.

However, even with these improvements in implementation and the extensions to the standard engendered by technological change, the DICOM/PACS framework still remains a system that works best within a given medical provider. This is entirely understandable because DICOM was a standard originally devised to address the medical imaging needs of a single provider. Thus, even today, DICOM does not easily permit interoperability across medical providers except to a very limited degree. There are three major issues with the existing DICOM/PACS framework which we take up in the sections below.

3.3.1 Images have Globally Unique Identifiers but Patients do not

The DICOM standard organizes images into a hierarchy of studies, series and instances with one study being made up of one or more series, and with the latter in turn being composed of one or more instances. The standard requires that each study, series and instance have a Globally Unique Identifier (UID) no matter what modality generated the image. Thus, a sequence of X-Ray images obtained on a machine in Hospital A for a specific patient would be grouped into studies, series and instances each of which would have a UID that cannot be repeated either in the same hospital or anywhere else. Were a second group of images to be taken, they would have to be identified with a new (and unique) group of study, series and instance identifiers even if they pertain to the same patient and the same body locations.

The DICOM standards setters have managed to ensure this global uniqueness even with the explosive growth in digital imaging with UIDs working reliably for the most part. Minor issues may arise within a hospital because of specific workflows. Thus, when a hospital edits the images generated by a DICOM modality using a particular software package, the latter has to take the proper care to ensure that these edited images are labeled with new study, series and instances UIDs as appropriate so that they do not conflict with the unique identifiers of the original image. More simply, a correct implementation of the rules established by the standard (which requires new UIDs for edited images) would ensure global uniqueness of the image UIDs in regard to study, series and instance.

There are other problems that might occur even when we have global uniqueness of study, series and instance UIDs. For example, we might have a patient at a provider who has 75 images taken during a single session that should logically be organized into 5 series (of say 15 images each) all consolidated into a single study. However, these images might be coded with each instance corresponding to a unique series and study, so that there are 75 studies and 75 series with each study and series corresponding to a single image instance. Such issues are not uncommon especially when the UID tags are not assigned by the modality itself but by a process that is not aware of the sequence of image acquisition and performs the tagging after the fact.

The patient is a critical part of the imaging process because it is on his/her behalf that the image was obtained in the first place. The DICOM standard requires a patient identifier (PatientID DICOM tag) also known as the Medical Record Number (MRN) to be included as part of the metadata associated with any DICOM image. This PatientID tag is a so-called Type 1 tag that is both required in all DICOM data and must be supported by all DICOM-aware devices. It must identify the patient uniquely within that DICOM/PACS setup. However, the DICOM standard does not fully address the problems faced in patient identification for the following reasons:

Patient Identifiers are not globally unique. The DICOM standard does not require global uniqueness of the patient identifier that is part of the image tag data. The standard insists that a patient identifier within a single PACS system in a hospital or provider network be unique so that all images with a specific patient identifier can be associated to the same patient. However, the standard leaves it up to the provider facility to assign these patient identifiers, so two different facilities may assign identical PatientID tags to two completely different patients.

There is no central authority to assign Patient Identifiers, nor is there any algorithm mandated by the standard for their consistent generation. Each provider is free to assign patient identifiers based on his internal workflow as long as the broad parameters for the PatientID specification (as to length, characters usable etc.) as provided by the DICOM standard are met.

The same patient can have multiple Patient Identifiers. The standard only mandates that a given PatientID be uniquely associated with a single patient within a facility. It does not preclude the same facility however, from assigning multiple PatientID tags to the same patient. Thus, a single facility might often assign patient identifiers based on the modality generating the image or the intended destination of the same. Thus, a given facility that internally labels a patient using an identifier 12312 might generate PatientID tags such as 12312. XRay for a scan coming from an X-Ray machine or 12312. DrSmith for a scan that is to be directed to a Dr. Smith at the facility. These identifiers meet the DICOM requirements in that they all uniquely identify a single patient. However, a single patient even within this one facility now may have multiple PatientID tags for his images.

FIG. 3 considers the problems that arise because patient identifiers are not unique across providers. A patient Jack McCoy $P_1$ in Hospital A is assigned an identifier of 71522 in the single PACS server 110$_a$ that the institution uses. This will mean that all DICOM images with the identifier of 71522 in Hospital A's PACS server 110$_a$ will pertain to the aforesaid Jack $P_1$. However, Hospital B that operates its own PACS server 110$_b$, might have assigned identifier 71522 to patient Jill Johnson $P_2$, so that all images within its organization would pertain to Jill. Combining the sets of images from hospitals A and B would be impossible without a change in the patient identification scheme because the patient identifier 71522 refers to two different patients across these hospital systems. Even though the underlying images for these patients have unique study, series and instance identifiers, these UIDs are not relevant in combining these image sets because the patient data would be incorrect.

Even if the DICOM standard required the patient identifier to be globally unique (which it does not), it would still not be able to combine images easily across Hospitals A and B above, using the PatientID tag. As illustrated in FIG. 4, if identifier 71522 were not permitted in Hospital B after its use in Hospital A, the fact remains that Jack McCoy $P_1$ would have to get a new patient identifier (say 61894) at Hospital B if he were ever to obtain images there. So, even if by making the patient identifier unique to prevent conflict, there is still the problem that identifiers 71522 and 61894 refer to the same patient Jack McCoy $P_1$, and DICOM provides no standard mechanism to deal with this issue. This problem is highlighted because it can typically arise within a single provider when it chooses to assign multiple PatientID tags for a given patient based on the modality acquiring the image or its destination.

Given that patient identities as provided by the PatientID tag might prove problematic, some of the DICOM software available today will often rely on other patient attributes provided in the standard to uniquely identify the patient. Such attributes include the patient's date of birth, his name, sex etc. many of which might be present in the DICOM tag information. However, there is no certainty that all of these tags will even be available. Even something as simple as the patient's name is a Type 2 DICOM tag that can optionally be left blank. Even worse, there could be a multitude of proverbial John Smith patients sharing the same birthday and name making automatic resolution impossible. The DICOM data dictionary provides additional patient data fields known as Other Patient IDs for such eventualities, but does not address what data goes into these fields. As such, each facility (and its associated software) typically uses these fields in a manner dictated by its own workflow and there is no standard mechanism to use this information across facilities.

Thus, the net result is that ensuring interoperability across multiple provider PACS systems is not easily possible with the DICOM standard given the lack of a single, unique patient identifier that applies to a given patient across all providers. In fact, as FIG. 4 shows, even getting all of the images of a single patient correctly within a single provider's PACS system can prove problematic because of the lack of standardization of the method for assigning PatientID tags to a patient in DICOM.

The issues discussed above are taken up in much greater detail in Applicant's pending patent application entitled "System for Process Coordination and Interoperability across Different Systems, Platforms and/or Businesses", Ser. No. 16/037,249 filed on Jul. 17, 2018.

3.3.2 No Standard Security Framework to Control Image Access

The DICOM standard provides a rather rudimentary security framework at best. Its primary security focus is on the definition of protocols for the encryption of images to facilitate their transfer over the network. However, even these limited features are not mandated. This is understandable because the DICOM standard was primarily intended to allow for the simple creation of medical images by in-house modalities and their quick and easy access by authorized medical professionals that were part of the same provider facility. As such, DICOM left overall PACS server 110$_n$ workstation WS$_n$ and modality M$_n$ security to the specific implementation of the PACS 100 and the provider patient record systems it was connected to.

Importantly, DICOM does not provide a standard security framework to deal with which parties have access to the stored medical images and the types of access they might need. Establishing such a framework would have meant understanding the specifics of the various roles and associated workflows within a medical organization, and these elements are not consistent across institutions. Given that DICOM's aim was to establish a standard for the creation, central storage and use of images, the lack of a mandated security framework likely encouraged the proliferation of the standard PACS implementations 100 (encompassing the server(s) 110$_n$ modalities M$_n$ and workstations WS$_n$) support user authentication and security roles using a variety of mechanisms. Some for example, allow the underlying operating or file system to deal with user security and roles. Yet others rely on directory servers such as those that use the Lightweight Directory Access Protocol (LDAP) to support roles and security. In larger hospitals the overall PACS framework 100 is often part of a more comprehensive workflow system engineered by Cerner or Epic Systems that manages the roles and the image access.

Most prior art PACS setups 100 (including the servers $110_n$, modalities $M_n$ and workstations $WS_n$) in use within organizations do not support granular image access across providers, patients, researchers, payers and other external parties. Such a security framework for interoperability, while technically possible, is not feasible in the context of a hospital's PACS server 110 simply because the security bolt-ons needed to enable such functionality are likely to be more complex than the PACS server 110 itself. As such, most patients who need their scans from an imaging facility typically have to contend with a DVD-ROM (or other physical store) of images that they can take to a new provider as needed. A few cloud-based services that have emerged recently also permit the upload of images by the patient or hospital to a website. The images can then be viewed by authorized parties that are given access to this website. These services, which provide more sophisticated management of roles and security, inevitably require copying of the images to their central web servers.

In sum then, the DICOM standard does not provide or mandate granular security features to support use of images from a PACS server 110 across multiple participants outside the provider organization. The provider's Electronic Medical Record (EMR) systems (of which the PACS 110 is a part) might provide such a capability, but there is no standard security framework required or available across EMRs to permit seamless interoperability.

3.3.3 Distributed Storage without Full Interoperability

The DICOM standard does support distributed storage of images albeit to a limited degree. When there is a single PACS server 110 that provides all the patient identifiers and the controlling logic for all image storage, it can store the actual DICOM files in a variety of local and/or remote storage locations, some of which might be PACS servers $110_n$ themselves. This setup is however virtually identical to having a single PACS server 110—the storage details are not relevant to the modalities $M_n$ or the workstations $WS_n$ using this PACS server 110. The DICOM standard also defines protocols to allow PACS servers $110_n$ to request data from other, independent PACS servers $110_n$ that they are connected to, providing thus a form of interoperability. However, this setup cannot provide full interoperability because it faces a host of problems:

The Patient Identity is not standardized across the PACS servers $110_a$ and $110_b$ as illustrated in FIG. 3. So, if the images of a patient Jack McCoy $P_1$ with PACS identifier 71522 are requested, only the images pertaining to 71522 will be returned. But if one of the PACS servers $110_b$ connected to the network has Jill Johnson $P_2$ identified by 71522 as well, then it is not clear which images should be served up for the request. And what if Jack McCoy $P_1$ is identified in one of the servers $110_b$ as 61894 as illustrated in FIG. 4? These images for Jack McCoy will not be returned at all, even though these images pertain to him.

No server in the framework has full knowledge of where all the images are and their details. As such, while one can query a single PACS server 110 for an image it contains, querying across all of them is not something that can be done easily if at all.

Put differently, the DICOM distributed storage framework supports storing and recovering data from various locations assuming the user knows already where the images are and how to search for them. To search for the image, the user will need to know either the unique UID for the image study/series/instance or alternatively, be able to determine the correct PatientID for the patient assigned by the particular institution within which the PACS server 110 resides. For the proverbial patient John Smith, this task becomes virtually impossible.

Thus, the distributed DICOM setup is more akin to connecting to many PACS servers $110_n$ from a single console interface rather than viewing all the images logically organized as though they come from a single PACS server 110. Of course, to do this, the PACS server 110 itself needs to be aware of every other PACS server $110_n$ where the images might be resident.

3.3.4 Summary of Limitations of Prior Art DICOM/PACS

The DICOM standard for medical imaging was set up to permit the storage and use of digital images obtained by a variety of modalities $M_n$ or source machines within a medical provider. The PACS server 110 is the primary digital store for DICOM images within a provider. While the DICOM/PACS framework 100 works exceptionally well within a medical provider, it was never designed for interoperability across hospitals or providers. Importantly, certain data such the patient identifier tags within a DICOM image are not unique across providers. This means that two completely different patients can have the same patient identifiers across different PACS systems 100, even as a single patient may have multiple identifiers across these systems. Thus, combining patients' information/data across PACS systems $100_n$ (and their associated PACS servers $110_n$) based on their identifiers will fail in general. Again, other DICOM tag data may vary across providers depending on their particular workflow. These variations could be both in terms of the specific tag values as well as the fields used for storing such values. Thus, combining images from multiple PACS servers $110_n$ could often result in inconsistent tags across images making searching across them much more difficult.

Given the non-uniqueness of the patient identifiers, ensuring simple access to a given patient's images across all imaging providers requires either that the PACS 110 overwrites the images with new patient identifiers or copies the images to a central location while overwriting them. Attempting to standardize variations in tagging information also requires overwriting the image files in some fashion. Overwriting all the image files in a PACS server $110_n$ is a complex process and is not something that can be done easily, if at all, without significant down-time at the imaging facility. If this process is done incorrectly and without the proper testing, the provider could face significant legal and compliance issues especially if the PACS server's 110 images are rendered inconsistent or unusable. Copying the images before such modification might allow parallel testing, but will greatly increase the storage and backup needs of the organization because medical images take up the lion's share of digital storage in any provider.

While there have been attempts to overcome these deficiencies on interoperability of the prior art PACS systems, proposed solutions have been limited to peer-to-peer approaches, which result in even more complexity as the number of transacting peers increases. Such prior art attempts could not be easily implementable nor provide a scalable solution. Therefore, there is a need for a system and server that simplifies coordination, interoperability, and functionality of PACS systems.

4 SUMMARY OF THE INVENTION

The present invention is a system and server that improves the coordination, operability, and functionality of a PACS system 100 and its associated PACS server 110ₙ that utilizes the DICOM standard. The system of the present invention, which shall be referred to as the Intelligent Meta PACS (IMPACS) system 200, is a powerful and lightweight system and approach to combining medical images stored in a variety of PACS systems 100, within their associated PACS servers 110ₙ (which we will refer to as Slave PACS servers 110ₙ) so that they can be viewed and accessed as though they are on a single PACS system 100/server 110 which is the IMPACS itself.

The IMPACS system 200 is essentially a powerful and extensible process "brain" (i.e a control engine) 201 adapted to work with medical imaging workflows, that can interface to other DICOM entities through a PACS server interface 210, exactly like a standard, prior-art PACS server 110. The IMPACS 200 can connect to and serve as the Master controller for a group of disparate Slave PACS servers 110ₙ and make their images available through its own PACS server interface 210. To entities that access images through the IMPACS system 200, it appears as though the images were resident on the IMPACS system 200 itself even though they are not. Since the IMPACS system 200 does not store the actual images but focuses on making images from its slave PACS servers 110ₙ available for use, it is effectively a "meta" PACS server.

FIG. 5 provides a graphic overview of the IMPACS system 200.

The IMPACS system 200 provides its functionality without modifying the original images in any Slave PACS server 110 connected to it. Since it does not require overwriting of existing images, it is much less risky to implement. To provide its functions, it copies only some tag information about the images stored and does not make copies of the typically very large images and thus does not have to deal with replicated image storage, huge backups and other such issues. It also deals seamlessly with problems that arise in combining images because of the existence of conflicting or repeated patient identifiers across PACS servers 110ₙ in different facilities, and allows proper groupings of images by patient across all of its slave PACS servers 110ₙ. In addition, the IMPACS 200 can fix missing or inconsistent image tags across the various PACS servers 110ₙ associated with it on the fly, and make sorting and searching across them much easier.

Since the IMPACS system 200 of the present invention interfaces to connected DICOM entities (such as modalities Mₙ, workstations WSₙ and other PACS servers 110) which are not its slaves) as a regular PACS server 110 would, it can also be included as a slave PACS server 110 within another IMPACS system 200. This means that groups of PACS servers 110ₙ can be incrementally combined into an IMPACS server hierarchy as needed.

The central brain/control engine 201 of the IMPACS system 200 of the present invention represents little overhead beyond a standard PACS server 110 but can provide considerably more functionality than any prior-art PACS server 110. On initial deployment the IMPACS system 200 can provide almost the same performance as its underlying slave PACS servers 110ₙ, and possibly perform even better because its brain/control engine 201 can offload all the tag searches from the underlying slave PACS servers 110ₙ. Over time, the IMPACS system 200 can analyze image access and use techniques such as caching of images, tag database partitioning, replication or other such methods to dramatically improve performance relative to any standard PACS server 110.

Also, the IMPACS system 200 can work with images stored in a non-PACS system (such as might exist for pathology slides for example) and provide a PACS interface to the latter for certain connected DICOM entities such as workstations without modifying the actual storage framework. Again, it can work with non-DICOM image acquisition devices and convert and tag their images when possible into legal DICOM format for storage in one of its slave PACS servers 110 effectively converting such devices into DICOM "modalities". Finally, the IMPACS brain/control engine 201 controls and logs every image access in the system by every connected entity, and as such can provide robust and granular security for image access.

The IMPACS system 200 of the present invention is a unique, low-cost and non-disruptive technology that solves the pressing need for patient image sharing across medical providers and other participants that need access to images in the medical process. The IMPACS system 200 overcomes the prior art limitations by providing unique identifiers not just for each DICOM image as mandated by the standard, but also for each patient, a universal security framework to control image access, and facilitates distributed image storage while improving accessibility. And it performs all these functions without destructively overwriting any of the existing image tags or data in its network of connected Slave PACS servers 110ₙ.

5 BRIEF DESCRIPTION OF THE DRAWINGS

Preferred embodiments of the present invention have been chosen for purposes of illustration and description and are shown in the accompanying drawings forming a part of the specification wherein:

FIG. 1 is an example of a prior art Picture Archiving and Communication System ("PACS") set up in a medical facility;

FIG. 2 is an example of a workflow for DICOM-aware modalities in a prior art PACS;

FIG. 3 illustrates the prior art problem of patient unification due to non-unique patient identifiers;

FIG. 4 illustrates the prior art problem of patient unification even with unique patient identifiers because of the same patient possessing multiple identifiers;

FIG. 5 provides an overview of the IMPACS system 200 including its brain/control engine and PACS server interface;

FIG. 6 is a functional view that shows the different function groups or layers of the IMPACS system 200 of the present invention;

FIG. 7 is an overview of the IMPACS system 200's emulation layer 300;

FIG. 8 is an overview of the IMPACS system's unification layer 400;

FIG. 9 illustrates the main implementation areas or elements of the IMPACS system 200;

FIG. 10 is an overview of the IMPACS system's interaction with slave PACS servers using different security protocols;

FIG. 11 illustrates the emulation layer of the IMPACS system 200 for modalities using a modality identity map 310;

FIG. 12 illustrates the emulation layer 300 of the IMPACS system 200 using a work station map 320;

FIG. 13 is an overview of the Master DICOM tag database 430 of the IMPACS system;

FIG. 14 is an overview of the setup of the patient super-identity map 431 of the IMPACS system;

FIG. 15 is an overview of searching for images in the IMPACS system 200 with a patient super-identity;

FIG. 16 is a flowchart for the process of searching for images with a patient super-identity in the IMPACS system 200;

FIG. 17 is an overview of the IMPACS system's use of external sources for the patient super-identity map 431 to make patient unification possible;

FIG. 18 shows the IMPACS system 200's Rules Engine 440 and its role in DICOM tag modification;

FIG. 19 illustrates DICOM tag modification;

FIG. 20 provides more detail on DICOM tag modification showing specific databases accessed by the Rules Engine 440 for the same;

FIG. 21 illustrates the user/role/group or client identity map of the IMPACS system;

FIG. 22 illustrates the security frameworks of the IMPACS system;

FIG. 23 illustrates the image permissions map of the IMPACS system;

FIGS. 24 and 25 show the role of the Self-PACS 710 in the IMPACS system 200;

FIGS. 26 and 27 are flowcharts that detail the process of image access and delivery through the IMPACS system for a specific patient and for a given date range respectively;

FIG. 28 illustrates a modality using the IMPACS system in emulation mode;

FIG. 29 is a flowchart that shows the process for a modality using the IMPACS system in emulation mode;

FIG. 30 and FIG. 31 are illustrations of IMPACS system 200 hierarchies;

FIG. 32 illustrates the IMPACS system 200 servicing a non-DICOM modality;

FIG. 33 illustrates the IMPACS system enabling non-DICOM image stores;

FIG. 34 provides an overview of the delivery of images from a non-DICOM image store or pseudoPACS 810;

6 DETAILED DESCRIPTION OF THE PREFERRED EMBODIMENTS

The Intelligent Meta PACS (IMPACS) system 200 of the present invention is essentially a process brain that is designed to work with the medical imaging process flow while interfacing with connected DICOM entities as a regular prior art PACS server 110 would. The existence of the process brain/control engine in the IMPACS 200 allows it to address the limitations of DICOM where it comes to interoperability as discussed above and other deficiencies in the prior art PACS systems.

The IMPACS system 200 is designed to manage the flow of images from a group of connected, disparate "Slave" PACS servers $110_n$ to DICOM entities (such as users $U_n$, workstations $WS_n$, other external PACS servers $110_n$ or modalities $M_n$) that connect to the IMPACS system 200 as clients. The IMPACS system 200 serves as the Master Controller for its group of connected Slave PACS servers $110_n$ and controls all access and image delivery for them when these functions are requested by clients connected to the IMPACS system 200.

The IMPACS system 200 is a combination of two main elements:

A powerful and extensible central process "brain"/control engine 201 that is designed to work with medical images and can be adapted to handle any reasonable imaging workflow across providers, patients, insurers and other participants. This control engine is relatively lightweight and provides the controlling logic for dealing with images, maintaining all the needed data and mappings needed for the same.

A standard PACS server interface 210 through which the control engine 201 interacts with connected DICOM entities such as modalities $M_n$, users $U_n$, workstations $WS_n$ and other PACS servers $110_n$ that are not its slaves. Despite its PACS server interface 210, the IMPACS system 200 is unlike any prior art PACS server 110 in that its primary focus is not on storing images but rather to make it possible for one to access images on other PACS servers $110_n$ connected to the IMPACS system 200 as Slaves as though they were resident on the IMPACS system 200 itself. It is in this respect that the IMPACS system 200 is a "meta" PACS.

Each connected client, connects to the IMPACS system 200 through its PACS server interface 210 that behaves in all respects like a standard PACS server 110. However, the existence of the process brain/control engine 201 allows the IMPACS system 200 to deliver a level of functionality that is simply not possible through any prior art PACS server 110. In particular, the IMPACS system 200 permits the sharing of image data resident across multiple PACS servers $110_n$ while seamlessly handling the problems inherent in such interoperability such as inconsistent patient identifiers, non-standard security etc. as discussed at length above. Importantly, the IMPACS system 200 hides all these issues of DICOM interoperability from its various participants making it possible for them to use the images from a variety of sources without having to deal with the logistical issues that they might otherwise have to face with prior-art PACS systems 100 and servers 110.

FIG. 5 provides a graphic overview of the IMPACS system 200.

The IMPACS system 200 provides numerous functions and features that can be divided into functional groupings or layers (as illustrated in FIG. 6) which are:

Emulation Layer 300. The IMPACS system 200 can emulate each of the underlying slave PACS servers $110_n$ for individual clients/workstations $WS_n$ and modalities $M_n$ connected to it that expect to work with only a specific (slave) PACS server 110.

Unification Layer 400. The IMPACS system 200 can unify the data that is resident in all of its slave PACS servers $110_n$ so that they all appear to reside on the IMPACS system 200 itself. This unification will be virtual in that it will be done without copying the actual, large image files from the slave PACS servers $110_n$.

Security Layer 500. For both the unification layer 400 and emulation layer 300, the IMPACS system 200 provides a robust and extensible security framework 510 that allows for flexible permissioning for various users, groups or other defined roles to view or modify the data from the various slave PACS servers $110_n$.

Extension Layer 600. Thanks to its process brain/control engine 201, the IMPACS system 200 can also be programmed to support many additional functions and even more can be easily added as needs dictate. As such, it is a powerful and extensible platform for DICOM interoperability permitting images to be incorporated and shared in any medical or other workflow.

From the perspective of a user $U_n$, workstation $WS_n$, or a modality $M_n$, working with the IMPACS system 200 is identical to working with any standard PACS server 110 that supports the DICOM standard. The fact that there are many slave PACS servers $110_n$ underlying the IMPACS system

200 is hidden from both the modalities $M_n$ and the users $U_n$. The modalities $M_n$ and users $U_n$ interact with what they perceive to be a "standard" PACS server 110. Again, the slave PACS servers 110$_n$ of the IMPACS system 200, interact with their respective users $U_n$ and modalities $M_n$ almost exactly as they would were these entities connected directly to them, even though such interaction is actually being conducted by the IMPACS system 200 on behalf of the users $U_n$ and modalities $M_n$.

Fundamentally thus, the IMPACS system 200 is the antithesis of a peer-to-peer image-sharing system of the prior art because the authorizations, transport mechanisms and even the data transfers for all the interactions between the various participants be they consumers or providers of data are handled, tracked and maintained by the IMPACS system 200 in a fashion selected for efficiency based on the circumstances.

In the discussion below, when we refer to the IMPACS server, we typically mean the IMPACS system 200. Again, when we talk of DICOM entities (other than Slave PACS servers 110$_n$) connected to the IMPACS system (or server) 200, it should be understood that we mean entities connected to the same through its PACS server interface 210. Finally, when we discuss programming the IMPACS system 200, it should be read as programming its brain/control engine 201. We will not distinguish between the IMPACS 200 (or IMPACS system 200), its brain/control engine 201 and its PACS server interface 210 unless warranted specifically by the context.

The various functional layers of the IMPACS system 200 are explained in detail in the sections below.

6.1 Emulation Layer 300

The IMPACS system 200 can emulate all the relevant functions of any of its underlying slave PACS servers 110$_n$ for any modality $M_n$, user $U_n$, or client/workstation $WS_n$ that was originally connected to that slave PACS server 110$_n$. In this mode, the IMPACS system 200 is invisible from the perspective of any modality $M_n$, user $U_n$, or client/workstation $WS_n$ connected to it because each such entity believes it is connected to a "standard" PACS server 110 which is what the IMPACS' PACS server interface 210 is. An overview of the IMPACS system 200's emulation layer 300 is shown in FIG. 7.

As shown in FIG. 7, consider a PACS server 110$_a$ that is in use within Hospital A and has a variety of clients/workstations $WS_n$ and modalities $M_n$ connected to it. Were this server to become a slave PACS server 110$_a$ to IMPACS system 200, its connected entities could retain their original connections to this now-enslaved PACS 110$_a$ and continue to work as before (as shown on the left side of FIG. 7). However, if needed (and configured) the connected entities (clients, workstations $WS_n$ and modalities $M_n$) could also be detached from the slave PACS server 110$_a$ and connected to the IMPACS system 200 instead, with only the IMPACS system 200 connecting to slave PACS server 110$_a$ (as shown on the right side of FIG. 7).

When the modalities $M_n$ are connected directly to the IMPACS system 200 instead of their slave PACS server 110$_a$, the IMPACS system 200 will allow them to store the images they obtain directly into their corresponding slave PACS server 110$_a$ as well as recover or modify these images as needed using the same protocols they would in interacting with their local PACS server 110$_a$. Importantly, the units connecting to the IMPACS system 200 would use the same patient, study, image and other DICOM identifiers that they would have normally used in their workflow assuming the IMPACS system 200 did not exist at all. The only change that would be made by modalities $M_n$ would be to replace the connection to their local PACS server 110$_n$ with one to the IMPACS system 200 through its PACS server interface 210 instead.

Again, for workstations $WS_n$ that need to access the images and work with them, having the IMPACS system 200 replace the local PACS 110$_n$ would be an equally seamless process. Workstations $WS_n$ would be able to access the DICOM images using all the same protocols that they were using prior to the existence of the IMPACS system 200, using the same identifiers for patients as before.

One limitation in emulation mode 300 in the IMPACS system 200 is where it comes to user roles. The IMPACS system 200 can have a number of underlying slave PACS servers 110$_n$ each of which may have its own set of authorized users and protocols for authentication of the same. These user roles and protocols will generally not be identical across slave PACS servers 110$_n$.

When a user $U_n$ uses slave-PACS-provided credentials, the IMPACS system 200 will generally have no way to determine just from those credentials exactly which slave PACS system 100$_n$ (slave PACS server 110$_n$) they apply to. The same username for example can be repeated in many of the underlying slave PACS servers 110$_n$, and refer to entirely different users $U_n$. The IMPACS system 200 however can provide some automatic support for slave-PACS-level credentials when certain conditions are met as will be discussed below.

The emulation layer 300 may appear to serve little purpose than to route a connected modality $M_n$ or workstation $WS_n$ to the appropriate slave PACS server 110$_n$ with the associated overhead. However, the IMPACS system 200 can also be configured to perform certain optimizations in emulation mode 300 thereby improving the efficiency of working with the old slave PACS server 110$_n$. Specifically, the IMPACS system 200 can:

perform some or all image searches using a cached copy of the slave PACS' 110$_n$ DICOM image tags leaving the slave PACS server 110$_n$ only with the task of serving up the final images to the IMPACS system 200. This would eliminate the need to upgrade the entire image storage system just to service more user search requests.

cache and serve up frequently used images with no impact to the slave PACS servers 110$_n$ at all.

allow modalities $M_n$ connected to it to operate at full speed even when their associated slave PACS server 110$_n$ is temporarily down or overloaded. This is because the IMPACS system 200 can also cache images stored for later upload to the slave PACS server 110$_n$.

There are also other benefits to modalities $M_n$ operating using the emulation layer 300 that come from the fact that the IMPACS system 200 implementation becomes more efficient when full use is made of the intelligence of its process brain/control engine 201. These issues will be further discussed later.

6.2 Unification Layer 400

The IMPACS system 200 also has the ability to unify all the data in the slave PACS servers 110$_n$ in its framework so that all the data appear to be located within it and correctly organized by patient, study, series and other DICOM groupings just as in a monolithic PACS server 110. That is, the IMPACS system 200 can appear as a single PACS server 110 that appears to have all the data that is resident in the slave PACS servers 110$_n$. In this mode, the slave PACS servers 110$_n$ are not visible from the perspective of any modality $M_n$ or client/workstation $WS_n$ connected to the IMPACS system

200. FIG. 8 illustrates the working of the IMPACS system 200 unification layer 400. To provide such unification across all the slave PACS servers 110$_n$, the IMPACS system 200 is configured to do some or all of the following:

- Create a Common Patient Identity to Unify Patient Identities Across Slave Servers 110$_n$. For a single patient, Jack McCoy, who might possess different identities in each of the slave PACS servers 110$_n$, the IMPACS system 200 will establish a new, unique patient superidentity under which all the slave PACS server 110$_n$ identities for the patient in question will be unified.

- Allow for Unified Roles and/or Authentication to all Slave Servers 110$_n$. The IMPACS system 200 maintains a set of roles/identities for its various users that will map into equivalent roles at the slave PACS server 110$_n$. Thus, if there is a user, Nurse Doe, in Slave Server 110$_a$, and another, Nurse Buck, in Slave Server 110$_b$, IMPACS system 200 can create a role of Nurse DoeBuck which would have all the permissions of both Nurses Doe and Buck in their respective slave servers 110$_a$ and 110$_b$. A user logging into the IMPACS system 200 with this new role, would be able thus to access images across both slave servers 110$_a$ and 110$_b$ without having to authenticate separately to each of them as Nurses Doe and Buck—the IMPACS system 200 will handle all this automatically based on the permissions given to the new role. Of course, the system can also create new IMPACS system 200 roles (with different user names and credentials established by the IMPACS system 200) that mirror the more limited permissions of Nurses Doe and Buck in their respective slave PACS servers 110$_a$ and 110$_b$. In emulation mode 300, the IMPACS system 200 can, in certain cases, authenticate users to the slave PACS servers 110$_a$ and 110$_b$ they are associated with rather than creating its own user roles for such users. These issues will be further discussed below in connection with the implementation of IMPACS system 200.

- Permit Unified Searches and Filters for Patient DICOM Data. Given that the IMPACS system 200 has a unified identity mechanism for patients, it can search for DICOM tags across all the underlying slave PACS servers 110$_n$ and combine the results by patient across all the servers 110$_n$.

- Fix Inconsistent or Missing DICOM Tags to Permit Better Searching. Many DICOM generating modalities M$_n$ often fill in the minimal required set of DICOM tags for the image leaving blank other useful (but optional) tags. Thus, for example, many providers do not fill in the Institution Name tag in the DICOM image, or do not update it if the institution's name changes simply because within the provider this tag is never used. Other providers add various custom tags (which are permitted by the DICOM standard) to the images to store additional image information some of which might supplant the standard tags within the organization. The IMPACS system 200 can combine or alter tags as needed for consistency and efficiency using algorithms customized for each slave PACS server 110$_n$ and its institution's specific internal protocols. Thus, the IMPACS system 200 can dynamically overwrite or fill in the Institution Name, Institution Address and other such missing or incorrect information while serving up an image to a requesting client without altering the stored image at the slave PACS server 110$_n$.

- Alter or Add DICOM Tags for Specific Use Cases. The DICOM standard allows for additional DICOM tags to be added to the image when needed by providers for their internal requirements. Again, in situations where images are used for research or population studies, they may have to be anonymized by removing patient-specific data because of laws regarding patient privacy. The IMPACS system 200 can be configured to, on the fly, either add additional, custom tags to the delivered image or rewrite existing tags when needed for such specific use cases. It can perform such functions either while storing images from modalities M$_n$, or delivering them to users U$_n$/workstations WS$_n$. However, the IMPACS system 200 will not typically alter tags such as the UIDs for study, series or instance as created by true DICOM modalities M$_n$ because they are required to be globally unique and should effectively be immutable. Regrouping of incorrectly classified instances into different studies or series is technically possible at the IMPACS system 200 level by a rewrite of study or series tags, but should be avoided as a general rule in most cases.

- Establish Rules for Image Storage/Retrieval Using New Storage Mechanisms to Improve Efficiency. The IMPACS system 200 could permit an existing modality M$_n$ that exclusively used its local PACS server 110$_a$ for all its patient images to store some of the patient images (say for patients visiting from a satellite hospital) into a different PACS server 110$_b$. Alternatively, storage of images could be routed by the size of the image stored. Again, image access might be speeded up dramatically by maintaining multiple copies of images across slave PACS servers 110$_n$, or partitioning the image store to permit faster access. Also, the IMPACS system 200 could cache frequently requested images in its own memory or local disk, and deliver them quickly to the requesting agent without even querying the corresponding slave PACS server 110$_n$ reducing the load on the slave PACS server 110$_n$ significantly. Rules for image storage and retrieval could be established at the level of the IMPACS system 200 and implemented by the same automatically. Importantly, this would happen in a fashion that is totally seamless to the modalities M$_n$ or workstations WS$_n$ which continue to store and retrieve images as before.

6.3 Security Layer 500

The IMPACS system 200 can be configured to implement a powerful and extensible security framework 510 for the imaging workflow that can permit granular access at the level of a single DICOM image, study, series, patient or any subset thereof for any group of users, workstations WS$_n$ or other defined security roles. In performing its security layer functions 500 the IMPACS system 200 needs to recognize that:

- The slave PACS servers 110$_n$ may have their own security infrastructure that could require authentication.
- The unification layer 400 of the IMPACS system 200 will require the creation of new roles and users that have access to images across multiple slave PACS servers 110$_n$. These super access roles have no analog in any of the connected slave PACS systems 100$_n$ or their associated servers 110$_n$.

In its emulation layer 300, the IMPACS system 200 can be configured to guarantee that any workstation WS$_n$ or modality M$_n$ can search, view, or modify only those images that it is permissioned for in the specific slave PACS server 110$_n$ that it is associated with. In unification mode 400 the IMPACS system 200 can operate with its own user roles and identities and ensure that these identities can access only those images that they are permissioned for. In the unification layer 400 moreover, the IMPACS system 200 can allow for the possibility that specific users can be given authorizations to see more images across the slave PACS servers $110_n$, or alternatively, have these permissions revoked. Moreover, new slave PACS servers $110_n$ can be brought into the IMPACS system 200 setup creating the need for extending user permissions across these new machines. Thus, the IMPACS system 200 permission scheme can be configured so that a specific identity's image/patient views are updated appropriately when permissions are granted or revoked.

The IMPACS system 200 is designed to make the permission scheme transparent to the users $U_n$. Thus, a user $U_n$ accessing the IMPACS system 200 emulation layer 300 will see only what he is authorized to see in his slave PACS server $110_n$. When accessing the unification layer 400 with the appropriate identity, the user $U_n$ will see exactly those images he is permissioned for but now across all the connected slave PACS servers $110_n$. In either instance, any agent connected to the IMPACS system 200 will be able to see, list and search across only what he is authorized for and nothing else.

6.4 Extension Layer 600

The IMPACS system 200's brain/control engine 201 is set up to understand DICOM formats and workflows and can be configured to provide considerable functionality beyond just combining data from or emulating multiple slave PACS servers $110_n$. These additional functions that the IMPACS system 200 can provide makes up the extension layer 600. There are many such services the IMPACS system 200 can provide and its brain/control engine 201 can be extended to provide even more services as needs dictate. A non-exhaustive list of some of the functions that the IMPACS system 200 can provide with the extension layer 600 includes:

Ensuring Image Redundancy. The IMPACS system 200 can be configured to seamlessly cache and send images from a connected modality $M_n$ to multiple slave PACS servers $110_n$ for storage. This would mean thus, that it could implement a real-time hot-backup for a slave PACS server 110.

Speeding up Image Access. If a primary slave PACS server $110_a$ has a secondary backup PACS server $110_b$ that is also set up as a slave PACS server $110_b$, the IMPACS system 200 can route image requests both to the primary and the backup servers $110_a$ and $110_b$ to speed up access. Thus, a hot-backup of a slave PACS server $110_a$ can be put to good use at times of peak usage. Again, the IMPACS system 200 could cache heavily used images in its own local storage and serve up requests for these images without even accessing the corresponding slave PACS server $110_n$.

DICOM-Enabling New Modalities. The DICOM standard is very flexible because it supports virtually any type of image as long as it has the right DICOM wrapper tags. However, not all image acquisition devices can provide the DICOM tag addenda and so most of those cannot work with a conventional PACS server 110. For example, a picture taken on a camera phone is not in DICOM format because the phone does not have the functions needed to convert these images into a DICOM format. However, such a phone can be configured as a "modality" $M_n$ in the IMPACS system 200 with the latter being programmed to provide all the DICOM tag wrappers for any image acquired from this phone when given some additional data as to the patient, and then dispatch the wrapped image for storage to the appropriate slave PACS server $110_n$. With this approach, any non-DICOM-aware device can be converted into a full-fledged and low-cost modality $M_n$. This will be described in more detail below.

PACS-Enabling Non-DICOM Image Stores. The IMPACS system 200 can DICOM-enable non DICOM modalities $M_n$ because of its ability to wrap an image delivered to it with the appropriate DICOM tags using a combination of information in the image already and its knowledge about the modality $M_n$. If the images did not come from a modality $M_n$ but from a non-DICOM image storage server, the IMPACS system 200 could simply wrap all the images from such a server with DICOM tags and even convert the images, if they cannot be viewed by standard DICOM viewers, into formats that are easily viewable. If the IMPACS system 200 were configured to DICOM-wrap all the images from a non-DICOM image store and were to commit these DICOM tags into its internal databases, it could then permit searching for these images by any agent and serve up these images as well. Since the IMPACS system 200 can access and DICOM-wrap, and if needed convert images on the fly, it can easily serve them up as well on demand and deliver them not just to a slave PACS server 110 for storage when required but also to an accessing workstation WS. Thus the IMPACS system 200 can provide a PACS server 110 interface for a non-PACS image repository such as for example, a repository of non-DICOM pathology slides, converting it effectively into a "pseudo PACS" server 810. This will be further discussed below.

Managing an Imaging Workflow. When modalities $M_n$, users $U_n$ or workstations $WS_n$ connect to the IMPACS system 200 the latter implements various rules that determine what exactly it needs to do to service their requests. At the minimum the IMPACS system 200 supports all DICOM requests. However, the IMPACS' brain/control engine 201 can be extended to handle more complex process functions. These could be sending messages to other PACS servers $110_n$ when an image is stored, notifying users when images are changed etc. The IMPACS system 200 functionality can be extended to handle issues that might arise more generally in the handling of medical images.

Filtering or Altering DICOM Tags For Specific Uses. This feature was briefly mentioned above in connection with the fixing, altering or adding DICOM tags. The IMPACS system 200 can anonymize the images from the various slave PACS servers $110_n$ by overwriting the patient specific data on the images it serves up dynamically without altering the actual image data in any of its slave PACS servers $110_n$. As such, it can serve as a portal into any of the slave PACS servers $110_n$ without the latter needing to do anything to their images to make this possible. This can be useful for research and other functions. For example, the IMPACS system 200, with some additional patient-specific data from the medical provider, can filter out only the images of cancer patients from its slave PACS servers $110_n$ if it has to serve as the portal for a network of cancer specialists. Alternatively, it can be used to filter out only patients covered by a given insurer so that the latter can operate with single IMPACS system 200 for all of its patients etc. The important thing to note is much as the IMPACS system 200 unifies patients by creating its own patient identity, it can also filter by the same, as well as unify and filter using other DICOM tags. It can also write specific filter tags into its own tag database as custom DICOM tags, effectively storing the results of the filters. This will make future retrieval of the filtered results much faster.

The above functions/features are typically not provided by any typical PACS server 110. However, the IMPACS system 200 can seamlessly provide such functionality with the extension layer 600 while behaving in all respects like a regular PACS server 110 (through its PACS server interface 210) from the perspective of the user $U_n$ or modality $M_n$.

6.5 Implementation of the IMPACS System 200

The IMPACS system 200 in its most general form can be viewed as a powerful and extensible process brain that can coordinate the entire DICOM process flow. As such, it is a DICOM-process-aware instance of the general Process Interoperability Platform ("PIPCO") as described in pending application Ser. No. 16/037,249 for "System for Process Coordination and Interoperability across Different Systems, Platforms and/or Businesses" filed on Jul. 17, 2018. The IMPACS system 200 of the present invention can do all of the following:

emulate the behavior of one or more of the individual slave PACS servers $110_n$ connected to it so connected users $U_n$ and modalities $M_n$ believe that they are actually connected directly to the slave PACS server $110_n$.

unify images across all of the slave PACS servers $110_n$ and permit searching across all of them as though all the images are actually resident in itself. To modalities $M_n$ connected to the IMPACS system 200 in this context, it will behave in all respects like a regular, standalone PACS server 110.

The implementation of the IMPACS system 200 of the present invention can be broken down into the broad functional areas or elements below, as shown in FIG. 9:

Slave Control Engine 220. The IMPACS system 200 needs to obtain all the details regarding the slave PACS systems 100, and their associated servers $110_n$ connected to it, their users $U_n$ and/or modalities $M_n$ and the security protocols they use. Without information on the slave PACS servers $110_n$, the IMPACS system 200 cannot provide any functions at all. Without user $U_n$ or modality $M_n$ information from the slave PACS server $110_n$, it will be unable to provide any of its emulation layer functions 300.

DICOM Tag Replication 410. The DICOM images the IMPACS system 200 will provide to connected clients reside on the slave PACS servers $110_n$. To permit patient unification, searching across images etc. the IMPACS system 200 is configured to maintain at least a minimal set of DICOM tag information along with associations that tell it which slave PACS server $110_n$ the images in question are located in.

Data Unification and Transformation 420. To provide its unification layer 400 functions, the IMPACS system 200 will typically need to map patient identities correctly across the slave PACS servers $110_n$, no matter what PatientID tags their respective images might be using. This will ensure that a given patient's images across the slave PACS servers $110_n$ are accessible on the IMPACS system 200 under a single patient identifier. The IMPACS system 200 might also need to transform some of the data returned by the slave PACS server $110_n$ by overwriting or fixing erroneous or missing tags in their DICOM data on-the-fly. For these purposes, the IMPACS system 200 will maintain a map that relates the correct values it should use to those that are being used in the slave PACS system $100_n$/server $110_n$ for the images that are affected.

Security Framework 510. The IMPACS system 200 can, and typically will, provide a framework for user and role definition, authentication and secure access to permissioned images. In general, the user roles defined in the IMPACS system 200 will not have any direct relationship to those in the slave PACS systems $100_n$ and their associated servers $110_n$.

Extensible Process Engine 610. The IMPACS system 200 implements the actual central processing brain identified above as the brain/control engine 201 that provides PACS services to connected clients bringing together all its emulation 300, unification 400, security 500 and other functions 600. This central intelligence can also be extended to handle more process functions and provide greater functionality as needed. We designate the extensible process part of the IMPACS brain/control engine 201 as its extensible process engine 610. For most practical purposes, the extensible process engine 610 should be viewed as being part of the IMPACS brain/control engine 201.

Each of these implementation areas/elements are described in detail below.

6.5.1 Slave Control Engine 220

The IMPACS system 200 is intended to make a group of slave PACS servers $110_n$ work as though their data were all in a single PACS server 110. As such, it needs to route requests on behalf of connected modalities $M_n$, users $U_n$, or workstations $WS_n$ to the appropriate underlying slave PACS servers $110_n$. It may also have to authenticate users $U_n$ and/or modalities $M_n$ with the slave PACS system $100_n$ or servers $110_n$ when used in emulation mode 300. To perform these so-called slave control functions, the Slave Control Engine 220, which is part of the IMPACS brain/control engine 201, of the IMPACS system 200 is configured to do all of the following:

6.5.1.1 Manage Connections and Routing to Slave PACS Servers $110_n$

The IMPACS system 200 is configured to connect seamlessly to the slave PACS servers 110 in its framework. It can accomplish this when it is aware of their existence and when it has the right protocols/credentials to connect to them for image recovery, storage, querying etc. as permitted. To this end, the IMPACS system 200 will:

Establish a list of slave PACS servers $110_n$ that are authorized to be part of the IMPACS framework 200.

Maintain a list of relevant properties for each authorized slave PACS system $100_n$ and its associated server 110 to permit connection. These properties would include the authentication and networking protocols to connect along with any authentication credentials that need to be used for the same.

Implement the appropriate networking, authentication and connection protocols using the data from the above steps to permit access of the slave PACS servers $110_n$ by any modalities $M_n$ or clients connected to the IMPACS system 200.

The first two items above can be handled using a standard relational database. The final step above can be easily implemented because virtually all of the required connection and other protocols are typically built into most modern computer operating systems—the only requirement is that these protocols be appropriately configured using the data collected in the first two steps. In some situations, it might be necessary to provide a customized framework for connectivity.

The above properties and implementations will be internal to the IMPACS system 200. Any client or modality $M_n$ connecting to the IMPACS system 200 will not be aware of the routing of requests to the slave PACS server $110_n$ going on under the hood.

6.5.1.2 Incorporate Slave PACS Server $110_n$ Security Protocols and Credentials for Connectivity The slave PACS servers $110_n$ underlying the IMPACS system 200 may operate with different security frameworks, roles and technologies, as illustrated in FIG. 10. Thus, one of the slave PACS servers $110_b$ being accessed by a surgeon $U_2$ may operate with Lightweight Directory Access Protocol (LDAP) access protocols for security while another slave PACS server $110_a$ being accessed by a nurse $U_1$ might operate with Microsoft Azure and another slave PACS server $110_c$ being accessed by a doctor $U_3$ might operate with the Secure Shell (SSH) network protocol. To pass through requests to the slave PACS servers $110_n$, the IMPACS system 200 has to connects to them using their respective security frameworks.

Again, for connection, the slave PACS servers $110_n$ might require the IMPACS system 200 to authenticate with the appropriate credentials. In emulation mode 300 (i.e., as implemented by emulation layer 300), such authentication will generally be with the IMPACS system 200 user's login credentials which just get passed on to the slave PACS server $110_n$. However, when providing the functions in its unification layer 400, the IMPACS system 200 will have to take care of the access permissions for users $U_n$ across servers $110_n$ because each slave PACS server $110_n$'s permissions relate only to the data that the latter has. In this situation, the IMPACS system 200 has to provide a more extensive user mapping to be discussed below.

In general, the IMPACS system 200 will likely have to authenticate to each slave PACS server $110_n$ providing the appropriate credentials in a fashion consistent with the latter's security framework. To do this, the IMPACS system 200 stores these credentials in its internal databases for provision to the slave PACS servers $110_n$ as needed. The IMPACS system 200 can be configured with the ability to establish connectivity and deliver these credentials to the slave PACS server $110_n$ using the latter's own security protocols (be they LDAP, Azure, or anything else).

6.5.1.3 Establish an Optional Framework for Modalities $M_n$ Connecting to Emulation Layer 300

When a legacy modality $M_n$ connects to the IMPACS system 200 in emulation mode which means it connects to the latter's emulation layer 300, it expects the IMPACS PACS server interface 210 to behave like its original (now slave) PACS server $110_n$ and the legacy modality $M_n$ continues to use DICOM tags appropriate to the slave PACS system $100_n$ and server $110_n$ (which may even be in conflict with the tags used by the IMPACS system 200 itself). Consider thus the case where an existing modality (say MRI machine $M_{10}$ in Hospital A) is connected to a local PACS server $110_a$ in that hospital (say cardiology PACS server $110_a$). Assume that the modality $M_{10}$ connects directly to the IMPACS system 200 making its PACS server $110_a$ into a slave of the IMPACS system 200. If the modality $M_{10}$ continues to use the patient identifiers established within Hospital A, the IMPACS system 200 operates to route all the image storage requests emanating from this modality to slave PACS server $110_a$, the local PACS server that originally served this modality $M_{10}$. Even if slave PACS server $110_a$ is no longer available, the IMPACS system 200 will have to maintain its own subsidiary DICOM store corresponding to slave PACS server $110_a$ which operates with the same patient identifiers used by the slave PACS server $110_a$.

The IMPACS system 200 is configured with a number of features to provide the emulation layer 300 functionality. Specifically:

The modality $M_{10}$ in this case does not direct the IMPACS 200 to store the images it provides into PACS server $110_a$, nor does it specify that the images in question are even from Hospital A with the latter's patient identifiers. The IMPACS system 200 is configured to determine these relationships automatically.

The modality $M_{10}$ might communicate with its slave PACS server $110_a$ using specific authentication mechanisms and protocols that might in some cases be defined and/or limited by its hardware. The IMPACS system 200 can be configured to be aware of these protocols and identify itself and behave exactly like the legacy modality $M_{10}$ in connecting to the slave PACS server $110_a$ so that the storage of the images is seamless. At the same time, the IMPACS system 200 would appear exactly like the slave PACS server $110_a$ to the connected modality $M_{10}$.

To pass through the modality's $M_{10}$ request to the appropriate slave PACS system $100a$ (and its associated slave PACS server $110_a$), the IMPACS system 200:

Creates a Modality Identity Map 310 that relates every legacy modality $M_n$ that connects to it to the appropriate slave PACS server $110_n$ in its network. Thus for the example above, the map would relate modality $M_{10}$ to slave PACS server $110_a$ in Hospital A. The IMPACS system 200 as specified earlier, is also configured with the knowledge needed to connect to slave PACS server $110_a$. In some cases, rather than an explicit map that lists every modality $M_n$ connected to a slave PACS server $110_n$, a network address range can be used if such a specific range can be set up for modalities $M_n$ at the slave PACS server $110_a$ level.

Maintains or passes through the authentication, networking and other credentials each modality $M_n$ would have to use to store images into its slave PACS server $110_n$ using the appropriate protocols. This will be needed by the IMPACS system 200 to authenticate the modalities $M_n$ or alternatively, permit the slave PACS server $110_n$ to provide that function instead.

Emulates the same authentication/connection schemes as the slave PACS server $110_n$ when modalities $M_n$ connect to the IMPACS system 200. That is, the IMPACS system 200 will behave exactly like the slave PACS server $110_n$ to the connecting modality $M_n$. The latter thus will authenticate and connect to the IMPACS system 200 exactly as it did to its corresponding slave PACS server $110_n$.

Behaves like the modality $M_n$ where it comes to connecting to the slave PACS server $110_n$ on behalf of a modality $M_n$. Thus, the IMPACS system 200 will maintain or pass through the authentication, networking and other credentials each modality $M_n$ would have to use to store images into its slave PACS server $110_n$.

As shown in FIG. 11, if MRI machine $M_{10}$ which was connected to PACS server $110_a$ (FIG. 11 left side) were to connect to the IMPACS system 200 instead (FIG. 11 right side), the latter would behave exactly like PACS server $110_a$ when MRI machine $M_{10}$ connects to it using the same authentication and connection protocols. When the request from MRI machine $M_{10}$ is received, the IMPACS system 200 would connect to PACS server $110_a$ and in this case behave exactly like MRI machine $M_{10}$ providing the appropriate credentials, network MAC addresses etc. and observing the same protocols.

Many PACS servers $110_n$ do not have any authentication for modalities $M_n$ which typically tend to be large machines hardwired to the PACS server 110. However, many such modalities $M_n$ might be connected to the IMPACS system 200 for its emulation functions 300, and these modalities $M_n$ might belong to completely different providers with different (slave) PACS servers $110_n$. As such, the IMPACS system 200 in an embodiment is configured to ensure that the modality access is properly controlled with each modality $M_n$ being associated to the right slave PACS server $110_n$ with no prospect of error using its Modality Identity Map 310. The IMPACS system 200 will manage this by tracking characteristics such as MAC addresses, network connections, network addresses etc. that can uniquely identify a modality $M_n$, with no possibility of spoofing, so that the proper association to its slave PACS server 110) is always possible, recognizing that the latter might provide no security framework at all for this purpose. In some special cases, where the IMPACS is DICOM-enabling non-DICOM modalities such as personal smartphones, it may associate the "modality" with its appropriate slave PACS server 110 using user credentials for the purpose. This is discussed at greater length in later sections. The IMPACS system 200 can provide emulation functions 300 only for a modality $M_n$ that can be uniquely associated with its correct slave PACS server $110_n$.

6.5.1.4 Create and Maintain an Optional User Framework for Emulation Mode 300

In providing the functions in its emulation layer 300, the IMPACS system 200 can be configured to accept logins from users $U_n$ that are permissioned only on a specific slave PACS server $110_n$. In such an instance, the IMPACS system 200 will have to be able to authenticate such a user $U_n$ by passing through his authentication request to the appropriate slave PACS server $110_n$. However, given that usernames are often repeated across computers (like jsmith for our proverbial John Smith), the IMPACS system 200 will generally not pass through authentication to a slave PACS server $110_n$ based on user name alone.

In the section above, a pass through for modalities $M_n$ is allowed because the latter are typically devices with fixed network and other characteristics that can be detected and located with reliability. However, the same is generally not true for users $U_n$ who are much more mobile. As shown in FIG. 12, such user pass through could be permitted in certain special situations where users $U_n$ are confined to specific, fixed workstations $WS_n$ that can be reliably detected. In such situations, the IMPACS system 200 will maintain a Workstation Map 320, that is very similar to its Modality Identity Map 310, and simply route user requests from such workstations $WS_n$ (and only these workstations $WS_n$) to the associated slave PACS server $110_n$.

In general, to maximize the benefit of the present invention, IMPACS system 200's emulation mode 300 for users $U_n$ should not be used and instead one should rely on the IMPACS's 200 own user security framework (to be discussed below) that can be used to create user identities and map them to equivalent identities at one or more slave PACS servers $110_n$.

The above-mentioned maps/credentials/protocols should be updated whenever a new slave PACS server $110_n$ is connected to the IMPACS system 200. Similarly, when new modalities $M_n$, users $U_n$, or workstations $WS_n$ that require emulation functions 300 are connected to the IMPACS system 200, such maps/credentials/protocols also need to be updated. Once maps (e.g. Modality Identity Map 310 and Workstation Map 320) are configured, the IMPACS system 200 can seamlessly route requests to the appropriate slave PACS server $110_n$ be they for its own unification functions 400 or for emulation purposes 300—all of the protocol conversions and authentications happen entirely within the IMPACS system 200.

A relational database is adequate for creating the Modality Identity Map 310 and Workstation Map 320 and authentication credentials/protocols for slave PACS servers $110_n$, modalities $M_n$, users $U_n$, or workstations $WS_n$. However, the IMPACS system 200 will have to implement the actual protocols for connection to the slave PACS servers $110_n$ managing the authentication as needed. The DICOM standard does not mandate a specific authentication protocol for PACS servers $110_n$. As such, most PACS servers $110_n$ use a variety of common, standard mechanisms for this purpose and numerous free and commercial packages exist to support these mechanisms. The IMPACS system 200 will implement the authentication protocols required to connect to the slave PACS servers $110_n$ and modalities $M_n$ and workstations $WS_n$ in its network using authentication software, with customization to varying degrees when necessary. Once the actual connection to the slave PACS server $110_n$ has taken place, all image-related functions can be performed using standard DICOM protocols. In all cases the IMPACS system 200 (through its PACS server interface 210) appears to the connected client or modality $M_n$ as a regular PACS server 110.

6.5.2 DICOM Data Management (DICOM Tag Replication 410 and Data Unification and Transformation 420)

With the slave PACS servers $110_n$ connected, the IMPACS system 200 can be configured to address a number of data issues that it has to overcome so as to provide its intended functionality. Many (though not all) of these issues come up because of the unification function layer 400 the IMPACS is called on to provide. Specifically:

- Identifying patients $P_n$ correctly across the slave PACS servers $110_n$ is not straightforward because the locally unique MRN or PatientID tag is not unique across PACS servers $110_n$. A specific PatientID DICOM tag referencing a given patient $P_n$ in one slave PACS server 110 might refer to an entirely different patient $P_n$ in another. Again, the same patient $P_n$ can have different PatientID tags in his DICOM images across different slave PACS servers $110_n$.
- Searching for specific DICOM tags in the IMPACS system 200 will mean searching across all the associated slave PACS servers $110_n$.
- Fixing missing or incorrect tags will not be possible unless the IMPACS system 200 knows the tags that need fixing and their associated images and slave PACS servers $110_n$.

To address the above issues, the IMPACS system 200 can be configured to perform the various functions discussed in the sections below in its implementation.

6.5.2.1 Establish a Central Database of DICOM Tags 430

Most PACS servers $110_n$ provide capabilities to search for DICOM images by patient $P_n$, modality $M_n$ or other image tags. To support such functions, as shown in FIG. 13, IMPACS system 200 will organize the tag information from all the slave PACS servers $110_n$ into a database 430 maintained at the IMPACS system 200 itself. This Master DICOM tag database 430 can be searched at the IMPACS level 200 without affecting any of the slave PACS servers $110_n$, with the latter being contacted only when the actual images are accessed.

The DICOM tag database 430 established by the IMPACS system 200 can take a variety of forms with DICOM Tag Replication 410. At the very minimum, it is a database that only has a list of the images from each slave PACS 110$_n$ along with their study, series and instance UIDs. At the other extreme, it is a database that replicates/copies every tag from every image in its slave PACS server 110$_n$ network. Even if some or all the tags are copied, the volume of data copied is still very small in comparison to the actual images. As such, the amount of data maintained in the IMPACS system 200 DICOM tag database 430 should be very small in comparison to a regular PACS server 110. The user permissioning and security for the IMPACS' 200 unification layer 400 have to be associated to individual images or image groups to permit access of images across the slave PACS servers 110$_n$. As such, the IMPACS system 200 cannot implement most, if not all, of its unification functions 400 without at least a minimum tag database 430 that has image UIDs.

If none of the unification functions 400 are desired in a particular implementation, the IMPACS system 200 can execute queries on-the-fly across all the slave PACS servers 110$_n$ and combine them suitably with authorization filters that are determined by non-image-UID based rules. However, each query may impose a heavy network load that could impair performance both of the slave PACS servers 110$_n$ and the IMPACS system 200 itself. Even worse, if one or more slave PACS servers 110$_n$ are not available, the dynamically obtained results may not be comprehensive or accurate. Therefore, the IMPACS system 200 should be implemented, at a minimum, with DICOM tag replication (or copying) 410 of at least a reasonable subset of DICOM tags into the database 430 as described above to address these concerns.

When the Master DICOM tag database 430 is maintained at the IMPACS system 200 level it may be limited to a small subset of searchable tags during configuration, or, in its most comprehensive form, contain every permissible DICOM image tag. Even so, the tags in a DICOM image do not take up much storage especially relative to the image. As such, the tag database 430 in the IMPACS system 200 will be very lightweight. Importantly, the tags obtained from the images must be combined with additional information that links these images to a specific slave PACS server 110 in which it resides. Thus, in looking at the results of a tag search we can immediately determine just which slave PACS servers 110$_n$ the images returned belong to.

The Master DICOM tag database 430 at the IMPACS system 200 should be continually updated with current data. It serves for the IMPACS system 200 as the master image index. As such, when any images are added to a slave PACS server 110 and the IMPACS system 200 does not reflect the same in its database 430, the latter's data will not be up to date.

It should be noted that a huge advantage to using the IMPACS system 200 for its emulation layer 300 for modalities M$_n$ is that when images are stored/changed through the IMPACS system 200 in any of the slave PACS servers 110$_n$, the IMPACS system 200 will automatically update its DICOM tag database 430 to reflect these changes. If all the modalities M$_n$ used the IMPACS' 200 emulation functions 300 exclusively instead of connecting to their slave PACS server 110$_n$ directly, the data between the IMPACS system 200 and the slave PACS server 110$_n$ will always be in sync without the need for constant polling of the slave PACS servers 110$_n$ by the IMPACS system 200. Of course, if some modalities M$_n$ directly connect to their own slave PACS server 110$_a$ instead of to the IMPACS system 200, the latter will have to be made aware every time an image is stored or modified in this slave PACS server 110$_a$ so that it can keep its Master DICOM tag databases 430 consistent with the image tags in that specific slave PACS server 110$_a$.

The problem of tag database synchronization does not occur when modalities M$_n$ connect to the IMPACS system 200 in its unification mode 400. When images are stored or modified in this case, the IMPACS system 200 itself implements all the functions and updates its tag database 430 like a standalone PACS server 110.

6.5.2.2 Create and Maintain a Patient Super-Identity Map 431

A part of the Data Unification and Transformation 420 is related to patient identity as mentioned above. One of the key features of the IMPACS system 200 is its ability to unify patient records for a given patient P$_n$ across all of its slave PACS servers 110$_n$. Thus, patients Jack McCoy P$_1$ who are patient 71522 in Hospital A and 61894 in Hospital B are both actually the same individual. If the IMPACS system 200 has to unify his identities across the hospitals, it has to create a Jack McCoy P$_1$ super identity (let us say this is JMC1151) that maps to his identities in Hospitals A and B. This new identity has to be given its own authentication credentials for the IMPACS system 200 and it will not be possible to use these credentials to connect to any of the slave PACS servers 110$_n$ without going through the IMPACS system 200.

The IMPACS system 200 also can be configured to support searching for a given patient's images across all its component slave PACS servers 110$_n$. For this purpose, as discussed earlier, the IMPACS system 200 will shadow (or replace without overwriting) the PatientID DICOM tag of the images with its self-generated patient super-identity. The database of DICOM tags 430 that the IMPACS system 200 establishes by reading the tag data from all the slave PACS servers 110$_n$ is designed precisely for such searches. However, the IMPACS system 200 will be able to support additional functions relative to a standard PACS server 110 stemming from the fact that it connects to multiple PACS servers 110$_n$:

It can search for a patient's records by his/her super-identity. Thus for Jack McCoy P$_1$, the IMPACS system 200 can pull all the images relating to him even though they have different patient identifiers in the slave PACS servers 110$_n$.

It can permit search for a patient's unified record if his/her identity is provided for a given hospital. So, the IMPACS system 200 can find all the images pertaining to Jack McCoy P$_1$ across all the slave PACS servers 110$_n$ given only the patient identifier 71522 used in Hospital A as long as it knows that the identifier provided is the one assigned by Hospital A. In such a situation, the IMPACS system 200 will find the super-identity applicable to identity 71522 for Hospital A, and find the records for the right Jack McCoy P$_1$ across all the hospitals. The IMPACS system 200 can do this efficiently because it does not overwrite any of the images or tags in any of the slave PACS servers 110$_n$.

When searching for a given patient's list of studies, the IMPACS system 200 in its unification role 400 will operate with the patient's super-identity by default and provide all the studies pertaining to that patient across all slave PACS servers 110$_n$ that the user is allowed to see. To the querying user thus, it will appear to be storing all the underlying images from the slave servers 110$_n$ even though it does not. While the functionality to allow for querying with slave PACS-specific patient identifiers can be provided, it will generally be preferable for an IMPACS system 200 user to be completely unaware of these slave PACS server 110$_n$ patient identifiers.

As shown in FIG. 14, a relational database can be used to implement the patient super-identity map 431 creating a super-identity and associating it with multiple patient identities in the component slave servers $110_n$ of the IMPACS system 200. This super-identity (which will be referred to as the IMPACS system 200 patient identity) is unique and internal to the IMPACS system 200 and importantly, maintained completely separate from the patient identifiers used in the slave PACS servers $110_n$. Thus, when IMPACS system 200 creates a patient identifier of JMC1151 for patient Jack McCoy $P_1$, it will maintain a map that relates JMC1151 to the identifiers used in Hospitals A and B above which are 71522 and 61894 respectively. This new patient identity JMC1151 will effectively supersede Jack McCoy's $P_1$ DICOM image PatientID tags which are part of the DICOM standard and set to 71522 and 61894 in the slave PACS servers $110_n$. However, the IMPACS system 200 does this non-destructively without overwriting the images or their tags in the slave PACS servers $110_n$. The old tags will still be available for searching and filtering but only when the search is confined to a single slave PACS server 110.

FIG. 15 is an overview of searching for records across all slave PACS servers $110_n$ with patient super-identity and FIG. 16 is a flow chart of the method. At Step 1, a user $U_1$ initiates his/her request for images for Jack McCoy $P_1$ from IMPACS system 200 after logging into the IMPACS system 200 with his/her credentials. At Step 2, using the Patient Super-Identity Map 431, IMPACS system 200 determines Jack McCoy's $P_1$ images' sources and relevant login credentials for the same. At Step 3, IMPACS system 200 accesses tag information from the Master DICOM Tag database 430 with corresponding patient information for Jack McCoy $P_1$ for each slave PACS $110_n$. At Step 4, the IMPACS system 200 authenticates to slave PACS server $110_n$ with appropriate protocols and corresponding patient information for Jack McCoy $P_1$. At Step 5, IMPACS system 200 retrieves Jack McCoy's $P_1$ DICOM images from each slave PACS $110_n$. At Step 6, Jack McCoy's $P_1$ DICOM image handles retrieved from the various slave PACS servers $110_n$ are combined into a legal DICOM query response and dispatched to user $U_1$ at his/her workstation WS.

The importance of patient unification cannot be stressed enough in the DICOM context given the non-global uniqueness of the patient identifier tag (PatientID) across images from different providers. PACS servers $110_n$ always provide the PatientID tag information but vary in terms of additional patient data they provide. Typically, the name of the patient and the birth date are provided, but few DICOM images have many (or even any) of the other patient-related tags filled in. Practically speaking, it will generally be impossible to provide complete patient unification just with DICOM image data because there are usually too many of the proverbial John Smith patients who will share a common birthday.

The IMPACS system 200 acknowledges that patient unification from the image data alone will be impossible except perhaps within multiple slave PACS servers $110_n$ all within a single hospital chain. As such, as illustrated in FIG. 17, IMPACS system 200 may use external subsystems (such as those tied into the imaging provider's billing system for example) to match the provider's DICOM PatientID tag and the patient's full demographic profile which might include a more broadly-recognized health identifier. In many cases, this association of the patient demographic data to his DICOM PatientID tag may even have to be done manually! Once a patient $P_n$ can be matched to a widely used unique identifier (such as a government health identifier, social security number or private health identifier such as the one provided by a private agency like Experian Health) the IMPACS system 200 can create its central and unique patient identity storing the unique national/regional/other health identifier under this newly created identity, and rely on the latter for subsequent matching of patients. The important thing to note is that the IMPACS system 200 provides a robust framework to unify any patient's data across imaging providers once the mechanism for unification, however handled, is in place.

6.5.2.3 Establish Tag Maps and Data Transformation

In establishing the database of Master DICOM image tags 430, the IMPACS system 200 can fix, alter or add tags as needed based on what the slave PACS server 110 provides. Thus, if a slave PACS server 110 does not fill in the tags for InstitutionName or InstitutionAddress which are standard DICOM tags, the IMPACS system 200 can fill in the values appropriate for that slave PACS server's 110 institution using its own tag database. Again, if the slave PACS' 110 tags reflect a modality type that is incorrect or archaic, the IMPACS system 200 can adjust these tags in its database 430 to have the correct values. When needed, the IMPACS system 200 can also add custom tags to its database 430 for all the images it incorporates into its tag database from the slave PACS servers $110_n$. Such custom tags could for example be specific use tags such as whether these images should be made available for research or not, which types of research they are usable for etc.

To provide the functionality for data transformation as part of the Data Unification and Transformation 420, the IMPACS system 200 has a Rules Engine 440 that implements the tag transformation using a defined set of transformation rules that it is provided. The rules might relate specific image instances, series or studies (by UID) and specific tags that need to be rewritten along with the correct values. Alternatively, the rules might be by slave PACS server 110 where a blanket rewrite of specific tags for all obtained images might be undertaken and so on. The specific rules will be determined by the slave PACS servers $110_n$ and the tags in question that need fixing. FIG. 18 provides an overview of the Rules Engine 440.

This rules engine 440 is essentially part of the IMPACS brain/control engine 201. It is a specific use case example for the Domain Specific Programming Language referred to in the pending application Ser. No. 16/037,249 for "System for Process Coordination and Interoperability across Different Systems, Platforms and/or Business" filed on Jul. 17, 2018.

FIGS. 19 and 20 show the Tag Modification process in some detail. As seen in these figures, the Rules Engine 440 requires that the IMPACS system 200 maintain a Tag Map/Override database 432 that relates images for which tag overriding has to be performed to a list of tags and their overridden values (or super-values). The IMPACS system 200 may also have to maintain other databases relating to modalities $M_n$ and/or slave PACS servers $110_n$ for tag rewrites. These maps can be provided using a relational database. The rules engine 440 will apply the rules it is provided overwriting the DICOM tags for a requested image before it returns the image to the requesting user when needed. Again, before saving an image, it can access the correct tag for the modality $M_n$ or slave PACS server 110 and update the tags before writing to the slave PACS server 110.

FIG. 19 in particular, shows how tags can be modified either when a modality $M_n$ saves an image into slave PACS server $110_n$ or vice versa when a workstation $WS_n$ accesses an image from slave PACS server 110.

When it comes to searching across images, the IMPACS system 200 can be programmed to override the tag values for the images being searched for with its custom values as set forth in its Tag Map/Override database 432, a process that is facilitated with the IMPACS system 200 having the Master DICOM tag database 430.

6.5.3 Security Framework 510

The map for the security frameworks 510 used by the various slave PACS servers 110$_n$ and the roles and/or super-identities to be created to permit access to the unification layer 400 were discussed above. There are two broad issues the IMPACS system 200 has to be configured for to implement proper security at both the emulation layer 300 and unification layer 400:

User Authentication. The IMPACS system 200 should authenticate any user $U_n$ logging into it either in emulation mode 300 or unification mode 400 before he/she can be permitted to access any of its functions.

Image Permissioning. Each slave PACS server 110 can determine and control which images an authenticated user $U_n$ within its own framework can access. However, when the IMPACS system 200 is operating in unification mode 400 provided by the unification layer 400 no slave PACS server 110 has any knowledge of users $U_n$ at the IMPACS system 200 level and their access permissions. In general, there will be no user $U_n$ in any slave PACS server 110 that is permissioned to access any other slave PACS server 110. The IMPACS system 200 can be configured to provide a separate framework for user permissioning in this case and determine which images each of these new users U can see across the slave PACS servers 110$_n$ connected to the IMPACS system 200.

How the IMPACS system 200 handles both these issues is described in detail below.

6.5.3.1 Creation of New Roles and Permissions

The unification of images across the slave PACS servers 110$_n$ made possible by the IMPACS system 200 requires a richer system of permissioning. This is because the IMPACS system 200 now allows greater access privileges than the slave PACS servers 110$_n$ individually can provide.

Thus for example, a doctor within hospital A may have access to patient Jack McCoy's $P_1$ records as well as those of any patient in Hospital A. However, he may not have access to any images from Hospital B. When given a super-identity in the IMPACS system 200, this doctor will not have access to Jack McCoy's $P_1$ images in Hospital B because his identity by default is not authorized to see images from Hospital B. If our doctor in Hospital A is permissioned by the patient McCoy $P_1$ to see all his images across hospitals, we need to verify and associate these extended permissions with the doctor's super-identity. Then, any search by that doctor on the patient $P_n$ will retrieve the latter's images across all hospitals. Alternatively, if hospitals A and B merge so that all doctors in either hospital are authorized to see the images of all patients in the unified hospital, then the doctor will be permissioned at the IMPACS system 200 to see all images in Hospital A's and B's slave PACS servers 110$_n$. In such an event, he would have automatic access to patient McCoy's $P_1$ images in both hospitals without any additional permission being needed from the patient, though not from a third hospital (say Hospital C) unless explicitly authorized.

One can easily understand that there will be additional identities such as nurse, operator, etc. applicable to a single hospital that will have to be extended now across hospitals. The IMPACS system 200 will have to create some new super-roles to support an extension of these roles and manage the permissioning of the same. These roles could include the patient $P_n$ (who today almost never has direct access to hospital PACS servers) as well making it possible for him to see his images directly off the hospital's PACS system 100/server 110 instead of relying on a DVD-ROM of images.

To establish and track these new roles and the authentication needed for the same, the IMPACS system 200 will establish a User//Role/Group Map 518 that is designed to track the various clients that can access the IMPACS system 200 system and the access levels they will have for images in the IMPACS system 200 system once they are authenticated. The User/Role/Group Map 518 can be implemented with a relational database.

As illustrated in FIG. 21, this User/Role/Group map 518 will have the authentication credentials for these various clients and will be consulted every time any client attempts to authenticate to the IMPACS system 200 using one of these newly created roles or identities. In addition, to the extent that some of these users/roles/groups correspond to differing identities in the slave PACS servers 110$_n$ (such as for example Nurse DoeBuck in our earlier example corresponding to Nurse Doe in one hospital and Nurse Buck in another), the User/Role/Group map 518 will store these various identities and their credentials organized by slave PACS server 110$_n$.

6.5.3.2 Security Modes 500 for Authentication

With reference to FIG. 22, the IMPACS system 200 can be configured to handle authentication using two distinct security frameworks:

Flow-Through Security (FTS) provided by an FTS engine 512. In Flow-Through Security 512 the IMPACS system 200 operates to authenticate an agent (user $U_n$ or modality $M_n$) by simply sending his credentials to its associated slave PACS server 110$_n$ and delegating the latter to perform the authentication function. This assumes of course that the agent can be reliably associated with a specific slave PACS server 110$_n$. This is the primary mode of authentication when the IMPACS system 200 provides its emulation mode 300 functions and has the necessary configuration maps set up as described above for this purpose. For a modality this is typically all that is needed. However, when a user authenticates only with his local PACS server 110$_n$, security needs dictate that all searches done by this user $U_n$ be handled directly by his slave PACS 110$_n$ and not the IMPACS system 200 because the IMPACS system 200 cannot determine exactly what in the slave PACS 110$_n$ he is authorized to see. Such a user $U_n$ cannot access the DICOM tag database 430 in the IMPACS system 200 for any of his searches because the IMPACS system 200 has no way of determining his access level which is handled entirely by the slave PACS 110$_n$. However, the IMPACS system 200 will step in to actually transport the images that the slave PACS 110$_n$ permits the user $U_n$ to see, and as such can perform many of its additional functions such as DICOM tag rewrites, etc.

IMPACS-Managed Security (IMS) provided by an IMS engine 514. For IMPACS-Managed Security, when a new agent is created within the IMPACS system 200, no slave PACS server 110$_n$ has any knowledge of this user $U_n$. In this case, the IMPACS system 200 manages the entire authentication process for the user $U_n$. The IMPACS system 200 provides unification layer functionality 400 only to such users $U_n$. The DICOM tag database 430 set up by the IMPACS 200 as described above lists the UIDs of all the images from each of the slave PACS servers 110$_n$ in the IMPACS system 200. The IMS engine 514 links every DICOM image stored in the various PACS servers 110$_n$ (or study or series depending on the granularity desired) via master DICOM tag database 430 to a list of users/roles/groups created by the IMPACS system 200 who are permissioned for the same. It also specifies in the list of users/roles/groups what these permissions are (read, edit etc.). The IMPACS system 200 can create such links only for users U$_n$ that it creates and manages because only these users U$_n$ can be assigned permissions based on its DICOM image database 430. These users U$_n$ (and only these users U$_n$, all of whom operate with IMS) can search the IMPACS DICOM tag database 430 and their searches will automatically be confined to only those images across all the slave PACS servers 110$_n$ they are permissioned to see. This security framework is addressed in more detail in the pending patent application Ser. No. 16/037,249, where the DICOM objects (studies, series or images) correspond to Transactions and the users/roles to Agents.

In most implementations, user authentication with flow-through security should be avoided at the IMPACS level 200, even though it can be implemented. User workstations WS$_n$ are rarely static and frequent changes in network addresses, etc. are typical. As such, a user workstation WS$_n$ cannot often be uniquely identified (unlike a fixed modality M$_n$) which means such users U$_n$ under the emulation mode 300 will not be permitted access at all. For completeness, the IMPACS system 200 can also be configured to associate a local slave PACS server 110 user identity with one of its new roles created as described above to thereby convert an FTS authenticated user after login into an IMS-managed identity.

Implementing the IMS authorization framework for IMPACS-created users U$_n$ can be done with a commercially available authentication framework (OAuth2, LDAP etc.) or with an equivalent custom framework. The IMPACS system 200 can also be set up to connect seamlessly to an external authentication framework (such as LDAP) and create its users, roles etc. on this framework. Such a framework might already be in place for example in a larger medical system under which the IMPACS system 200 may have to operate.

6.5.3.3 Image Permissioning

Authentication of a user U$_n$ does not in itself allow the IMPACS system 200 to identify just what images he is authorized to see. To that end, the IMPACS system 200 has to be be configured to associate with every image (or study or series as desired) in its tag DICOM tag database 430 the list of users/roles/groups in its map 518 that are permissioned for that object and just what those permissions are. Given that the DICOM tags will be maintained in a relational database 430, the association of the users/roles/groups to the DICOM objects is an elaborate database many-to-one link.

The IMPACS system 200 will relate entities in its User/Role/Group map 518 to their permissioned images (along with the type of permissions that they are provided for the same) in the DICOM image tag database 430 by creating an Image Permissions Map 520 as illustrated in FIG. 23. The Image Permissions Map 520 can be easily implemented as a many-to-many relational database table.

The actual implementation of the user/role/group objects can (and usually will) be part of a much more extensive permissions hierarchy setup that the IMPACS system 200 may not even implement directly. All that the IMPACS system 200 requires for its function is that it can filter out from the DICOM tag database 430 all the image entries that are visible to a specific user or role U$_i$. Thus, for a specific DICOM object Di in the database, with a permission association list A$_j$ (which is a list of specific permissions such as read, write, edit etc), what needs to be implemented for the IMPACS system 200 to work correctly is the database function:

Has-Permission(User=U$_i$,

Object=D$_j$,

ObjectPermissions=A$_j$) (6.i)

which returns True if the user has the permissions and False otherwise.

For the IMPACS system 200 to work as intended, this function should be implemented either at the level of the IMPACS system 200 itself or by accessing an external permissions framework. To manage authorizations for image access by patients, doctors and other such roles, the IMPACS system 200 will rely on a more elaborate authorization scheme as provided by a more comprehensive process engine such as the Process Knowledge Engine disclosed in the pending patent application Ser. No. 16/037, 249.

6.5.4 Extensible Process Engine 610

As addressed above, implementing the IMPACS system 200 includes:
- determining the slave PACS servers 110$_n$ that are part of its network and understanding how to connect to them.
- establishing a database of DICOM tags 430 for easy searching across slave servers.
- unifying patient and other DICOM information with patient super-identities using the map 431 for this purpose to allow for seamless combination of patient data across the slave PACS servers 110$_n$, as well as rewriting tag data in returned images.
- creating special user/role/group identities using map 518 for this purpose to allow access to the enhanced capabilities provided by the IMPACS system 200 and handle their authentication and image permissioning (via image permissions map 520).

The process engine 610 (which is part of the IMPACS brain/control engine 201) of the IMPACS system 200 implements the IMPACS system 200's various functions both at the emulation 300 and unification 400 layers and allows it to behave like a standalone PACS server 110 from the perspective of a user U$_n$ or modality M$_n$. Some of the specifics regarding the execution of the above steps have already been addressed in the relevant sections. Discussed further below are:
- how the actual PACS server 110 interface functions are provided by the IMPACS system 200 interacting with the various slave PACS servers 110$_n$,
- how the IMPACS system 200 can provide considerable additional capabilities beyond basic DICOM.

6.5.4.1 Implementing PACS Server 110 Capabilities

Where it comes to implementing its PACS server 110 capabilities, the IMPACS system 200 can be viewed as being made up of three parts as shown in FIG. 24:
- A standalone PACS server 110 that has all the functions of a regular PACS server 110. We shall refer to this PACS server 110 as the IMPACS' self-PACS 710. This self-PACS 710 will maintain its own image databases, tag maps and other image information.

A network of slave PACS servers $110_n$ that are distinct from the IMPACS' 200 self-PACS 710. These slave PACS servers $110_n$ are external to the IMPACS system 200 unlike the self-PACS 710.

An extensible process engine 610 (which is the process part of the IMPACS system 200's overall brain/control engine 201) that controls both the self-PACS 710 as well as the network of connected slaves PACS servers $110_n$.

FIG. 24 shows the above three parts of IMPACS system 200 and particularly its self PACS 710.

When modalities $M_n$ or workstations $WS_n$ are connected directly to the IMPACS system 200 without being associated with any of the underlying slave PACS servers $110_n$ (which makes them clients under the unification layer 400 and reflected as such in the modality identity map 310), they operate only with IMPACS level credentials and tags. As such, all modalities $M_n$ connecting in this context operate with patient super-identities known to the IMPACS system 200 in the patient super-identity map 431. Images stored by such modalities $M_n$ will be saved in the self-PACS 710 which the IMPACS system 200 manages. The tags of the self-PACS 710 are managed by the IMPACS system 200 and as such are always kept in sync with the DICOM tag databases 430 maintained by its brain/control engine 201/ process engine 610.

Importantly, it should be noted that the IMPACS system 200 will have to maintain its modality identity map 310 even for modalities $M_n$ that connect directly to the IMPACS system 200 because it has to authenticate all such modalities. Put differently, any modalities connected to the IMPACS system 200 directly without having an associated slave PACS server $110_n$ will be connected to the IMPACS system 200's own self-PACS 710 and will be connecting to the latter in "emulation" mode.

For all practical purposes, the self-PACS 710 behaves like a slave PACS server 110 in the IMPACS system 200 context. As such, going forward, when we refer to the slave PACS servers $110_n$, they should be assumed to include the self-PACS 710 as well unless explicitly indicated otherwise. The DICOM tag databases 430, user maps and other implementation issues discussed earlier in this section relate only to the IMPACS' process brain/control engine 201 (and the process engine 610 part of this brain).

It may be possible to configure the IMPACS system 200 without a self-PACS 710 if certain functions such as image storage (under unification mode 400) are not needed. However, it is preferable to set up the self-PACS 710 and configure it for proper operation.

Implementing the PACS server 110 functions such as the retrieval and storage of images by the IMPACS system 200 process brain is relatively straightforward. This is because the IMPACS system 200 itself is not providing these functions—the slave PACS servers $110_n$ are (with the self-PACS 710 being one of the "slaves" as well). The syntax of the DICOM function calls is governed by the DICOM standard which both the IMPACS system 200 and the slave PACS servers $110_n$ observe. Thus, the instructions received by the IMPACS system 200 can be transmitted to the corresponding slave PACS server 110 that is to perform the function with some relatively simple translation of the actual function syntax at the IMPACS system 200 level. Put differently, in implementing the basic DICOM functions, the IMPACS system 200 acts primarily like a traffic policeman, routing the various DICOM calls it receives to the appropriate slave PACS servers 110 and transmitting back the results.

When the IMPACS system 200 provides any form of image storage or modification either through its emulation functions 300 or saving into its self-PACS 710 under unification mode 400, it has to update its DICOM tag database 430 to reflect the new images and tags. A flow chart of how the IMPACS system 200 stores images into its network of attached slave PACS servers $110_n$ including its Self PACS 710 is shown in FIG. 25.

When a new image is stored into a slave PACS server 110 by the IMPACS system 200 with its emulation layer 300, the latter will automatically update its DICOM tag databases 430 which means that the slave PACS image data will be in sync with that in the IMPACS system 200. Clearly images saved into the self-PACS 710 are always in sync. New images stored into a slave PACS 110 by modalities $M_n$ the IMPACS system 200 is not aware of can be recognized only by polling the slave PACS server 110 image database for changes and updating the Master DICOM tag database 430 and/or the Tag map/Override database 432 as needed when such storage occurs.

The examples below show particular implementation features using pseudo-DICOM function call syntax to highlight what exactly is being done.

Example 1

This example is discussed with reference to FIG. 26. Consider the situation where an image is requested from the IMPACS system 200 (step 1). The request is made by a user authenticating with IMPACS system 200 identity $U_i$ who provides password ABCDE and it is to obtain a specific study $S_j$ (pertaining to patient Jack McCoy with super-identity JMC1151 from IMPACS server VP1. Given that this is a user who is operating with his super-identity, the IMPACS system 200 knows about his permissions and manages security at the IMPACS system 200 level itself.

In terms of a function call this request could be written as:

DICOM-Get-Object(RequestingUser=$U_i$,

RequestingUserPassword=ABCDE,

Patient=JMC1151,

Study=$S_j$,

Location=$VP1$) (6.ii)

Faced with this request, the IMPACS system 200 will do the following in order:

1. Check if the user $U_i$ is allowed to connect to the IMPACS system 200 by authenticating with the password ABCDE provided (steps 1 and 2). Such authentication might be done by the IMPACS system 200 itself using standard protocols using its user/role/group map 518 or by other authorization servers to which the IMPACS system 200 might be tied if it is part of a larger medical records system.
2. Check that the requesting user $U_i$ has the credentials to access the study step 1904, 1905).

This can be implemented as a function:

DICOM-Authenticate-User-For-Study
   (RequestingUser=$U_i$,

Patient=JMC1151,

Study=$S_j$) (6.iii)

that will return True to authorize access and False if not, checking the Image Permissions Map 520 for this purpose.

If the user $U_i$ is a doctor who has been authorized by the patient Jack McCoy to see all his images, the above request will return True. If the IMPACS system 200 receives an affirmative response, it allows the request to proceed to the next steps and aborts it otherwise.

3. Find the slave PACS server 110 that contains the requested DICOM object when we have an authenticated request (step 6). For this, the IMPACS system 200 will consult its DICOM tag database 430 which stores an extra attribute defining which slave PACS server 110 contains the said object. In function terms, the IMPACS 200 executes the following function that it has implemented:

DICOM-Locate-SlavePACS-for-DICOM-Object
(Patient=JMC1151,

Study=$S_j$) (6.iv)

Assume that this function call returns a value of $SP_k$ which identifies the slave PACS server 110 in which the image is located.

4. Get the appropriate authentication credentials (step 7) for the requesting user for the Slave PACS server 110 in which the image is consulting the user/role/group map 518 for this purpose if needed:

DICOM-Get-Authentication-For-User
(RequestingUser=JMC1151,

Location=$SP_k$) (6.v)

This call will return the username for the requesting user in the slave PACS server $110_n$ as well as his password. Assume that this call returns Username=DOCTORp and Password=XXYYZ. This step will be unnecessary if the slave PACS server 110 trusts the IMPACS system 200 to perform all the required authentication and provides blanket access for the IMPACS system 200 to access all images deliverable to the IMPACS system 200.

5. Get the patient identifier corresponding to the object requested in the slave PACS server 110 if needed (step 7). This is an optional step that may not be required if UIDs are used for the Study, Series or Instance requested because these are globally unique already by the DICOM standard.

DICOM-Match-Patient-ID-To-SlavePACS
(Patient=JMC1151,

SlavePACS=$SP_k$) (6.vi)

In this example, assume the above call returns 71522 as the identifier for our patient.

6. Format and dispatch the DICOM request for the requested object (step 8). The DICOM request to the slave PACS can simply be sent as:

DICOM-Get-Object(RequestingUser=DOCTORp,

RequestingUserPassword=XXYYZ,

Patient=71522,Study=$S_j$,

Location=$SP_k$) (6.vii)

7. Send the requested data back from the slave PACS server 110 with the appropriate tag rewrites as needed to the requesting workstation (step 9). The user workstation WS in this context will never connect to the slave PACS server 110 directly but only to the IMPACS system 200 itself.

Example 2

The IMPACS VP1 might also be queried for all studies pertaining to a given patient JMC1151 over some period say from Oct. 11, 2017 to Oct. 11, 2019 as permitted by DICOM. In this case again, the user is operating with an IMPACS system 200 provided super-identity. This example is discussed with reference to the flow chart provided in FIG. 27.

The query in this case can be represented as:

DICOM-Filter-Objects(RequestingUser=$U_i$,

RequestingUserPassword=ABCDE,

Patient=JMC1151,

Location=$VP1$,

DateRange=[10/11/2017,10/11/2019]) (6.viii)

The IMPACS system 200 will now have to contend with the fact that patient JMC1151 is a super-identity for Jack McCoy that has no analog in any slave PACS server 110. To execute this query, the IMPACS system 200 does the following, after authenticating the user in question:

1. Search its internal DICOM tag database 430 to find all the images that satisfy this query, or
2. Query all of the slave PACS servers $110_n$ to dynamically generate the requested list of images. To perform a dynamic query, the IMPACS system 200 will:
   (a) Determine JMC1151's list of slave PACS servers $110_n$ identities which in our case are 71522 in Hospital A and 61894 in Hospital B, and the slave PACS servers' $110_n$ details which are linked to these identities.
   (b) Obtain the slave PACS servers' $110_n$ locations from the details provided in the prior query. Assume these are $SP_a$ and $SP_b$ for Hospitals A and B respectively.
   (c) Format and dispatch the requests appropriately for each slave PACS server 110 fixing the patient identity as required. So for Hospital A, the generated query would be:

DICOM-Filter-Objects(Patient=71522,

Location=$SP_a$,

DateRange=[10/11/2017,10/11/2019]) (6.ix)

and for Hospital B it would be:

DICOM-Filter-Objects(Patient=61894,

Location=$SP_b$,

DateRange=[10/11/2017,10/11/2019]) (6.x)

Importantly, the user identifier $U_i$ and the password ABCDE cannot be passed into the slave PACS servers $110_n$ because they are not even aware of the existence of the IMPACS system 200 identity $U_i$ which is JMC1151 here.
   (d) Collate the results from the above two queries (which follow standard DICOM formats) into a unified result list for further processing. Importantly, the list returned will have additional attributes listing which slave PACS server $110_n$ contains the image.

(e) Obtain the UIDs of the images from the collated list and check from the IMPACS-maintained DICOM tag database 430 and user/role/group map 518 and image permissions map 520 which of these images our user $U_i$ has permission to see. Create a list of images that both satisfy our user's query and whose results he is permissioned to see.

(f) Return the filtered list to the user. The query will not show any results he is not permissioned to see.

3. With the list of images (and slave PACS servers $110_n$ where they are stored) obtained from either of the steps above, the IMPACS system 200 can now format the request for each image trivially as in the previous example. When delivering the actual image, any tag rewrites can be performed on the fly.

Given that the IMPACS system 200 maintains databases of DICOM tags 430 as well as an image permissions map 520 for images from all the slave PACS servers $110_n$, it is likely that the above queries can be handled entirely by the IMPACS system 200 itself without any access being made to the slave PACS server 110 except for the final retrieval of the images.

In both of the above examples the IMPACS system 200 performed the same set of steps which are:
1. parsing a standard DICOM request made to it by a user $U_n$ or modality $M_n$.
2. determining from the request the correct slave PACS server(s) $110_n$ that need to be involved in its fulfillment using its internal databases for that purpose.
3. obtaining the correct object and patient identifiers along with the right user credentials as needed for each involved slave PACS server $110_n$.
4. formatting the request properly for each slave PACS server 110 which, for the most part, merely involves rewriting the same with the right identifiers for that slave PACS server 110.
5. gathering the results, changing or fixing tags as needed, and delivering them to the requesting user $U_n$.

The important thing to note is the structure of the query is already set by the DICOM standard which both the slave PACS server 110 and IMPACS system 200 implement. All that the IMPACS system 200 does is rewrite these queries into a form appropriate for each slave PACS server 110 using its internal databases and logic for that purpose as configured into its process brain/control engine 201.

6.5.4.2 Implementing Process Extension Layer 600

The IMPACS system 200 could also alter the images delivered to or obtained from the slave PACS server 110 by an agent, either by rewriting certain DICOM tags, converting the image formats or performing some other such transformation based on extensible rules set up within the IMPACS system 200 for this purpose. Thus, a modality $M_n$ that does not fill in specific DICOM tags might have such tags added by the IMPACS system 200 before delivery to the slave PACS server 110 if such a permanent tag is desired in the actual stored image. Again, an image with missing or incorrect tags might have its tags overwritten by the IMPACS system 200 using its Tag Map/Override database 432 without altering the actual stored image. In this context, the IMPACS system 200 behaves as a special case of the more general process knowledge engine discussed at length in the pending patent application Ser. No. 16/037,249. The IMPACS system 200 can be configured with a process specification language in which one could define multiple rules and its process knowledge engine can implement these rules for additional activities beyond its DICOM functions.

The rewriting of tags, which is a general issue that the IMPACS system 200 needs to address because it overrides the PatientID tag field, can be implemented as shown in FIG. 19 which illustrates both dynamic tag modification for image access and permanent tag modification for image storage.

When an image is accessed, the IMPACS system 200 checks the returned image's Instance UID against its internal Tag map/Override database 432 using the logic provided by its Rules Engine 440 as described above. If a specific tag needs to be overwritten with one from the IMPACS' data transformation tag database 432, the IMPACS system 200 can update the tag of the image returned before passing it onto the requesting agent. The same logic will apply in reverse if a tag has to be altered for a new image created by a modality $M_n$. In the latter case, the tag transformation associations will be maintained for each modality $M_n$ at the IMPACS system 200 level, with an association between the modality identity map database 310 and the tag map override database 432. Based on the modality generating the image, the tag will be transformed before delivery for writing to the slave PACS server 110.

Not all tags can be re-written by the IMPACS system 200 when it comes to passing through images from a modality $M_n$ to be saved into a slave PACS server 110. Many of the tags in a DICOM image are set by the PACS server 110 itself when the image is saved (like the study, instance and series UIDs for example) and should not be changed. In general, when it comes to saving images, the IMPACS system 200 will rewrite only custom DICOM tags (including ones that it has created for specific image search filters) or other non-critical tags (such as for example the InstitutionName tag in some situations) before transmission of an image to the associated slave PACS server 110.

Where it comes to delivering images that have been accessed, the IMPACS system 200 may overwrite the PatientID tag if in unification mode 400 to permit consistent image viewing for a given patient across slave PACS servers $110_n$. Such overwriting is generally not essential but may be required in certain deployments. However, image UID tags for the image instance, study and series should not, in general, be rewritten.

6.5.4.3 Creating Audit Trails

Since the IMPACS system 200 has to manage authentication for all clients including users, modalities, workstations and patients using its respective maps 518, 310, 320 and 431, it is already configured to track access of any slave PACS server 110 by any of these client entities. As such, the IMPACS system 200 by simply logging such access, can provide an automatic audit trail of every access and every use of any DICOM resource by any user $U_n$, workstation $WS_n$ or modality $M_n$ or patient $P_n$. In addition, it provides a layer of authentication security that is over and above that provided by any slave PACS server $110_n$ and that can be further enhanced as needed without altering the security models used by the slave servers $110_n$.

6.5.4.4 Transporting the Image Objects Between Agents

After the authentication, image access and process extensions are completed, the IMPACS system 200 can seamlessly transport the queried/requested/stored image objects or groups to the client device, slave storage PACS server $110_n$ or modality $M_n$ as appropriate to implement the full PACS server 110 functionality. Thus for example, the IMPACS system 200 may obtain the images from the slave PACS server $110_n$ and deliver the images to the client. Again, it might receive the image from the acquiring modality $M_n$ and send it the appropriate slave PACS server $110_n$ for storage managing all the confirmations and messaging for the same. In all these cases, the IMPACS system 200 will act as the supervising intermediary that manages the process providing all the control and oversight for this. In general, the accessing client (modality $M_n$, workstation $WS_n$ or other entity) will not know that the slave PACS servers $110_n$ even exist because the IMPACS system 200 effectively subsumes their functionality.

The IMPACS system 200 even at this level can be extended to perform certain optimizations because of its process intelligence. It can for example detect the nature of the querying device and apply image compression or transformation as appropriate to permit the quickest delivery of the image. Based on the capabilities of the requesting device, it can apply intelligent algorithms to permit better viewing. Thus for example, the IMPACS system 200 could detect that the querying device is a mobile telephone and apply both compression and image enhancement to the returned image so that it is delivered quickly and the image view on the poorer quality (relative to medical viewers) phone screen is optimized.

Thus, the IMPACS system 200 thanks to its process brain/control engine 201, is a powerful and extensible system for managing the DICOM process flow. The various maps that are maintained by the IMPACS system 200 are the data that define what its brain/control engine 201 needs to perform its many functions. Actually performing these functions requires that the IMPACS system 200 be programmed for these capabilities as discussed herein. These programs along with the logic needed to execute them, collectively make up the IMPACS' brain/control engine 201, and allow it to provide the IMPACS system 200's PACS server interface 210. All of this functionality makes up the entirety of the IMPACS system 200.

6.6 Using the IMPACS System 200

Addressed below are various use scenarios and associated flow charts and diagrams.

6.6.1 Image Access for Client/Patient $P_n$/Workstation $WS_n$

A client or workstation WS requesting PACS images from a variety of slave PACS servers $110_n$ would connect directly to the IMPACS system 200 and the IMPACS system 200 would perform the following actions:

1. Authenticate as his chosen agent/role into the IMPACS system 200 using standard protocols. When the client is a user U, for reasons discussed earlier, authentication is generally with IMPACS system 200 supplied credentials because the role identification might otherwise be impossible. The IMPACS system 200 can be configured to support most publicly available security protocols. While it may use some of the same protocols in use at one or more of its slave servers $110_n$ the IMPACS system 200 can have a much richer security framework 510 than in the slave PACS servers $110_n$ because the IMPACS system 200 provides a level of access across slave servers $110_n$ which the latter do not permit. To permit the added functionality of the IMPACS system 200, new roles/permissions will likely have to be created as discussed earlier using the user/role/group map 518.

2. Query the studies/series/images etc. that his role has access to. The IMPACS system 200 will seamlessly determine which subset of data from all the slave PACS servers $110_n$ can be made available for this agent to query and/or see by referring to its internal master DICOM tag database 430 and Image permissions map 520 which provides the permission matrix for a given image and its a user from the user/role/group map 518. It may also query the slave PACS servers 110 as needed for additional tag data.

3. Obtain and Display specific images or image groups to the software used by him for viewing the DICOM images. The IMPACS system 200 will seamlessly access the requested images from the slave PACS servers 110 providing the appropriate agent-specific security credentials to the slave servers 110 and deliver them to the client.

For a slave PACS server 110 user $U_n$ accessing the IMPACS' 200 emulation layer 300 without having an IMPACS system 200 created identity, the above steps are similar, but the query for the user's images will be done only at the slave PACS server 110 rather than at the IMPACS tag database 430.

Put differently, the IMPACS system 200 will in all respects behave like a "regular" PACS server 110 to a user $U_n$. Under the hood however, in unification mode 400, the IMPACS system 200 operates to combine the data from a plurality of slave PACS servers 110 in terms of patient identities, security protocols, access roles etc. without having to copy and itself store the actual (large) images from the slave PACS servers $110_n$ or modify them in any way. In emulation mode 300, it is behaving like one of its component slave PACS servers $110_n$ and the very existence of the IMPACS system 200 is something that the connected modalities $M_n$ and/or workstations $WS_n$ are generally totally unaware of.

6.6.2 Target Store for a Modality $M_n$

A modality $M_n$ that uses the IMPACS system 200 as the main PACS store in emulation mode 300 will simply continue to operate as it did before except that it will connect to the IMPACS system 200 instead of its local PACS server 110. The local PACS server 110 is now one of the slave servers $110_n$ within the IMPACS framework 200. With reference to FIGS. 28 and 29, consider a modality $M_n$ such as an MRI machine with Hardware Address HA112 in Operating Room 21 in Hospital A which was originally connected to the hospital PACS server $110_a$. Assume now that this PACS server becomes a slave PACS server 110 to the IMPACS system 200 and that the modality $M_n$ is connected directly to the IMPACS system 200 through its PACS server interface 210. When the modality $M_n$ sends an image to be stored now to the IMPACS system 200, for patient Jack McCoy, with his Hospital A patient identity of 71522, the IMPACS system 200 will do all of the following in order:

1. Identify and authenticate the modality $M_n$ sending the image by using its hardware address, authentication credentials or equivalent unique identifier using the internal databases (such as the modality map 310) that were created for this purpose (Step 1). In this case the hardware address for the modality is HA112.

2. Provided the modality $M_n$ is known (Step 2), relate the modality HA112 to its appropriate hospital and location/PACS server 110 (Step 3) which in our case would be Hospital A and Operating Room 21 using the internal modality maps 310 created for this purpose during configuration.

3. Map the local patient identity provided by the modality $M_n$ using the patient super-identity map 431 to the appropriate IMPACS identity (Step 4). In this case, patient identifier 71522 (for Hospital A) would be identified as referring to identity JMC1151 that was set up within the IMPACS system 200—this search is possible because we know which hospital and which identity to search for in our super-identity map 431. In the event that the patient does not have an IMPACS super-identity, the IMPACS system 200 can be configured to set one up for this patient updating its super-identity map 431 appropriately (Step 5).

We need the patient super-identity for the user referenced by this image in order to update IMPACS tag databases 430 and image permission databases 520 with the appropriate image image permissions for that patient. If we do not have such a super-identity, the only possible access to the image will be in emulation mode 300.

4. Determine the authentication protocols to use to access the slave PACS server $110_a$ in Hospital A. This can be done with reference to the modality map 310 for the slave PACS 110 as related to the modality $M_n$ (Step 6).
5. Authenticate to the slave PACS server $110_a$ in Hospital A as MRI machine in Operating Room 21 would (Step 7).
6. Deliver the image to the slave PACS server $110_a$ from the MRI machine once the authentication is performed successfully (Step 8). The image will still have the PatientID tag set to 71522.
7. Update the IMPACS DICOM tags in the IMPACS database 430 to reflect the new images stored so that they will be visible in future searches of the IMPACS system 200 (Step 9). The master DICOM tag database 430 will reflect that these images will be part of the record of user JMC1151 and as such visible to any agent that has view access to JMC1151's images.

In the examples above while the IMPACS system 200 has to do a lot of work to map patient identities, modalities, etc. to the appropriate slave PACS server 110. Once that work is done the actual access of images, queries etc. is relatively simple because the IMPACS system 200 will be operating using the DICOM standard with some translations of the function calls made to the various slave PACS servers 110. In performing these functions, the IMPACS system 200 can fully satisfy all the security requirements moreover of every slave PACS server $110_n$.

Even if the IMPACS system 200 were to route image storage requests into the slave PACS servers $110_n$ for all its connected modalities $M_n$, it could also simultaneously store images from these modalities $M_n$ into another slave PACS server 110 but using newly-created IMPACS-level patient identities. This will permit a provider with multiple archaic PACS servers $110_n$ to create images in this new PACS server 110 using the new unified IMPACS identities while continuing to operate with the old PACS servers $110_n$ as well over a transition period.

6.7 Progressive Implementation with IMPACS System 200 Hierarchies

In an embodiment, and as addressed further below, the IMPACS system 200 can be implemented in a progressive, hierarchical fashion that can scale across numerous slave PACS servers $110_n$ without significantly impacting the complexity of the implementation or reducing its efficiency. Each slave PACS server 110 can belong to multiple IMPACS systems $200_n$ with almost no additional overhead. Further, each IMPACS system 200 itself through its PACS server interface 210, can become a slave PACS server 110 to another IMPACS system 200.

6.7.1 Multiple IMPACS System 200 Memberships for Single Slave PACS Server 110

The IMPACS system 200 is a lightweight layer intended to ensure interoperability across PACS servers $110_n$. As such, the same slave PACS server 110 can belong to multiple IMPACS systems $200_n$ without any extra overhead or modification. In fact, two different IMPACS systems $200a$ and $200_b$ can create their own unification tags for patients but still use data from the same underlying slave PACS servers $110_n$. This should prove a powerful mechanism to permit custom types of unification. Thus, for example, one might have an IMPACS system 200 that unifies only the data from patients of certain ethnicities or with certain ailments with extra logic for such patient filtration being provided by other external methodologies. Again, we might have a doctor/patient centric IMPACS system $200a$ that provides full patient unification, but another research focused IMPACS system $200b$ that provides the same unification while anonymizing all specifically identifiable patient data. In technical terms, all of these IMPACS systems $200_n$ can run off a master DICOM tag database 430 that is created just once from the connected slave PACS servers $110_n$. The only changes that may be required to support these different IMPACS system 200 instances would be different filters applied to the master DICOM tag database 430 and different image delivery algorithms (with or without anonymization etc.) to permit selective viewing. Put differently, each of these multiple IMPACS system 200 instances will have essentially identical maps and data, but will differ in the programming of each of their process brains/control engines 201.

6.7.2 IMPACS System 200 as Member of Another IMPACS System 200

The IMPACS system 200 is a full-fledged PACS server 110 in its own right, both in emulation mode 300 and in unification mode 400. As such, any IMPACS system 200 through its PACS server interface 210 can itself serve as a slave PACS server 110 within a higher level IMPACS system 200.

With reference to FIG. 30, slave PACS servers $110_a$, $110_b$ and $110_c$ are unified by the Level 0 (or the lowest level) IMPACS system $200a$. Slave PACS servers $110_d$ and $110_e$ are unified by another Level 0 IMPACS system $200_b$. These two IMPACS systems $200a$ and $200b$ in turn are unified by a higher level (Level 1) IMPACS server $200c$. Ideally, the Level 1 IMPACS server $200c$ would use the unified DICOM patient tags generated by the respective Level 0 IMPACS servers $200a$ and $200b$ and in turn create higher level, and possibly new, patient tags to provide unification at Level 1 across the two Level 0 IMPACS servers $200_n$. IMPACS server $200c$ can also be used to unify the Level 0 IMPACS with one or more slave PACS servers $110_n$ such as PACS server $110_f$.

This functionality can be replicated again if needed with one or more Level 1 IMPACS servers being unified by a Level 2 IMPACS server etc. creating a natural unification hierarchy. The powerful feature is that an IMPACS server 200 at any level can be accessed both by its modalities $M_n$ and workstations $WS_n$/users $U_n$ as needed and can provide just the degree of unification it was intended to, along with all the emulation functions 300 it was configured for. Accessing a higher level IMPACS system 200 (at Level 1 instead of Level 0 for example) simply expands the degree of unification and emulation provided.

The beauty of the hierarchical IMPACS system 200 implementation is that it is organized intuitively for efficiency. Turning to FIG. 31, consider a group of 4 local hospitals A, B, C and D that operate with different PACS servers $110_a$, $110_b$, $110_c$ and $110_d$ respectively and decide to merge. For these providers, we can implement a Level 0 IMPACS server $200_{a0}$ to unify these PACS servers $110_n$ which become slaves to the Level 0 IMPACS $200_{a0}$. Now, assume some of these merged hospital groups form a single county-wide hospital group. They can in turn merge their Level 0 IMPACS servers $200_{a0}$ and $200_{b0}$ into a Level 1 IMPACS server $200_{p1}$ to which the Level 0 IMPACS systems $200_{n0}$ become slaves. If these hospitals cooperate to create a research IMPACS system 200, we can unify their Level 0 IMPACS servers $200_{n0}$ into a separate patient-anonymized Level 1 IMPACS server $200_{q1}$.

The hierarchical implementation of the IMPACS system 200 is possible even when only its emulation functions 300 are required. To permit this of course, every higher level IMPACS system 200 should have a copy of every modality $M_n$ connected to each lower level IMPACS server 200.

6.8 Non-DICOM Modalities $M_n$ and Non-PACS Storage

In discussing the extension layer functions 600 of the IMPACS system 200 above, we addressed the use of the IMPACS system 200 to enable new modalities $M_n$ for DICOM imaging, as well as to PACS-enable non-DICOM storage. These two features are discussed in more detail below.

6.8.1 Non-DICOM Modalities $M_n$

The cheap and ubiquitous availability of digital cameras, smart phones and computer webcams has made it very easy to use such devices for medical purposes. These consumer-grade devices are generally not certified for medical use. However, many doctors use images obtained from these sources to supplement their analysis of a patient. Thus, many dermatologists often take pictures of specific skin lesions using consumer-grade digital cameras. Yet others, such as otolaryngologists, use digital video cameras connected to their medical scopes to obtain full-motion video during their examination of a patient's pharynx, sinuses or other areas. The problem in using such user-centric, typically consumer-grade devices for medical image acquisition is that they cannot be incorporated into the standard medical imaging workflow which typically uses DICOM. As such, potentially helpful data about a patient are not easily accessible except through the capturing doctor's own custom process for the same. If these images could be added to the patient record within the hospital, ideally to the hospital's PACS server $110_n$ they could be incorporated into the medical workflow. However, uploading such images to the provider's PACS server $110_n$ while possible, is a difficult process with conventional systems for several reasons. A non-exhaustive list of these reasons is:

The images and the imaging device are not DICOM compliant. In fact, the images have tags defined by some other standard such as JPEG or camera RAW, and cannot easily be wrapped into DICOM format.

Converting the obtained images to DICOM involves both mapping current image tags to DICOM-equivalent tags, and adding numerous DICOM-specific tags in particular regarding the patient, the body parts imaged and the device. These tags typically have to be added manually which means the process is more error-prone.

Connecting the imaging device to the PACS server 110 is a laborious process especially given the need to add tags manually. Typically, the images will be downloaded to a hospital computer, the tags will be added and then the images have to be be uploaded to the PACS server 110.

The IMPACS system 200 can address all the above problems and be configured to seamlessly convert and incorporate images from non-DICOM devices into a DICOM-centric medical workflow. A general example of this process is illustrated in FIG. 32 and reference is made to the details in the figure below. To provide this functionality, the IMPACS system 200 can be configured to:

Register the image-acquiring device NDM-1 as a connected modality in its modality identity map 310 and/or a modality-user map 315. The process of registration will vary depending on the modality but will generally be more complex than for a standard DICOM modality. In some cases, the IMPACS system 200 can identify the modality reliably by its MAC address, serial number or other unique and detectable attributes and the modality identity map 310 will reflect these attributes to permit identification. In other cases, the modality may have to go through a custom registration procedure that will vary depending on the type of modality involved. The newly-registered "modality" would of course, have to be configured in the IMPACS system 200 as having a non-DICOM custom protocol for connection which means that the IMPACS system 200 will have to implement an application programming interface unique to this class of devices to manage its communication.

Thus, for example, if the "modality" in question is a single-user device such as a smart phone that needs to be DICOM-enabled, the modality identity map 310 in conjunction with the more extended modality-user-map 315 can be configured to uniquely identify both the device and the user that is using the device for image acquisition. These maps are designed to allow the IMPACS system 200 to reliably determine which slave PACS server 110 this device is to be associated with as well as which user identity should be used in that slave PACS 110 to tag the images acquired from this device. To actually perform these functions, a custom application will almost certainly have to be developed to run on the device in question. When this application is downloaded and run on the device, it will prompt for user credentials that it can transmit to the IMPACS system 200 for detection of the device/user. The device application will also be needed to securely transmit the device, user and image characteristics as well as provide the tools for the actual upload of the images.

Create a custom mapping that relates the tags of the images acquired by the new modality to equivalent DICOM tags when possible. Most image formats support some form of tagging and the IMPACS system 200 can itself fill in many of the modality and institutional tags from the configuration of the modality $M_n$ based on the modality identity map 310 and the Tag map/Override database 432. The IMPACS system 200 can also add custom tags to highlight the non-DICOM nature of the acquiring device for the images so that they can easily be filtered out if needed.

Upload selected images from the device into a holding area before final commitment into the appropriate slave PACS server 110. In this holding area, the doctor or technician obtaining the image can add some detail tags NDM-2 specifying the patient body part(s) that are being imaged and importantly, the patient identifier tag which in our case would ideally be the patient super-identity 431 maintained by the IMPACS system 200. Tags can include tags NDM-3 extracted from the image itself and tags NDM-4 auto filled by the IMPACS system 200 using its Tag map/Override database 432.

Combine the provided tags with those generated from the image itself using the custom mapping, extract the image data from the image (ex tags) and combine them into a legal DICOM image NDM-5 using an appropriate image converter NDM-10 if required.

Deliver the now DICOM-wrapped images for storage to a slave PACS server 110 designated for the modality $M_n$. This could well be the IMPACS' 200 own self-PACS 710.

Update the IMPACS DICOM tag 430 and Tag map/Override databases 432 if needed to reflect the newly stored images so that they will show up in future searches under the appropriate patient and with the right permissions.

6.8.2 Non-PACS Image Storage

There are many image formats that are increasingly part of the medical workflow for which a DICOM framework may not be appropriate. For example, slide scanners for the digital imaging of tissue samples in pathology operate with complex image formats and proprietary tag schemes that are not DICOM compliant. Again, medical video devices often generate huge files requiring their own dedicated storage. Such images may be part of the patient's medical record, but are not handled by the DICOM standard (yet) and may not even be stored on the provider's PACS server.

The IMPACS system 200 as a process engine is agnostic to the types of images being stored and searched for. As described above it can take a non-DICOM image from a device and wrap it into DICOM for storage into a PACS server. In addition, the IMPACS system 200 can also do this process backwards and PACS-enable a non-PACS image storage repository converting it into what we refer to as a pseudo-PACS 810. The images in the pseudo-PACS 810, even though they are not DICOM compliant, can be made available to all connected DICOM workstations and become part of the DICOM workflow to the extent technically possible.

FIG. 33 shows how a non-DICOM storage server can be configured into the IMPACS system 200. In the figure, NDIS-1 is a pathology image server that provides non-DICOM storage and images. This server NDIS-1 can be configured in the IMPACS system 200 as a slave PACS server 110 that requires a special connection protocol (involving non-DICOM access calls) along with rules that establish a custom tag-mapping from the proprietary tags used in these images into their DICOM equivalents. The IMPACS system 200 moreover can fill in certain DICOM tags automatically based on its knowledge of the storage setup as discussed in earlier sections. The important tags that require attention are the DICOM image UID tags which need to be mapped in a fashion that does not conflict with the DICOM standard. With these rules established, the IMPACS system 200 can build the master DICOM tag database 430 for this non-DICOM storage server NDIS-1 making it function as a pseudo-PACS 810 ensuring that it becomes part of the medical workflow, along with all the appropriate permissioning.

FIG. 34 illustrates how the IMPACS system 200 can serve up images from such a pseudo-PACS as created above. In this figure, the pseudo-PACS is indicated by NDPP-0. The IMPACS system 200 can serve up the images in this pseudo-PACS NDPP-0 to any connected workstation WS using its standard protocols. Given that images in the pseudo-PACS are not in DICOM format, the IMPACS system 200 performs several functions to provide this feature:

Image Conversion. The actual image from the pseudo-PACS 810 (ex tags) may often be in a custom format that is not supported by any standard DICOM viewer. In many cases, the IMPACS may be able to convert such a non-standard image format into a more standard format such as TIFF that can be displayed by a DICOM viewer in accordance with an image conversion protocol executed by an image conversion engine NDPP-1. Such conversion is generally possible to some degree with the caveat that we may not be able to always retain the fidelity of the original image.

Tag Wrapping. The IMPACS system 200 is configured to dynamically create a tag list for the image that conforms to DICOM format. For this purpose, it will use its custom mapping engine (which might involve a combination of its rules engine 440, Tag map/override database 432 and other custom configuration of its process brain 610) to extract the appropriate image tags NDPP-2 and combine them as needed with additional tags NDPP-3 for the image that it has already set up in its tag database 430 or which it has configured for such images through its rules engine 440 (even though these images are not DICOM to begin with). The image tags and pre-set tags need to be combined with the DICOM-formatted image obtained from the image conversion step NDPP-1 above to create a legal DICOM object as shown in NDPP-4.

DICOM delivery. The DICOM tags for the pseudo-PACS image and the converted (or actual) image (ex tags) as the case might be, now combined into a legal DICOM object NDPP-4 are now delivered to the requesting workstation WS. Technically, even if the binary image cannot be converted into any legal DICOM format, it will still be possible to wrap this image data in a DICOM tag wrapper (container) and use the IMPACS system 200 for delivery to the viewer. In this case, we would need a custom viewer that has the proper extensions to view the non-standard image.

By including non-DICOM images served up by non-PACS servers into a DICOM/PACS workflow, the IMPACS system 200 allows the same communications hardware and protocols to be used. Again, it allows for the complete incorporation of all security, audit and permissioning frameworks in place for handling images. And it can handle such images using this pseudo-PACS framework 810 until such time they are properly incorporated into the DICOM standard if at all.

6.8.3 Advantages Over Prior Art

The IMPACS system 200 systems and methods disclosed herein provide various advantages over the prior art. A primary advantage of the IMPACS system 200 is the interoperability functions it provides in its unification layer 400. Using its emulation functions 300 alone with a group of slave PACS servers $110_n$ is possible, but there is less benefit to outweigh the overhead of implementing the IMPACS system 200 unless the use of some or all of the unification functions 400 is anticipated.

Where it comes to unification, the IMPACS system 200 provides numerous advantages and is a superior alternative to other methodologies for achieving this. These advantages include:

Non-Disruptive Setup. The IMPACS system 200 can be introduced into a provider facility without disruption of the existing workflow. The IMPACS system 200 needs to build its maps of DICOM tags 430, patients 431, modalities 310 and client identities 518 as needed for each slave PACS server 110 before the latter can be added into the IMPACS framework 200. However, building these maps does not interfere with the provider's workflow at all. Even the data accesses needed to obtain the DICOM tags can be done during the provider's off hours so that there is no slow down of the PACS servers $110_n$ in times of heavy use.

Incremental Implementation. The IMPACS system 200 does not have to be implemented all at once for a given provider facility. A few modalities $M_n$ and/or clients can be switched over to the IMPACS system 200 to ensure that the system works as desired and that no problems occur before all the users $U_n$ and modalities $M_n$ are moved over. The existence of the emulation layer 300 in the IMPACS system 200 means that the various units attached to the IMPACS system 200 can continue to use their local (now slave) PACS' patient identifiers before migrating to the unified identifiers set up by the IMPACS system 200 as and when needed.

No Modification of Images. The IMPACS system 200 does not overwrite the slave PACS servers' $110_n$ existing images with new patient tags or any other information at all. In fact, the slave PACS servers' $110_n$ data can remain completely untouched by the IMPACS system 200. As such, there is no risk of compromising the important patient image data. Yet, the unification functions 400 work exactly as one would expect if the slave PACS data were all migrated to a single PACS server 110.

Minimal Data Replication. The IMPACS system 200 does not copy all the image data and as such does not require a dramatic increase in image storage requirements. What it does is copy some of the important DICOM tags from the slave PACS images to its own internal master DICOM tag databases 430 to permit high speed searching and retrieval of images and groupings from each slave PACS server 110. This limited copying and storage of tags can be minimized, though the cost for this will come in the form of slower image access because each of the slave PACS servers $110_n$ will then have to queried dynamically for this purpose.

Extensible Intelligence. The IMPACS system 200 can implement complex image rules that allow for multiple image backups in different PACS servers $110_n$, partitioning of storage by image type etc. It can also be made to send notifications to other PACS servers $110_n$ or clients when new images are stored or accessed. Even better it can support brand new modalities $M_n$ such as camera phones and support DICOM tag creation for any such new modalities $M_n$. In addition, it can incorporate non-DICOM images from a non-PACS image storage repository into a DICOM/PACS workflow. These extensions made possible by the IMPACS brain/control engine 201/process engine 610 make the IMPACS system 200 much more flexible for future medical imaging needs than any current PACS server $110_n$.

Superior Performance. The IMPACS system 200 can perform as well as a regular PACS server $110_n$ and could, in many cases, provide far better performance. This is because the IMPACS system 200 has a powerful engine that can be configured to provide all the patient mapping, image tag storage etc. all maintained within a high-performance database engine that many regular PACS servers $110_n$, especially in smaller provider facilities, lack. More importantly, the IMPACS system 200 has the ability to exploit multiple data stores to improve speeds. Thus, a regular PACS server 110 might have a backup PACS server 110 that it copies its images to, and the IMPACS system 200 can seamlessly optimize access by utilizing both stores to deliver the images to a workstation WS. Because of its extensible intelligence, the IMPACS system 200 can be taught to cache frequently used images or perform other access optimizations to improve performance even more.

The IMPACS system 200 is vastly different both in concept and in execution from conventional prior art approaches. The differences include at least the following:

Explicit Patient Unification for Interoperability. The IMPACS system 200 addresses a limitation of DICOM which is the non-global uniqueness of the patient identifier tag (PatientID) across images. Patient unification is a complex process that will vary depending on what types of slave PACS servers $110_n$ are being unified. Different techniques for unification will typically be needed based on the circumstances, geographic region, legal regulations etc. The IMPACS system 200 can handle a variety of mechanisms for patient unification be it using a separate subsystem or even a manual process. The unification provides the IMPACS system 200 with a specific patient's PatientID DICOM identifiers across all the slave PACS servers $110_n$ that are part of its network. With this information, the IMPACS system 200 can permit any authorized user to access all the images he is permissioned to see for a given patient across all the provider (slave) PACS servers $110_n$ exactly as though these images were all resident on the IMPACS system 200 itself. This will happen without any rewriting of any image tags in the slave PACS $110_n$.

Centralized and not Peer-To-Peer Design. Contrary to conventional approaches, the IMPACS system 200 inserts its central intelligence between every relevant modality $M_n$, workstation $WS_n$, user $U_n$ or any other client connecting to any of its component slave PACS servers 110 and the former do not peer with any of the slave PACS servers 110. In an implementation, it is not possible for any agent connected to the IMPACS system 200 to access any of the slave PACS servers $110_n$ except through the IMPACS system 200 itself, coming under its authentication and security frameworks. The connected entities are not even aware that the slave PACS servers $110_n$ even exist. Even in emulation mode 300 where the IMPACS system 200 behaves like one of the slave PACS servers $110_n$ it does not require that the actual slave PACS server 110 be connected, online or that it even actually exist, nor does this matter to the connecting agent. The emulation functions 300 provided by the IMPACS system 200, pertain to authentication and patient identifiers used for the images rather than explicit peering to a slave PACS server 110 and as such, the IMPACS system 200 can directly emulate the slave PACS server 110 (and its storage) internally in its software if needed. The image store in this context might be in a connected, yet separate database that may not even be able to function as a PACS server 110 except when serving images through the IMPACS system 200.

Centralized Roles and Permissioning. By defining its own user identities, roles and permissioning (maps 518 and 520) which map into the slave PACS server's 110 authorizations, the IMPACS system 200 can support a wide variety of granular or hierarchical access to its slave PACS server's 110 data. In fact, the IMPACS system 200, with some configuration, can operate with any authorization or permissioning protocol that might be desired as long as the users and agents defined by such a scheme can be mapped into appropriate image permissions at the slave PACS servers $110_n$. Known prior art approaches either do not directly address permissioning at all or suggest a framework for a doctor to request patient authorizations for image access. In the latter case this permissioning has to be done at the level of every hospital where the patient $P_n$ has images, effectively on a peer-to-peer basis and the onus is on the doctor to determine all the locations at which the patient's images are. For a patient $P_n$ with a common name like John Smith this should prove a herculean task. The IMPACS system 200 is designed to handle roles, access and permissioning across all hospitals within its own framework for all agents connected to it. It can tie easily into a specialized permissioning system to manage permissions as well if needed.

Complete Monitoring and Audit Trail of All Access. Since all access to any images has to go through the IMPACS system 200, the IMPACS system 200 can maintain a comprehensive audit trail and manage access at any level of granularity desired. As such, the IMPACS system 200 can also constantly monitor its connections for unusual access or hacks in a way that prevents any user, modality or workstation from bypassing such monitoring. Such an extensive degree of auditing, which might be needed for compliance with various government legal requirements for medical data, is simply not possible in conventional PACS systems 100 without adding on non-standard frameworks for the same.

Extensible DICOM Tag Intelligence to Permit Wider Use. The central engine of the IMPACS can seamlessly handle DICOM tag modification, patient anonymization etc. all of which can be done on the fly on image delivery to the user $U_n$/workstation $WS_n$ without modifying the images stored in the slave PACS servers $110_n$ at all. This can all be done by additions to the IMPACS system 200 logic, programming its brain/control engine 201 appropriately, without the need to create any new infrastructure, network links etc. Put differently, once the core IMPACS system 200 is in place, it can handle most use cases that one can envision for DICOM images across a variety of potential users. Thus, the IMPACS system 200 can deliver images to radiologists with full patient information, to researchers with patient anonymization, to insurers with additional patient tags as needed regarding their insurance identifiers etc. All this can be done using the same tag database obtained from the slave PACS servers $110_n$ when the IMPACS system 200 was set up. None of the conventional approaches to DICOM interoperability provides these features.

Modality and Device Monitoring to Enable New Methods for Image Storage and Retrieval. The IMPACS system 200 can be extended to analyze images and detect if they are from devices such as smart phones and cameras rather than medical modalities. The IMPACS system 200 can be programmed to provide custom DICOM tags for such images to permit storage in a slave PACS server 110. The IMPACS system 200 can detect the type of workstation that is using the final requested DICOM image and the speed of the connectivity to that workstation. As such, IMPACS system 200 can seamlessly compress the images for delivery over a slower connection, process images for display on a lower resolution device etc. all of which are possible because of its intelligence as represented by its process brain/control engine 201.

Lightweight Database that Can Easily be Tuned for Better Performance Using Replication, Caching and Other Techniques. Conventional approaches to DICOM interoperability take the speeds involved for image storage and delivery as a given. Many resort to peer-to-peer approaches for quicker image delivery recognizing that delivery of images from a PACS to a central system that sends it onward might be too slow. One known prior art approach addresses the problem of efficiency head-on with a completely new and disruptive networked file technology (that cannot be retrofitted onto existing PACS systems 100) with a central tag database. The IMPACS framework 200 is built for current computing environments where networking speeds are much faster. Bottlenecks because of the IMPACS' 200 internal processing can be dealt with by replicating its relatively lightweight implementation across multiple cloud-based servers. By analyzing its audit trails for image access, the IMPACS system 200 can cache frequently used images and deliver them quickly to requesting agents without even accessing the corresponding slave PACS 110. The IMPACS system 200 can even use advanced Web server methods to generate the speeds of peer-to-peer networking while still maintaining its centralized access and image delivery framework. While the IMPACS system 200 provides state of the art performance, it can be progressively improved for better performance based on the patterns of image access and use, and also be adapted to changes in technology. Conventional approaches do not provide for such usage-based improvements or provide a framework to capture such usage data, let alone enable tuning based on usage.

Accordingly, an IMPACS method and system 200 disclosed herein provides an improved, high performing, and extensible PACS server 110. Despite all its functionality, the IMPACS system 200 can appear to a user $U_n$ or modality $M_n$ just like a regular PACS server 110. No special configuration is needed for modalities $M_n$ or user workstations $WS_n$ (from a user's perspective) to connect to the IMPACS system 200 other than what a normal PACS server 110 might entail. The IMPACS system 200 can separate out the process of image access and handling from the images themselves in an efficient manner because of its lightweight central intelligence. The IMPACS system 200 can be deployed into a secure, cloud-based environment allowing it to be scaled without any modifications.

What I claim is:

1. A system for coordinating a process across at least two independent Picture Archiving and Communication System (PACS) to allow interoperability of the PACS, with each PACS handling the acquisition, retrieval, transmission, storage, and display of patients medical images using the Digital Imaging and Communications in Medicine (DICOM) standard, wherein each PACS includes at least one modality that acquires DICOM images, at least one workstation that retrieves and displays DICOM images, and at least one server that transmits, manages, and stores the images and controls the at least one modality and the at least one workstation, wherein each image has an associated DICOM tag and an associated patient tag unique to each PACS, wherein the process from one PACS to another PACS includes at least one process step defined by at least one modality, workstation, server, DICOM tag, or patient tag, wherein the servers of each PACS connect to the system as slaves, the system works with medical imaging workflows and interfaces with each PACS as the master controller for said PACS, the system comprising:

a. at least one database operable to store at least a list of the DICOM tags of each image from each PACS;

b. a rules engine operable to define a set of transformation rules for the image, modality, workstation, server, DICOM tag, patient tags, and process step from each PACS that link the image, modality, workstation, server, DICOM tag, patient tag, and process step from each PACS to such PACS such that each image, modality, workstation, server, DICOM tag, patient tag, and process step from each PACS has an identity or value assigned by the system and associated with such PACS that is unique across all PACS connected to the system;

c. a data unification and transformation engine operable to detect and resolve any conflict on the identities of the patient tag or values of the image, modality, workstation, server, DICOM tag, and process step from the modalities, workstations, servers, DICOM tags, patient tags, and process step from all PACS connected to the system resulting from said rules engine by tracking and assigning a unique super-identity for the patient tag and super-value for the image, modality, workstation, server, DICOM tag, and process step to each distinct modality, workstation, server, DICOM tag, patient tag, and process step for all PACS, and store the tracking and assignment of the super-identities of the patient tag and super-values of the image, modality, workstation, server, DICOM tag, and process step in said at least one database;

d. a security framework that controls access to each image from each PACS based on the assignment of the super-identities of the patient tag or super-values of the DICOM tag by said data unification and transformation engine and stored in said at least one database; and e. a control engine operable to perform the process steps to acquire, retrieve, transmit, store and/or display the images from any of said at least two PACS based on the DICOM tag and the assignment of the super-identities of the patient tag or super-values of the DICOM tag stored in said at least one database via an interface through which the control engine of the system interacts with connected PACS, including each PACS' modality, workstation, and server, wherein the system makes each PACS' images available through said interface utilizing the super-identities of the patient tag and super-values of the DICOM tag stored in said at least one database such that it appears to any PACS connected to the system as though the images were resident on the system itself even though the at least two PACS are independent and not directly connected to each other PACS and are only connected to the system.

2. The system of claim 1, further comprising a DICOM tag replication engine operable to replicate the DICOM tag of each image from each PACS, and store a copy of each DICOM tag of each image from each PACS in a DICOM tag database.

3. The system of claim 2, wherein each PACS further includes a modality that acquires or generates non-DICOM images, further comprising an extensible process engine operable to assigns a DICOM tag to each of said non-DICOM image by the system, and said assigned DICOM tags are stored in said DICOM tag database.

4. The system of claim 1 wherein each PACS further includes at least one user who can access certain DICOM images, wherein said rules engine further operable to define a set of transformation rules for the at least one user that link the user from each PACS to such PACS such that each user from each PACS has an identity assigned by the system and associated with such PACS that is unique across all PACS connected to the system;

wherein said data unification and transformation engine further operable to detect and resolve any conflict on the identities of the at least one users from all PACS connected to the system resulting from said rules engine by tracking and assigning a unique super-identity for each user to each distinct user for all PACS, and store the tracking and assignment of the super-identities of the at least one user in a user/role/group database.

5. The system of claim 4 wherein said security framework controls access by each of said at least one user to each image from each PACS based on the assignment of the super-identities stored in said user/role/group database.

6. The system of claim 1 further comprising a tag map/override database for storing the tracking and assignment of the super-values of each DICOM tag by said data unification and transformation engine using said rules engine.

7. The system of claim 1 further comprising a modality map database for storing the tracking and assignment of the super-values of each modality by said data unification and transformation engine using said rules engine.

8. The system of claim 1 further comprising a workstation map database for storing the tracking and assignment of the super-values of each workstation by said data unification and transformation engine using said rules engine.

9. The system of claim 1 further comprising a patient tag database for storing the tracking and assignment of the super-identities of each patient tag by said data unification and transformation engine using said rules engine.

10. The system of claim 1 further comprising a user interface that handles the acquisition, retrieval, transmission, storage, and display of DICOM images from each of said at least two PACS.

11. The system of claim 1 further comprising an extensible process engine operable to analyzes and optimizes said process steps performed by said control engine by utilizing the at least one database and information stored therein to access images in each PACS' server.

12. A system for coordinating a process for a Picture Archiving and Communication System (PACS) that handles the acquisition, retrieval, transmission, storage, and display of patients medical images using the Digital Imaging and Communications in Medicine (DICOM) standard, wherein said PACS includes at least one modality that acquires DICOM images, at least one workstation that retrieves and displays DICOM images, and at least one server that transmits, manages, and stores DICOM images and controls the at least one modality and the at least one workstation, wherein each image has an associated DICOM tag and an associated patient tag unique to each PACS, wherein the process includes at least one process step defined by at least one modality, workstation, server, DICOM tag, or patient tag, wherein the server of said PACS connects to the system as slave, the system works with medical imaging workflows and interfaces with said PACS as the master controller for said PACS, the system comprising:

a. at least one database operable to store at least a list of the DICOM tags of each image from said PACS;

b. a rules engine defining operable to define a set of transformation rules for each the image, modality, workstation, server, DICOM tag, patient tags, and process step from said PACS that link the image, modality, workstation, server, DICOM tag, patient tag, and process step to said PACS such that each image, modality, workstation, server, DICOM tag, patient tag, and process step has an identity or value assigned by the system and associated with said PACS that is unique in said PACS connected to the system;

c. a data unification and transformation engine operable to detect and resolve any conflict on the identities of the patient tag or values of the modalities, workstations, servers, DICOM tags, and process step from said PACS connected to the system resulting from said rules engine by tracking and assigning a unique super-identity for the patient tag and super-value for the image, modality, workstation, server, DICOM tag, and process step to each distinct modality, workstation, server, DICOM tag, patient tag, and process step for said PACS, and store the tacking and assignment of the super-identities of the patient tag and super-values of the images, modality, workstation, server, DICOM tag, and process step in said at least one database;

d. a security framework that controls access to each image from said PACS based on the assignment of the super-identities of the patient tag or super-values of the DICOM tag by said data unification and transformation engine and stored in said at least one database; and e. a control engine performing operable to perform the process steps to acquire, retrieve, transmit, stores and/or displays the images from said PACS based on the DICOM tag and the assignment of the super-identities of the patient tag or super-values of the DICOM tag stored in said at least one database via an interface through which the control engine of the system interacts with said PACS, including said PACS' modality, workstation, and server, wherein the system makes said PACS' images available through said interface utilizing the super-identities of the patient tag and super-values of the DICOM tag stored in said at least one database such that it appears to said PACS connected to the system as though the images were resident on the system itself even though said PACS is only connected to the system as slave.

13. A method for coordinating a process across at least two independent Picture Archiving and Communication System (PACS) to allow interoperability of the PACS, each PACS handles the acquisition, retrieval, transmission, storage, and display of patients medical images using the Digital Imaging and Communications in Medicine (DICOM) standard, wherein each PACS includes at least one modality that acquires DICOM images, at least one workstation that retrieves and displays DICOM images, and at least one server that transmits, manages, and stores DICOM images and controls the at least one modality and the at least one workstation, wherein each image has an associated DICOM tag and an associated patient tag unique to each PACS, wherein the process from one PACS to another PACS includes at least one process step defined by at least one modality, workstation, server, DICOM tag, or patient tag, comprising the steps of:

a. providing at least one database;

b. providing a rules engine that defines a set of transformation rules for the image, modality, workstation, server, DICOM tag, patient tags, and process step from each PACS that link the image, modality, workstation, server, DICOM tag, patient tag, and process step from each PACS to such PACS by assigning an identity or value to each image, modality, workstation, server, DICOM tag, patient tag, and process step from each PACS and associating them with such PACS that is unique across all PACS;

c. providing a data unification and transformation engine that detects and resolves any conflict on the identities of the patient tag or values of the image, modality, workstation, server, DICOM tab, and process step from the modalities, workstations, servers, DICOM tags, patient tags, and process step from all PACS connected to the system resulting from said rules engine, tracking and assigning a unique super-identity for the patient tag and super-value for the image, modality, workstation, server, DICOM tab, and process step to each distinct modality, workstation, server, DICOM tag, patient tag, and process step for all PACS;

d. storing a list of the DICOM tag of each image from each PACS in said at least one database;

e. storing the tracking and assignment of the super-identities of the patient tag and super-values of the image, modality, workstation, server, DICOM tab, and process step resulting from said data unification and transformation engine in said at least one database;

f. providing a security framework that controls access to each image from each PACS based on the assignment of the super-identities of the patient tag or super-values of the DICOM tag by said data unification and transformation engine stored in said at least one database;

g. providing a control engine that performs the process steps to acquire, retrieve, transmit, store and/or display the images from any of said at least two PACS based on the DICOM tag and the assignment of the super-identities of the patient tag or super-values of the DICOM tag stored in said at least one database;

h. connecting said at least two PACS to said control engine as slaves for medical imaging workflow;

i. providing an interface through which said control engine interacts with said at least two PACS, including each PACS' modality, workstation, and server;

j. making each PACS' images available through said interface by utilizing the super-identities of the patient tag and super-values of the DICOM tag stored in said at least one database such that it appears to any connected PACS as though the images were resident in the at least one database itself even though the at least two PACS are independent and not directly connected to each other PACS and are only connected to said control engine.

14. The method of claim 13 further comprising the step of providing an user interface that handles the acquisition, retrieval, transmission, storage, and display of DICOM images from each of said at least two PACS.

15. The method of claim 13 wherein said data unification and transformation engine does not alter the DICOM images stored in said at least one PACS.

16. The method of claim 13 wherein said data unification and transformation engine alters the DICOM tags stored in said at least one PACS.

* * * * *